US010914683B2

(12) United States Patent
Mahadevan-Jansen et al.

(10) Patent No.: US 10,914,683 B2
(45) Date of Patent: Feb. 9, 2021

(54) METHODS AND SYSTEMS FOR IDENTIFICATION OF BACTERIA IN BIOLOGICAL FLUID USING RAMAN SPECTROSCOPY AND APPLICATIONS OF SAME

(71) Applicant: Vanderbilt University, Nashville, TN (US)

(72) Inventors: Anita Mahadevan-Jansen, Nashville, TN (US); Oscar D. Ayala, Antioch, TN (US); Eric P. Skaar, Brentwood, TN (US); Catherine A. Wakeman, Lubbock, TX (US); Jay A. Werkhaven, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 40 days.

(21) Appl. No.: 16/342,318

(22) PCT Filed: Nov. 3, 2017

(86) PCT No.: PCT/US2017/059985
§ 371 (c)(1),
(2) Date: Apr. 16, 2019

(87) PCT Pub. No.: WO2018/085687
PCT Pub. Date: May 11, 2018

(65) Prior Publication Data
US 2019/0250105 A1  Aug. 15, 2019

Related U.S. Application Data

(60) Provisional application No. 62/416,983, filed on Nov. 3, 2016.

(51) Int. Cl.
*G01N 21/65* (2006.01)
*G01N 33/569* (2006.01)
(Continued)

(52) U.S. Cl.
CPC ............ *G01N 21/65* (2013.01); *G01J 3/0218* (2013.01); *G01J 3/44* (2013.01);
(Continued)

(58) Field of Classification Search
CPC .......... G01J 3/0218; G01J 3/44; G01N 21/65; G01N 33/56911; G01N 2021/656;
(Continued)

(56) References Cited

U.S. PATENT DOCUMENTS 6,379,920 B1    4/2002  El-Sayed et al.
2004/0073120 A1*  4/2004  Motz .................... A61B 5/0086
                                                              600/478
(Continued)

FOREIGN PATENT DOCUMENTS

WO    2007056568 A2    5/2007

OTHER PUBLICATIONS

Dacraemer, WF, Maes, MA, and Vanhuyse, VJ. An elastic stress-strain relation for soft biological tissues based on a structural model. Journal of Biomechanics, 1980, 13:463-468.
(Continued)

*Primary Examiner* — Mark R Gaworecki
(74) *Attorney, Agent, or Firm* — Locke Lord LLP; Tim Tingkang Xia, Esq.

(57) ABSTRACT

The invention relates to a method for identification and discrimination of bacteria and/or mutant bacterial strains in a biological fluid. The method includes illuminating the biological fluid with a beam of light; obtaining Raman data from light scattered from the illuminated biological fluid; and finding Raman signatures corresponding to each type of bacteria and/or mutant bacterial strains from the obtained Raman data, so as to identify and discriminate each type of bacteria and/or mutant bacterial strains in the biological fluid from the Raman signatures.

39 Claims, 37 Drawing Sheets

(51) Int. Cl.
    *G01J 3/02* (2006.01)
    *G01J 3/44* (2006.01)
(52) U.S. Cl.
    CPC . *G01N 33/56911* (2013.01); *G01N 2021/656* (2013.01); *G01N 2201/0833* (2013.01); *G01N 2333/212* (2013.01); *G01N 2333/285* (2013.01); *G01N 2333/31* (2013.01); *G01N 2333/315* (2013.01); *G01N 2800/14* (2013.01)
(58) Field of Classification Search
    CPC ..... G01N 2201/0833; G01N 2333/212; G01N 2333/285; G01N 2333/31; G01N 2333/315; G01N 2800/14
    See application file for complete search history.

(56) References Cited

U.S. PATENT DOCUMENTS

| | | |
|---|---|---|
| 2009/0021724 A1 | 1/2009 | Mahadevan-Jansen et al. |
| 2010/0145200 A1* | 6/2010 | Mahadevan-Jansen ..................... A61B 1/07 600/476 |
| 2012/0010483 A1 | 1/2012 | Mahadevan-Jansen et al. |
| 2016/0007840 A1 | 1/2016 | Boppart et al. |

OTHER PUBLICATIONS

Watters GW, Jones JE, Freeland AP. The predictive value of tympanometry in the diagnosis of middle ear effusion. Clinical Otolaryngology Allied Science, 1997, 22(4):343-345.
L. Hall-Stoodley, F.Z. Hu, A. Gieseke, L. Nistico, D. Nguyen, J. Hayes, et al., Direct detection of bacterial biofilms on the middle-ear mucosa of children with chronic otitis media, JAMA, 2006, 296:202-211.
L. P. Schousboe, T. Ovesen, L. Eckhardt, L.M. Rasmussen, C.B. Pedersen, How does endotoxin trigger inflammation in otitis media with effusion? Laryngoscope, 2001, 111:297-300.
U. Gok, Y. Bulut, E. Keles, S. Yalcin, M.Z. Doymaz, Bacteriological and PCR analysis of clinical material aspirated from otitis media with effusions, Int. J. Pediatr. Otorhinolaryngology, 2001, 60:49-54.
D.M. Poetker, D.R. Lindstrom, C.E. Edmiston, C.J. Krepel, T.R. Link, J.E. Kerschner, Microbiology of middle ear effusions from 292 patients undergoing tympanostomy tube placement for middle ear disease, Int. J. Pediatr. Otorhinolaryngol. 69 (2005) 799-804.
C.D. Bluestone, J.S. Stephenson, Martin, Ten-year review of otitis media pathogens, Pediatr. Infect. Dis. J. 11 (8 Suppl.) (1992) S7-S11.
Daniel, M, Imtiaz-Umer, S, Fergie, N, Birchall, JP, Bayston, R. Bacterial involvement in otitis media with effusion. International Journal of Pediatric Otorhinolaryngology, 2012, 76:1416-1422.
Maquelin, K, Kirschner, C, Choo-Smith, L-P., van den Braak, N., Endtz, H.Ph., Naumann, D., Puppels, G.J. Identification of medically relevant microorganisms by vibrational spectroscopy. Journal of Microbiological Methods, 2002, 51:255-271.
Dai, T, Gupta, A, Huang, Y-Y, Sherwood, ME, Murray, CK, Vrahas, MS, Kielian, T, Hamblin, MR. Blue Light Eliminates Community-Acquired Methicillin-Resistant *Staphylococcus aureus* in Infected Mouse Skin Abrasions. Photomedicine and Laser Surgery, 2013, 31(11): p. 531-538.
Moffit, Chen, Y-C, and Prahl, SA. Preparation and characterization of polyurethane optical phan- toms. Journal of Biomedical Optics, 2006, 11(4):041103.
Wang, J, Bergholt, MS, Zheng, W, Huang, Z. Development of a beveled fiber-optic confocal Raman probe for enhancing in vivo epithelial tissue Raman measurements at endoscopy. Optics Letters, 2013, 38(13):2321-2323.
Keller, MD, Vargis, E, Granja, NM, Wilson, RH, Mycek, MA, Kelley, MC, Mahadevan-Jansen, A. Development of a spatially offset Raman spectroscopy probe for breast tumor surgical margin evaluation. Journal of Biomedical Optics, 2011, 16(7): 0077006.
Ehrlich, GD, Veeh, R, Wang, X, Costerton, JW, Hayes, JD, Hu, FZ, Diagle, BJ, Ehrlich, MD, Post, JC. Mucosal biofilm formation on middle-ear mucosa in the chinchilla model of otitis media. Journal of the American Medical Association, 2002, 287(13):1710-1715.
S. S. Magill et al., "Multistate Point-Prevalence Survey of Health Care—Associated Infections," N. Engl. J. Med., vol. 370, No. 13, pp. 1198-1208, 2014.
L. L. Leape et al., "The nature of adverse events in hospitalized patients: Results of the Harvard Medical Practice Study II," vol. 324, No. 6, pp. 377-384, 1991.
R. D. Scott II, "The direct medical costs of healthcare-associated infections in U.S. hospitals and the benefits of prevention," 2009.
G. A. Noskin et al., "The burden of *Staphylococcus aureus* infections on hospitals in the United States," vol. 165, pp. 1756-1761, 2005.
M. Sangappa and P. Thiagarajan, "Methicillin Resistant *Staphylococcus aureus*: Resistance Genes and Their Regulation," Int. J. Pharm. Pharm. Sci., vol. 4, pp. 658-667, 2012.
J. Fishovitz, J. A. Hermoso, M. Chang, and S. Mobashery, "Penicillin-binding protein 2a of methicillin-resistant *Staphylococcus aureus*," IUBMB Life, vol. 66, No. 8, pp. 572-577, 2014.
E. Klein, D. L. Smith, and R. Laxminarayan, "Hospitalizations and deaths caused by methicillin-resistant *Staphylococcus aureus* , United States, 1999-2005," vol. 13, No. 12, pp. 1840-1846, 2007.
O. Melter and B. Radojevič, "Small Colony Variants of *Staphylococcus aureus*—review," Folia Microbiol. (Praha)., vol. 55, No. 6, pp. 548-558, 2010.
F. Kipp et al., "Evaluation of Two Chromogenic Agar Media for Recovery and Identification of *Staphylococcus aureus* Small-Colony Variants," J. Clin. Microbiol., vol. 43, No. 4, pp. 1956-1959, 2005.
M. R. Precit, D. J. Wolter, A. Griffith, J. Emerson, J. L. Burns, and L. R. Hoffman, "Optimized In Vitro Antibiotic Susceptibility Testing Method for Small-Colony Variant *Staphylococcus aureus*," Antimicrob. Agents Chemother., vol. 60, No. 3, pp. 1725-1735, 2016.
P. W. Groundwater et al., "Methods for the detection and identification of pathogenic bacteria: past, present, and future," Chem. Soc. Rev., vol. 46, No. 16, pp. 4818-4832, 2017.
P. Kralik and M. Ricchi, "A Basic Guide to Real Time PCR in Microbial Diagnostics: Definitions , Parameters , and Everything," Front. Microbiol., vol. 8, No. 108, pp. 1-9, 2017.
W. E. Huang, R. I. Griffiths, I. P. Thompson, M. J. Bailey, and A. S. Whiteley, "Raman microscopic analysis of single microbial cells," Anal. Chem., vol. 76, No. 15, pp. 4452-4458, 2004.
K. Maquelin et al., "Prospective study of the performance of vibrational spectroscopies for rapid identification of bacterial and fungal pathogens recovered from blood cultures.," J. Clin. Microbiol., vol. 41, No. 1, pp. 324-329, 2003.
S. Pahlow, S. Meisel, D. Cialla-May, K. Weber, P. Rosch, and J. Popp, "Isolation and identification of bacteria by means of Raman spectroscopy," Adv. Drug Deliv. Rev., vol. 89, pp. 105-120, 2015.
O. Ayala et al., "Characterization of bacteria causing acute otitis media using Raman microspectroscopy," Anal. Methods, vol. 9, pp. 1864-1871, 2017.
G. Y. Liu et al., "*Staphylococcus aureus* golden pigment impairs neutrophil killing and promotes virulence through its antioxidant activity," J. Exp. Med., vol. 202, No. 2, pp. 209-215, 2005.
K. Czamara, K. Majzner, M. Z. Pacia, K. Kochan, A. Kaczor, and M. Baranska, "Raman spectroscopy of lipids: a review," J. Raman Spectrosc., vol. 46, pp. 4-20, 2014.
R. Procter, A. Kriegeskorte, B. Kahl, K. Becker, B. Loftier, and G. Peters, "*Staphylococcus aureus* Small Colony Variants (SCVs ): a road map for the metabolic pathways involved in persistent infections," Front. Cell. Infect. Microbiol., vol. 4, No. 99, pp. 1-8, 2014.
E. Duthie and L. Lorenz, "Staphylococcal Coagulase: Mode of Action and Antigenicity," Microbiology, vol. 6, pp. 95-107, 1952.
C. L. C. Wielders, A. C. Fluit, S. Brisse, J. Verhoef, and F. J. Schmitz, "mecA gene is widely disseminated in *Staphylococcus aureus* population," J. Clin. Microbiol., vol. 40, No. 11, pp. 3970-3975, 2002.

(56) References Cited

OTHER PUBLICATIONS

B. Ballhausen, A. Kriegeskorte, N. Schleimer, G. Peters, and K. Becker, "The mecA homolog mecC confers resistance against β-lactams in *Staphylococcus aureus* irrespective of the genetic strain background," Antimicrob. Agents Chemother., vol. 58, No. 7, pp. 3791-3798, 2014.

L. Lan, A. Cheng, P. M. Dunman, D. Missiakas, and C. He, "Golden Pigment Production and Virulence Gene Expression Are Affected by Metabolisms in *Staphylococcus aureus*," J. Bacteriol., vol. 192, No. 12, pp. 3068-3077, 2010.

A. Qamar and D. Golemi-Kotra, "Dual Roles of FmtA in *Staphylococcus aureus* Cell Wall Biosynthesis and Autolysis," Antimicrob. Agents Chemother., vol. 56, No. 7, pp. 3797-3805, 2012.

B. R. Boles, M. Thoendel, A. J. Roth, and A. R. Horswill, "Identification of Genes Involved in Polysaccharide-Independent *Staphylococcus aureus* Biofilm Formation," PLoS One, vol. 5, No. 4, 2010.

N. D. Hammer et al., "Two Heme-Dependent Terminal Oxidases Power *Staphylococcus aureus* Organ-Specific Colonization of the Vertebrate Host," MBio, vol. 4, No. 4, pp. 1-9, 2013.

C. Von Eiff, C. Heilmann, R. A. Proctor, C. Woltz, G. Peters, and F. Glötz, "A site-directed *Staphylococcus aureus* hemB mutant is a small-colony variant which persists intracellularly," J. Bacteriol., vol. 179, No. 15, pp. 4706-4712, 1997.

C. A. Wakeman et al., "Menaquinone biosynthesis potentiates haem toxicity in *Staphylococcus aureus*," Mol. Microbiol., vol. 86, No. 6, pp. 1376-1392, 2013.

J. Shlens, "A Tutorial on Principal Component Analysis," 2014.

Rovers, M. M. The burden of otitis media. Vaccine 26, 2-8 (2008).

Monasta, L. et al. Burden of disease caused by otitis media: Systematic review and global estimates. PLoS One 7, (2012).

Berman, S. Review Otitis Media in Developing Countries. 96, (1995).

Harmes, K. M. et al. Otitis media: diagnosis and treatment. Am. Fam. Physician 88, 435-40 (2013).

Lieberthal, A. S. et al. The Diagnosis and Management of Acute Otitis Media. Pediatrics 131, e964-e999 (2013).

Kathleen A. Daly and G. Scott Giebink. Clinical epidemiology of otitis media. Pediatr. Infect. Dis. J. 19, S31-S36 (2000).

Paul G. Shekelle, Glenn Takata, Sydne J. Newberry, Tumaini Coker, Mary Ann Limbos, Linda S. Chan, Martha J. Suttorp, Jason Carter, Aneesa Motala, Di Valentine, Breanne Johnsen, R. S. Management of acute otitis media. Evid. Rep. Technol. Assess. (Full. Rep). 1-426 (2010).

American Academy of Family Physicians, American Academy of Otolaryngology-Head and Neck Surgery, and A. A. of P. S. on O. M. W. E. American academy of pediatrics. Pediatrics 113, 1412-1429 (2004).

Pelton, S. I. Otoscopy for the diagnosis of otitis media. Pediatr. Infect. Dis. J. 17, 540-543 (1998).

Sundberg, M., Peebo, M., Oberg, P. A., Lundquist, P. G. & Strömberg, T. Diffuse reflectance spectroscopy of the human tympanic membrane in otitis media. Physiol. Meas. 25, 1473-1483 (2004).

Sorrell, M. J., Tribble, J., Reinisch, L., Werkhaven, J. A. & Ossoff, R. H. Bacteria identification of otitis media with fluorescence spectroscopy. Lasers Surg. Med. 14, 155-163 (1994).

Brian C. Spector, Lou Reinisch, Dana Smith, J. A. W. Noninvasive fluorescent identification of bacteria causing acute ptitis media in a chinchilla model. The Laryngoscope2 110, 1119-1123 (2000).

Monroy, G. L. et al. Noninvasive depth-resolved optical measurements of the tympanic membrane and middle ear for differentiating otitis media. Laryngoscope 125, E276-E282 (2015).

Ellis, D. I., Cowcher, D. P., Ashton, L., O'Hagan, S. & Goodacre, R. Illuminating disease and enlightening biomedicine: Raman spectroscopy as a diagnostic tool. Analyst 138, 3871-84 (2013).

Tu, Q. & Chang, C. Diagnostic applications of Raman spectroscopy. Nanomedicine Nanotechnology, Biol. Med. 8, 545-558 (2012).

Maquelin, K., Vreeswijk, T. Van, Endtz, H. & Smith, B. Raman spectroscopic method for identification of clinically relevant.Anal. Chem72, 12-19 (2000).

Sandt, C., Smith-Palmer, T., Pink, J., Brennan, L. & Pink, D. Confocal Raman microspectroscopy as a tool for studying the chemical heterogeneities of biofilms in situ. J. Appl. Microbiol. 103, 1808-1820 (2007).

Maquelin, K. et al. Raman spectroscopic typing reveals the presence of carotenoids in Mycoplasma pneumoniae. Microbiology 155, 2068-2077 (2009).

de Siqueira e Oliveira, F. S., Giana, H. E. & Silveira, L Discrimination of selected species of pathogenic bacteria using near-infrared Raman spectroscopy and principal components analysis. J. Biomed. Opt. 17, 107004 (2012).

Jarvis, R. M., Brooker, A. & Goodacre, R. Surface-enhanced Raman scattering for the rapid discrimination of bacteria. Faraday Discuss. 132, 281-292 (2006).

Lieber C.A., M.-J. A. Automated Method for Subtraction of Flourescence from Biological Raman Spectra. As 57, 1363-1367 (2003).

Savitzky, A. & Golay, M. J. E. Smoothing and Differentiation of Data by Simplified Least Squares Procedures. Anal. Chem. 36, 1627-1639 (1964).

Krishnapuram, B., Carin, L., Figueiredo, M. A. T. & Hartemink, A. J. Sparse multinomial logistic regression: Fast algorithms and generalization bounds. IEEE Trans. Pattern Anal. Mach. Intell. 27, 957-968 (2005).

Pence, I. J., Patil, C. A., Lieber, C. A. & Mahadevan-Jansen, A. Discrimination of liver malignancies with 1064 nm dispersive Raman spectroscopy. Biomed. Opt. Express 6, 2724-37 (2015).

Ventola, C. L. The antibiotic resistance crisis: part 1: causes and threats. P T A peer-reviewed J. Formul. Manag. 40, 277-83 (2015).

Post, J. C. et al. Molecular analysis of bacterial pathogens in otitis media with effusion. Jama 273, 1598-1604 (1995).

Matar, G. M., Sidani, N., Fayad, M. & Hadi, U. Two-step PCR-based assay for identification of bacterial etiology of otitis media with effusion infected Lebanese children. J. Clin. Microbiol. 36, 1185-1188 (1998).

Rayner, M. G. et al. Evidence of bacterial metabolic activity in culture-negative otitis media with effusion. JAMA 279, 296-9 (1998).

Woude, M. W. Van Der & Bäumler, A. J. Phase and Antigenic Variation in Bacteria Phase and Antigenic Variation in Bacteria. Clin. Microbiol. Rev. 17, 581-611 (2004).

Lafontaine, E. R. et al. Expression of the Moraxella catarrhalis UspA1 Protein Undergoes phase Variation and Is Regulated at the Transcription Level. J. Bacteriol. 183, 1540-1551 (2001).

Oust, A. et al. Fourier Transform Infrared and Raman Spectroscopy for Characterization of Listeria monocytogenes Strains. Society 72, 228-232 (2006).

Leibovitz, E., Broides, A., Greenberg, D. & Newman, N. Current management of pediatric acute otitis media. Expert Rev. Anti. Infect. Ther. 8, 151-161 (2010).

Grossman, Z. et al. Antibiotic prescribing for upper respiratory infections: European primary paediatricians'knowledge attitudes and practice. ActaPaediatr. Int. J. Paediatr. 101, 935-940 (2012).

Zielnik-Jurkiewicz, B. & Bielicka, A. Antibiotic resistance of *Streptococcus pneumoniae* in children with acute otitis media treatment failure. Int. J. Pediatr. Otorhinolaryngol. 79, 2129-2133 (2015).

Dagan, R. Treatment of acute otitis media—Challenges in the era of antibiotic resistance. Vaccine 19, 2-9 (2000).

Klein, JO, The burden of otitis media. Vaccine, 2001, 19:S2-S8.

Ahmed, S, Incremental health care utilization and costs for acute otitis media in children. The Laryngoscope, 2014, 124:301-305.

Burrows, HL, et al., Otitis Media Guideline Team. University of Michigan Health System otitis media guideline, 2013, http://www.med.umich.edu/1info/fhp/practiceguides/om/OM.pdf.

Pichichero, ME, Acute Otitis Media: Part I. Improving Diagnostic Accuracy. American Family Physician, 2000, 61(7):2051-2056.

Marchetti F, Ronfani L, Nibali SC, et al.; Italian Study Group on Acute Otitis Media. Delayed prescription may reduce the use of antibiotics for acute otitis media: a prospective observational study in primary care.Arch Pediatr Adolesc Med. 2005, 159(7):679-684.

Burkhard, MD and Sachs, RM. Anthropometric manikin for acoustic research. Journal of the Acoustical Society of America, 1975, 58:214-222.

(56) References Cited

OTHER PUBLICATIONS

Muller, C. Tympanoplasty. Grand Rounds paper. Houston: Department of Otolaryngology. University of Texas. Retrieved Nov. 4, 2015 from http://www.utmb.edu/otoref/Grnds/T-plasty-030115/T-plastyslides-030115.pdf.

Alvord, LS and Farmer, BL. Anatomy and orientation of the human external ear. Journal of the American Academy of Audiology, 1997, 8:383-390.

Bekesy, G von. The structure of the middle ear and hearing of one's own voice by bone conduction. Journal of the Acoustical Society of America, 1949, 21:217-232.

Stinson, MR and Lawton BW. Specification of geometry of the human ear canal for the predication of sound-pressure level distribution. Journal of the Acoustical Society of America, 1989, 85:2492-2503.

Decreamer, EF, Dirckx, JJ, and Funnell, WR. Shape and derived geometrical parameters of the adult, human tympani membrane measure with a phase-shift moire interferometer. Hearing Research, 1991, 51:107-121.

Sundberg, M. (2008). Optical methods for tympanic membrane characterization. Linkoping Studies in Science and Technology, Dissertation No. 1173. Linkoping (Sweden) L Liu-Tryck.

Gelfand, H. (1998). Hearing: An Introduction to Psychological and Physiological Acoustics. New York: Mercel Decker.

Lim, DJ. Human tympanic membrane: An ultrastructural observation. Acta Otolaryngologica, 1970, 70:176-186.

Korean Intellectual Property Office (ISR/KR), "International Search Report for PCT/US2017/059985", Korea, Feb. 14, 2018.

\* cited by examiner

METHODS AND SYSTEMS FOR IDENTIFICATION OF BACTERIA IN BIOLOGICAL FLUID USING RAMAN SPECTROSCOPY AND APPLICATIONS OF SAME

CROSS-REFERENCE TO RELATED PATENT APPLICATION

This PCT application claims priority to and the benefit of, U.S. Provisional Patent Application Ser. No. 62/416,983, filed Nov. 3, 2016, entitled "METHOD FOR REAL-TIME IDENTIFICATION OF BACTERIA IN FLUID ENVIRONMENT USING RAMAN SPECTROSCOPY AND APPLICATION OF SAME," by Anita Mahadevan-Jansen et al. The entire disclosure of the above-identified application is incorporated herein by reference.

Some references, which may include patents, patent applications, and various publications, are cited and discussed in the description of the present invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, [n] represents the nth reference cited in the reference list. For example, [26] represents the first reference cited in the reference list, namely, Pence, I. J., Patil, C. A., Lieber, C. A. & Mahadevan-Jansen, A. Discrimination of liver malignancies with 1064 nm dispersive Raman spectroscopy. *Biomed. Opt. Express* 6, 2724-37 (2015).

STATEMENT AS TO RIGHTS UNDER FEDERALLY-SPONSORED RESEARCH

The present invention was made with government support under and awarded by DoD, Air Force of Scientific Research, National Defense and Engineering Graduate (NDSEG) Fellowship, 32 CFR 168a. The government has certain rights in the invention.

FIELD OF THE INVENTION

The present invention relates generally to applications of Raman spectroscopy, and more particularly to methods and systems for identification of bacteria in a biological fluid using Raman spectroscopy and applications of the same.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

Otitis media (OM), an inflammatory disease of the middle ear, is the leading cause of acute physician visits and prescription of antibiotics for children [1]. Worldwide, there are over 700 million cases of acute otitis media (AOM) every year with 51% of these cases occurring in children less than five years of age [2]. The impact of AOM can extend beyond an infection, possibly leading to complications such as mastoiditis, chronic suppurative otitis media (CSOM), and hearing impairment, which may be severely debilitating for child development [3]. Otitis media with effusion (OME) is one of the two types of OM and is described as asymptomatic inflammation of the middle ear with a build-up of fluid in the middle ear space. Contrary to OME, AOM presents with a rapid onset of signs and symptoms, such as fever, associated with acute infection within the middle ear. AOM is commonly caused by an active bacterial infection in the upper respiratory tract that is refluxed into the middle ear space. Antibiotic therapy is prescribed to manage AOM in children six months and older presenting severe signs and symptoms, while antibiotic treatment is not recommended for children with OME. Currently, clinical diagnosis of AOM is based on visual evaluation of the tympanic membrane (TM) and symptoms caused by the infection. Clinical guidelines issued by the American Academy of Family Physicians (AAFP) and American Academy of Pediatrics (AAP) are based on visual evidence such as bulging of the TM with recent onset of ear pain or erythema to diagnose AOM [4]. These symptoms are further assessed using a pneumatic otoscope, the current standard tool for diagnosing OM. Additionally, diagnosis relies on the assessment of the contour, color, translucency, and mobility of the TM [5]. Pneumatic otoscopy allows the physicians to view the TM and apply pressure to observe its mobility. Pneumatic otoscopy is 70%-90% sensitive and specific for determining accumulation of middle ear effusion (MEE) in the middle ear, which usually develops post-infection [5-9]. Basic otoscopy, which relies only on subtle visual changes of the tympanic membrane, has a sensitivity and specificity of 60%-70% [7, 8]. Although pneumatic otoscopy improves visualization of symptomatic changes in the TM, findings are not able to identify or correlate with bacteria causing an infection. Other techniques, though less commonly implemented in routine clinical care include: tympanometry, which measures TM compliance using sound; acoustic reflectometry, which seeks to identify the presence of fluid behind the TM by emitting and detecting the reflected sound; and tympanocentesis, which is an invasive technique used to extract MEE through the tympanic membrane to be cultured for identification of bacteria causing an infection. Pneumatic otoscopy and tympanometry are limited in their performance and do not detect or identify bacteria in ear effusion. Tympanocentesis then, is currently the "gold standard" for identifying bacteria causing an ear infection. In addition to the invasive nature of the procedure, not all fluid may be collected and more importantly not all MEE is easily cultured, delaying identification of bacteria causing an infection. In fact, tympanocentesis is rarely practiced and only performed when antibiotic treatment is repeatedly unsuccessful, which can still result in not identifying the causative microorganisms. This gap of diagnostic information may cause physicians to over-prescribe antibiotics for cases of OME, which are rarely caused by a bacterial infection, or prescription of antibiotics to pathogens that have developed resistance to specific classes of antibiotics in acute infections.

Optical spectroscopy has in recent years received significant attention for disease diagnosis. Optical methods that have been explored for detecting OM include diffuse reflectance spectroscopy, fluorescence spectroscopy, and optical coherence tomography (OCT). Diffuse reflectance spectroscopy utilizing a coupled fiber-optic bundle with an otoscope has been used to distinguish the color of the tympanic membrane for diagnosis of AOM in 15 normal and 15 AOM patients [10]. While this group was able to distinguish between OM with mucous versus serous effusion, the performance of the technique to differentiate between AOM and OME was limited since it relied primarily on detecting the inflammatory state of the TM. Fluorescence spectroscopy has also been used in vitro to characterize the main bacteria that cause OM and to create a library of fluorescence features of these pathogens [11]. In a subsequent publication, fluorescence was measured from 12 chinchilla AOM models in vivo with limited success [12]. OCT, an optical imaging method that provides high-resolution real-time in vivo images of tissue microstructures, has been used to measure the thickness of the human TM at different infection states in vivo [13]. Researchers of this study were able to classify normal, acute, and chronic states of OM in adult patients based on TM thickness and biofilm formation for chronic cases. Performance accuracy of 70-80% was achieved due in part to the lack of consistency in biofilm growth across the TM and in all patients. Although all three optical methods were researched with the goal of in vivo application, these approaches are limited by their poor specificity and inability to detect and identify bacteria that cause AOM.

Raman spectroscopy (RS) is an optical technique that uses inelastically scattered light to provide biochemical information of a particular sample. This technique is sensitive to biochemical features such as nucleic acids, lipids, proteins, and carbohydrates and is able to provide a biochemical profile without the need of added contrast agents. RS has been used for many years to probe the biochemistry of various biological molecules [14] and more recently for disease detection [15-17]. More specifically, RS has been applied to characterize and identify bacteria in vitro as a proof of concept design. One example includes utilizing RS to characterize bacterial signatures in microbial colonies with the goal of detecting their presence in a shorter incubation time [18]. Another research group used a benchtop confocal Raman microscopy to identify bacteria within a mixed bacteria biofilm model [19]. Furthermore, Raman microspectroscopy has been used for *Mycoplasma pneumoniae* strain typing to distinguish between multiple clusters of strains [20]. The feasibility of implementing a fiber-optic probe-based Raman system to characterize spectral signatures of bacterial colonies has also been shown and used to determine biochemical features important for distinguishing between Gram-positive and Gram-negative bacteria [21]. Interrogation of bacterial components such as surface wall features has also been investigated using surface-enhanced RS (SERS), which involves the addition of nanoparticles to the sample to enhance the Raman signal of targeted biomarkers [22]. Although these studies have shown the potential of RS for bacterial detection and identification, no studies to date have investigated bacteria that cause AOM and none have focused on the potential development for in vivo application. Currently, there is no tool available to rapidly and non-invasively detect the presence and identity of bacteria causing a middle ear infection.

Therefore, a heretofore unaddressed need exists in the art to address the aforementioned deficiencies and inadequacies.

SUMMARY OF THE INVENTION

One of the objectives of this invention is to determine the feasibility of discriminating between the three main bacteria that cause acute otitis media (AOM). Successful classification of these species is accomplished by spectrally characterizing their biochemical composition. The embodiments of the invention present the ability to classify bacteria causing the AOM using Raman microspectroscopy and assess the feasibility of developing this technique for the diagnosis of the AOM.

In one aspect, the invention relates to a method for identification and discrimination of bacteria and/or mutant bacterial strains in a biological fluid. In one embodiment, the method includes illuminating the biological fluid with a beam of light; obtaining Raman data from light scattered from the illuminated biological fluid; and finding Raman signatures corresponding to each type of bacteria and/or mutant bacterial strains from the obtained Raman data, so as to identify and discriminate each type of bacteria and/or mutant bacterial strains in the biological fluid from the Raman signatures. In one embodiment, the biological fluid comprises a middle ear fluid (MEF). In one embodiment, the biological fluid may be spread out on a substrate. In one embodiment, the bacteria that cause acute otitis media (AOM) in the biological fluid comprise *H. influenzae, M. catarrhalis*, and/or *S. pneumoniae*. In another embodiment, the bacteria comprise *S. agalactiae, S. aureus*, and/or the like. The mutant bacterial strains are from the *S. aureus* parent strain.

In one embodiment, the illuminating step comprises illuminating the biological fluid with the beam of light from a near-infrared light source.

In one embodiment, the obtaining step comprises collecting the scattered light with an optical probe and obtaining Raman spectra of the scattered light into with a spectrometer.

In one embodiment, the finding step comprises processing the obtained Raman spectra to find the Raman signatures corresponding to each type of bacteria.

In one embodiment, the processing step is performed with a sparse multinomial logistic regression (SMLR) algorithm.

In one embodiment, the finding step comprises comparing the obtained Raman spectra with a library of biochemical features that contains Raman spectral features of each type of bacteria and/or mutant and/or resistant bacterial strains to identify and discriminate the Raman signatures corresponding to each type of bacteria and/or mutant and/or resistant bacterial strains.

In one embodiment, the Raman signatures comprise peaks and its corresponding wavelengths in the Raman spectra.

In another aspect, the invention relates to a system for identification and discrimination of bacteria and/or mutant and/or resistant bacterial strains in a biological fluid. In one embodiment, the system includes an optical probe optically connected to a light source for emitting a beam of light and configured to deliver the beam of light emitted from the light source to the biological fluid and to collect light scattered from the illuminated biological fluid; a detector optically coupled with the optical probe, for obtaining Raman data from the collected scattered light; and a controller in communication with the detector and programmed for finding Raman signatures corresponding to each type of bacteria and/or mutant bacterial strains from the obtained Raman data and identifying and discriminating each type of bacteria and/or mutant bacterial strains in the biological fluid from the Raman signatures. In one embodiment, the biological fluid comprises a middle ear fluid (MEF). In one embodiment, the bacteria that cause acute otitis media (AOM) in the biological fluid comprise *H. influenzae, M. catarrhalis*, and/or *S. pneumoniae*. In another embodiment, the bacteria comprise *S. agalactiae, S. aureus*, and/or the like. The mutant bacterial strains are from the *S. aureus* parent strain.

In one embodiment, the light source comprises a laser or light emitting diodes (LEDs). In one embodiment, the beam of light has a wavelength in a near-infrared range.

In one embodiment, the optical probe has a working end, a source channel and a plurality of collection channels, wherein the working end is operably positioned proximate to a surface of the biological fluid, the source channel is configured to deliver the beam of light emitted by the light source from the working end to the surface of the biological fluid, and the collection channels are configured to collect from the working end light scattered from the illuminated biological fluid.

In one embodiment, the optical probe comprises a plurality of optical fibers spatially arranged in a fiber array.

In one embodiment, at least one fiber of the plurality of optical fibers is a source optical fiber for delivering the beam of light emitted from the light source to the surface of the biological fluid, and the remaining fibers of the plurality of optical fibers are collection optical fibers for collecting light scattered from the illuminated biological fluid.

In one embodiment, the source optical fiber is positioned in a center of the fiber array, and the collection optical fibers are positioned in one or more rings having a center at the source optical fiber such that each collection optical fiber is offset from the source optical fiber.

In one embodiment, the source optical fiber is surrounded by the collection optical fibers, so that a working end of the optical probe is formed by a ring of beveled collection fibers.

In one embodiment, the optical probe further comprises a ball lens operably placed at a distance from the working end to focus the beam of light on the biological fluid.

In one embodiment, the collection optical fibers are positioned in one or more rings having a center at the source optical fiber such that each collection optical fiber is offset from the source optical fiber.

In one embodiment, the source optical fiber is placed proximate to an edge of the optical probe.

In one embodiment, the optical probe further comprises LED fibers or other illumination source for determining placement information of the optical probe.

In one embodiment, the detector comprises a spectrometer. In one embodiment, the detector further comprises a charge-coupled device (CCD).

In yet another aspect, the invention relates to a method for characterizing contents of a bio-object. In one embodiment, the method includes illuminating the bio-object with a beam of light; obtaining Raman data from light scattered from the illuminated bio-object; and finding Raman signatures corresponding to biochemical compositions from the obtained Raman data, so as to identify and discriminate the contents of the bio-object from the Raman signatures.

In one embodiment, the bio-object comprises a middle ear fluid (MEF). In one embodiment, the contents of the bio-object comprise bacteria that cause acute otitis media (AOM). The bacteria comprise *H. influenzae, M. catarrh-*

*alis*, and/or *S. pneumoniae*. In addition, the MEF may contain other bacteria not included here. In another embodiment, the contents of the bio-object comprise *S. agalactiae, S. aureus*, and/or the like. In addition, the MEF may contain other bacteria not included here. The contents of the bio-object comprise methicillin-resistant *S. aureus* (MRSA).

In one embodiment, the illuminating step comprises illuminating the bio-object with the beam of light from a near-infrared light source.

In one embodiment, the obtaining step comprises collecting the scattered light with an optical probe and obtaining Raman spectra of the scattered light into with a spectrometer.

In one embodiment, the finding step comprises processing the obtained Raman spectra to find the Raman signatures corresponding to each type of bacteria.

In one embodiment, the processing step is performed with a sparse multinomial logistic regression (SMLR) algorithm.

In one embodiment, the finding step comprises comparing the obtained Raman spectra with a library that contains Raman spectral features of each type of bacteria to identify the Raman signatures corresponding to each type of bacteria.

In one embodiment, the Raman signatures comprise peaks and its corresponding wavelengths in the Raman spectra.

In a further aspect, the invention relates to a system for characterizing contents of a bio-object. In one embodiment, the system has an optical probe optically connected to a light source for emitting a beam of light and configured to deliver the beam of light emitted from the light source to the biological fluid and to collect light scattered from the illuminated bio-object; a detector optically coupled with the optical probe, for obtaining Raman data from the collected scattered light; and a controller in communication with the detector and programmed for finding Raman signatures corresponding to biochemical compositions from the obtained Raman data and identifying and discriminating the contents of the bio-object from the Raman signatures.

In one embodiment, the bio-object comprises a middle ear fluid (MEF). In one embodiment, the contents of the bio-object comprise bacteria that cause acute otitis media (AOM), where the bacteria comprise *H. influenzae, M. catarrhalis*, and/or *S. pneumoniae*. In another embodiment, the contents of the bio-object comprise *S. agalactiae, S. aureus*, and/or the like. In addition, the MEF may contain other bacteria not included here. The contents of the bio-object comprise methicillin-resistant *S. aureus* (MRSA).

In one embodiment, the light source comprises a laser or light emitting diodes (LEDs). In one embodiment, the beam of light has a wavelength in a near-infrared range.

In one embodiment, the optical probe has a working end, a source channel and a plurality of collection channels, wherein the working end is operably positioned proximate to a surface of the bio-object, the source channel is configured to deliver the beam of light emitted by the light source from the working end to the surface of the bio-object, and the collection channels are configured to collect from the working end light scattered from the illuminated bio-object.

In one embodiment, the optical probe comprises a plurality of optical fibers spatially arranged in a fiber array.

In one embodiment, at least one fiber of the plurality of optical fibers is a source optical fiber for delivering the beam of light emitted from the light source to the surface of the bio-object, and the remaining fibers of the plurality of optical fibers are collection optical fibers for collecting light scattered from the illuminated bio-object.

In one embodiment, the source optical fiber is positioned in a center of the fiber array, and the collection optical fibers are positioned in one or more rings having a center at the source optical fiber such that each collection optical fiber is offset from the source optical fiber.

In one embodiment, the source optical fiber is surrounded by the collection optical fibers, so that a working end of the optical probe is formed by a ring of beveled collection fibers.

In one embodiment, the optical probe further comprises a ball lens operably placed at a distance from the working end to focus the beam of light on the bio-object.

In one embodiment, the collection optical fibers are positioned in one or more rings having a center at the source optical fiber such that each collection optical fiber is offset from the source optical fiber.

In one embodiment, the source optical fiber is placed proximate to an edge of the optical probe.

In one embodiment, the optical probe further comprises LED fibers for determining placement information of the optical probe.

In one embodiment, the detector comprises a spectrometer. In one embodiment, the detector further comprises a charge-coupled device (CCD).

In one aspect, the invention relates to a method for characterizing middle ear fluid (MEF) to diagnose the AOM. One embodiment of the method involves analyzing samples of MEF using a vibrational spectroscopy technique called Raman spectroscopy. This technique provides a spectral signature of biochemical features or biomarkers of a sample. These biomarkers characterize the contents of the MEF. In certain embodiments, a spectral database of these biomarkers is built for statistical analysis to detect the presence and identification of bacteria in the MEF for diagnosis of the AOM. This approach can be applied to other biological fluids ex vivo or in vivo.

The AOM is the rapid onset of signs and symptoms, such as otalgia and fever, of acute infection within the middle ear. Current clinical methods to diagnose the AOM rely on subtle observational changes and effects of symptoms, which make it challenging. Furthermore, these methods do not investigate the source causing an infection since they do not detect the presence of or identify bacteria in the MEF.

According to the invention, the application of the RS to characterize the MEF and detect the presence of and identify bacteria in MEF for diagnosing the AOM can guide physicians to prescribe more targeted antibiotics if needed. This aids in reducing the number of multi-drug resistant organisms (MDROs). In addition, this method is also non-invasive, rapid, and portable in the clinical setting.

In certain embodiments, the RS is used to characterize the spectral signature of the three main bacteria that cause the AOM, *Haemophilus influenzae* (also notated as *H. influenzae*), *Moraxella catarrhalis* (also notated as *M. catarrhalis*), and *Streptococcus pneumoniae* (also notated as *S. pneumoniae*). Additionally, specific biomarkers have been statistically identified as important features to discriminate bacteria at the genus and species levels.

Exemplary examples include, but are not limited to, characterizing pure, mixed, mutant, and resistant strains of bacteria that cause the AOM in a fluid environment using the RS, analyzing biomarkers found in clinical MEF samples and comparing to pure bacterial features, and characterizing optical properties of tympanic membrane.

Among other things, the RS system is directly applicable to aiding physicians in differentiating between the two main types of otitis media (OM), in inflammatory disease of the middle ear. Otitis media with effusion (OME) is an inflammation of the middle ear with a buildup of fluid in the middle ear space and does not require antibiotic treatment. The AOM is caused by an acute bacterial infection. Therefore, by detecting the presence of bacteria one is able to determine the need for antibiotics. Identification of bacteria causing the AOM would aid in prescribing more targeted antibiotics to treat the infection. Ultimately this would improve patient outcomes and reduce the rise in MDROs.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
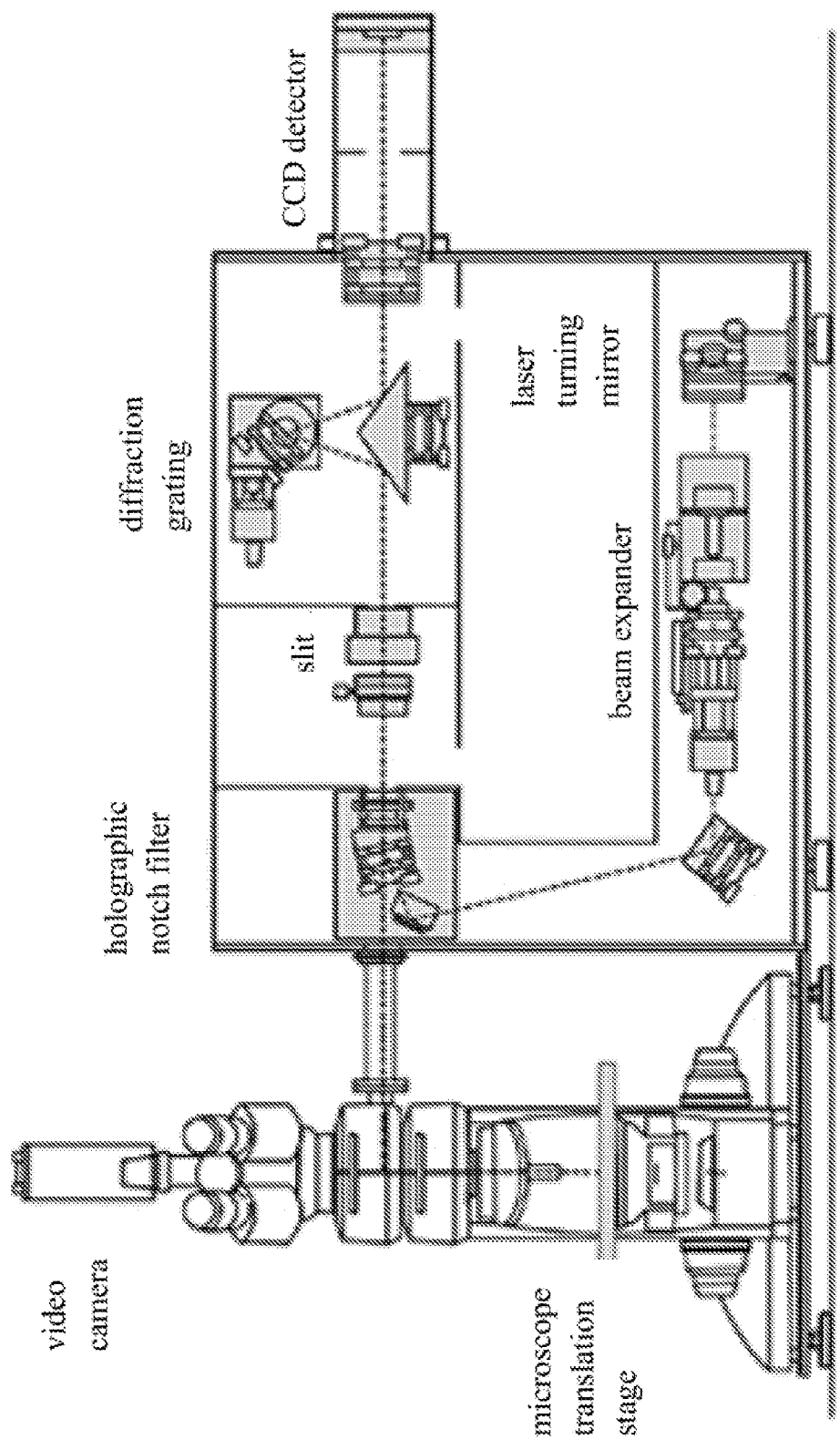
FIG. 1 shows a Renishaw inVia confocal Raman microscope.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It is appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It is understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It is understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It is understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It are also appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It is further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It is understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It is further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to methods and systems for identification of bacteria in a biological fluid using Raman spectroscopy and applications of the same.

Raman spectroscopy is able to non-invasively take real-time measurements of the biochemical composition of a sample by monitoring the interaction of laser light with the vibrational modes of the chemical bonds that compose the sample. The change in energy after the light interacts with the chemical makeup of the sample corresponds to specific molecular features such as lipids, DNA, and amides among other things. It is known that Gram-positive bacteria have a thicker cell wall composed of peptidoglycan compared to Gram-negative bacteria. Furthermore, variation in biochemical features such as carbohydrates, surface protein antigens, teichoic acids, and fatty acids that are attached to the cell wall are indicative of differences among bacteria type. In addition, the guanine-cytosine (G+C) content in DNA varies for each of the bacteria that cause AOM.

The three main bacteria that cause AOM, *Haemophilus influenzae* (also notated as *H. influenzae*, Gram-negative), *Moraxella catarrhalis* (also notated as *M. catarrhalis*, Gram-negative), and *Streptococcus pneumoniae* (also notated as *S. pneumoniae*, Gram-positive), are part of normal upper respiratory tract flora. However, under the right conditions these bacteria can thrive in middle ear effusion (MEE) and cause AOM.

One of the objectives of the invention is to use the RS to characterize and detect the presence of an active infection, classify multiple bacteria species and strains, and potentially improve diagnosis of AOM. The ability of the optical technique to non-invasively probe biochemical features provides valuable information about bacteria involved in AOM while minimizing discomfort to the patient. Applications of the technique have the potential to improve diagnostic accuracy of AOM in real-time, thereby providing physicians with the information needed to prescribe the most beneficial antibiotic for the patient and decrease the course of infection.

In one aspect, the invention relates to a method for identification and discrimination of bacteria and/or mutant and/or resistant bacterial strains in a biological fluid. In one embodiment, the method includes illuminating the biological fluid with a beam of light; obtaining Raman data from light scattered from the illuminated biological fluid; and finding Raman signatures corresponding to each type of bacteria and/or mutant bacterial strains from the obtained Raman data, so as to identify and discriminate each type of bacteria and/or mutant bacterial strains in the biological fluid from the Raman signatures. In one embodiment, the biological fluid comprises a middle ear fluid (MEF). In one embodiment, the bacteria that cause acute otitis media (AOM) in the biological fluid comprise *H. influenzae, M. catarrhalis*, and/or *S. pneumoniae*. In another embodiment, the bacteria comprise *S. agalactiae, S. aureus*, and/or the like. The mutant bacterial strains comprise methicillin-resistant *S. aureus* (MRSA).

In one embodiment, the illuminating step comprises illuminating the biological fluid with the beam of light from a near-infrared light source.

In one embodiment, the obtaining step comprises collecting the scattered light with an optical probe and obtaining Raman spectra of the scattered light into with a spectrometer.

In one embodiment, the finding step comprises processing the obtained Raman spectra to find the Raman signatures corresponding to each type of bacteria.

In one embodiment, the processing step is performed with a sparse multinomial logistic regression (SMLR) algorithm.

In one embodiment, the finding step comprises comparing the obtained Raman spectra with a library of biochemical features that contains Raman spectral features of each type of bacteria and/or mutant bacterial strains to identify and discriminate the Raman signatures corresponding to each type of bacteria and/or mutant bacterial strains.

In one embodiment, the Raman signatures comprise peaks and its corresponding wavelengths in the Raman spectra.

In another aspect, the invention relates to a system for identification and discrimination of bacteria and/or mutant bacterial strains in a biological fluid. In one embodiment, the system includes an optical probe optically connected to a light source for emitting a beam of light and configured to deliver the beam of light emitted from the light source to the biological fluid and to collect light scattered from the illuminated biological fluid; a detector optically coupled with the optical probe, for obtaining Raman data from the collected scattered light; and a controller in communication with the detector and programmed for finding Raman signatures corresponding to each type of bacteria and/or mutant bacterial strains from the obtained Raman data and identifying and discriminating each type of bacteria and/or mutant bacterial strains in the biological fluid from the Raman signatures. In one embodiment, the biological fluid comprises a middle ear fluid (MEF). In one embodiment, the bacteria that cause acute otitis media (AOM) in the biological fluid comprise *H. influenzae, M. catarrhalis*, and/or *S. pneumoniae*. In another embodiment, the bacteria comprise *S. agalactiae, S. aureus*, and/or the like. The mutant bacterial strains comprise methicillin-resistant *S. aureus* (MRSA).

In one embodiment, the light source comprises a laser or light emitting diodes (LEDs). In one embodiment, the beam of light has a wavelength in a near-infrared range.

In one embodiment, the optical probe has a working end, a source channel and a plurality of collection channels, wherein the working end is operably positioned proximate to a surface of the biological fluid, the source channel is configured to deliver the bean of light emitted by the light source from the working end to the surface of the biological fluid, and the collection channels are configured to collect from the working end light scattered from the illuminated biological fluid.

In one embodiment, the optical probe comprises a plurality of optical fibers spatially arranged in a fiber array.

In one embodiment, at least one fiber of the plurality of optical fibers is a source optical fiber for delivering the beam of light emitted from the light source to the surface of the biological fluid, and the remaining fibers of the plurality of optical fibers are collection optical fibers for collecting light scattered from the illuminated biological fluid.

In one embodiment, the source optical fiber is positioned in a center of the fiber array, and the collection optical fibers are positioned in one or more rings having a center at the source optical fiber such that each collection optical fiber is offset from the source optical fiber.

In one embodiment, the source optical fiber is surrounded by the collection optical fibers, so that a working end of the optical probe is formed by a ring of beveled collection fibers.

In one embodiment, the optical probe further comprises a ball lens operably placed at a distance from the working end to focus the beam of light on the biological fluid.

In one embodiment, the collection optical fibers are positioned in one or more rings having a center at the source optical fiber such that each collection optical fiber is offset from the source optical fiber.

In one embodiment, the source optical fiber is placed proximate to an edge of the optical probe.

In one embodiment, the optical probe further comprises LED fibers for determining placement information of the optical probe.

In one embodiment, the detector comprises a spectrometer. In one embodiment, the detector further comprises a charge-coupled device (CCD).

In yet another aspect, the invention relates to a method for characterizing contents of a bio-object. In one embodiment, the method includes illuminating the bio-object with a beam of light; obtaining Raman data from light scattered from the illuminated bio-object; and finding Raman signatures corresponding to biochemical compositions from the obtained Raman data, so as to identify and discriminate the contents of the bio-object from the Raman signatures.

In one embodiment, the bio-object comprises a middle ear fluid (MEF). In one embodiment, the contents of the bio-object comprise bacteria that cause acute otitis media (AOM). The bacteria comprise *H. influenzae, M. catarrhalis,* and/or *S. pneumoniae*. In another embodiment, the contents of the bio-object comprise *S. agalactiae, S. aureus,* and/or the like.

The contents of the bio-object comprise methicillin-resistant *S. aureus* (MRSA).

In one embodiment, the illuminating step comprises illuminating the bio-object with the beam of light from a near-infrared light source.

In one embodiment, the obtaining step comprises collecting the scattered light with an optical probe and obtaining Raman spectra of the scattered light into with a spectrometer.

In one embodiment, the finding step comprises processing the obtained Raman spectra to find the Raman signatures corresponding to each type of bacteria.

In one embodiment, the processing step is performed with a sparse multinomial logistic regression (SMLR) algorithm.

In one embodiment, the finding step comprises comparing the obtained Raman spectra with a library that contains Raman spectral features of each type of bacteria to identify the Raman signatures corresponding to each type of bacteria.

In one embodiment, the Raman signatures comprise peaks and its corresponding wavelengths in the Raman spectra.

In a further aspect, the invention relates to a system for characterizing contents of a bio-object. In one embodiment, the system has an optical probe optically connected to a light source for emitting a beam of light and configured to deliver the beam of light emitted from the light source to the biological fluid and to collect light scattered from the illuminated bio-object; a detector optically coupled with the optical probe, for obtaining Raman data from the collected scattered light; and a controller in communication with the detector and programmed for finding Raman signatures corresponding to biochemical compositions from the obtained Raman data and identifying and discriminating the contents of the bio-object from the Raman signatures.

In one embodiment, the bio-object comprises a middle ear fluid (MEF). In one embodiment, the contents of the bio-object comprise bacteria that cause acute otitis media (AOM), where the bacteria comprise *H. influenzae, M. catarrhalis,* and/or *S. pneumoniae*. In another embodiment, the contents of the bio-object comprise *S. agalactiae, S. aureus,* and/or the like. The contents of the bio-object comprise methicillin-resistant *S. aureus* (MRSA).

In one embodiment, the light source comprises a laser or light emitting diodes (LEDs). In one embodiment, the beam of light has a wavelength in a near-infrared range.

In one embodiment, the optical probe has a working end, a source channel and a plurality of collection channels, wherein the working end is operably positioned proximate to a surface of the bio-object, the source channel is configured to deliver the bean of light emitted by the light source from the working end to the surface of the bio-object, and the collection channels are configured to collect from the working end light scattered from the illuminated bio-object.

In one embodiment, the optical probe comprises a plurality of optical fibers spatially arranged in a fiber array.

In one embodiment, at least one fiber of the plurality of optical fibers is a source optical fiber for delivering the beam of light emitted from the light source to the surface of the bio-object, and the remaining fibers of the plurality of optical fibers are collection optical fibers for collecting light scattered from the illuminated bio-object.

In one embodiment, the source optical fiber is positioned in a center of the fiber array, and the collection optical fibers are positioned in one or more rings having a center at the source optical fiber such that each collection optical fiber is offset from the source optical fiber.

In one embodiment, the source optical fiber is surrounded by the collection optical fibers, so that a working end of the optical probe is formed by a ring of beveled collection fibers.

In one embodiment, the optical probe further comprises a ball lens operably placed at a distance from the working end to focus the beam of light on the bio-object.

In one embodiment, the collection optical fibers are positioned in one or more rings having a center at the source optical fiber such that each collection optical fiber is offset from the source optical fiber.

In one embodiment, the source optical fiber is placed proximate to an edge of the optical probe.

In one embodiment, the optical probe further comprises LED fibers for determining placement information of the optical probe.

In one embodiment, the detector comprises a spectrometer. In one embodiment, the detector further comprises a charge-coupled device (CCD).

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

Example 1

Spectral Features of Bacteria that Cause AOM

The three most common bacteria that cause AOM (*H. influenzae, M. catarrhalis,* and *S. pneumoniae*) are acquired commercially and grown separately in vitro on Mueller-Hinton (MH) agar plates and characterized using confocal Raman microscopy (RM), which provides high spatial and spectral resolution. Both live and dead forms of each bacterium are prepared in vitro to simulate an active and inactive infection, respectively. Raman spectra are collected from multiple bacterial colonies for each bacterium. A statistical model is developed to determine biochemical features that are important in distinguishing each bacterium and viability.

In certain embodiments, the spectral profiles of each of the three main bacteria that cause AOM are collected and characterized to test the ability of Raman microscopy to probe the biochemical features for each of the bacteria. These spectral fingerprints are input into a multinomial logistic regression model and then used to calculate spectral features that are important in classifying each bacterium. Since it is also clinically relevant to distinguish between an active versus an inactive state of infection, both live and dead forms of bacteria are prepared and analyzed to determine spectral differences for each. Spectral features that are important for classification are determined, and both between bacteria and live versus dead forms are referenced for multi-component spectral analysis. A library of important biochemical features for more rare bacteria involved in causing AOM is also be compiled using this approach.

Selection of Agar Growth Media:

Multiple agar types are tested and compared for optimal growth of the three main otopathogens that cause AOM and for minimal spectral interference within the Raman fingerprint region (700-1800 $cm^{-1}$). Chocolate agar (Thermo Fisher Scientific, Waltham, Mass.), the color of which is derived from lysed red blood cells (RBCs), is used primarily to grow the fastidious organism *H. influenzae*. However, this agar is also capable of growing *M. catarrhalis* and *S. pneumoniae*. More commonly used agar types for bacterial growth include tryptic soy agar (TSA), Luria-Bertani (LB) agar, and Mueller-Hinton (MH) agar.

TSA (Becton Dickinson (BD), Franklin Lakes, N.J.) is composed of pancreatic digest of casein (15 g), papaic digest of soybean (5 g), sodium chloride (5 g), and agar (15 g). TSA is prepared by suspending 40 g of the powder in 1 L of distilled water in a flask and mixed thoroughly. The flask is placed on a hot plate and heated with frequent agitation and boiled for 1 minute until the powder completely dissolves. A final pH is set to 7.3±0.2. The flask is then autoclaved at 121° C. for 15 minutes. The autoclaved flask is agitated to allow cooling for 3 minutes then poured into labeled petri dishes. Once cooled and dried, plates are placed in the cold room (4° C.) and checked for any visual contamination before use. LB agar (BD, Franklin Lakes, N.J.) is composed of tryptone (10 g), yeast extract (5 g), sodium chloride (10 g), and agar (15 g). LB agar is prepared by suspending 40 g of the powder in 1 L of distilled water and mixed thoroughly. The agar medium is heated with frequent agitation and boiled for 1 minute to completely dissolve the powder. A final pH of 7.0±0.2 is set. MH agar (BD, Franklin Lakes, N.J.) is made of beef extract (3 g), acid hydrolysate of casein (17.5 g), and starch (1.5 g). MH agar is prepared by suspending 11 g of MH powder and 7.5 g (15% agar/L) of agar (Thermo Fisher Scientific, Waltham, Mass.) in 500 mL of distilled water while heating (180° F.) and stirring. A final pH is set to 7.3±0.1. The mixture is then autoclaved at 121° C. for 10 minutes. The autoclaved flask is agitated to allow cooling for 3 minutes then poured into labeled petri dishes. Once cooled and dried, plates is placed in the cold room (4° C.) and checked for any visual contamination before use. MH agar is a non-selective, non-differential microbiological growth medium that contains basic nutrients and no additives, and therefore a minimal Raman signal from the MH agar. Since MH agar does not contain lysed RBCs for growth of *H. influenzae*, factors X (Hemin) and V (Nicotinamide adenine dinucleotide (NAD)) are added with sterile techniques using disks from Hardy Diagnostics, Santa Maria, Calif.

Agar with Bacteria:

*H. influenzae* (Gram-negative, ATCC No. 49766), *M. catarrhalis* (Gram-negative, ATCC No. 49143), and *S. pneumoniae* (Gram-positive, ATCC No. 6301) strains is purchased from ATCC (Manassas, Va.). Propagation methods as recommended by ATCC are used for each strain in preparation for culturing the bacteria and are performed on the agar types mentioned above.

Model and Testing for Inactive Bacteria:

The three main bacteria that cause AOM is cultured as described. After incubation, UV light at 254 nm is used to irradiate the agar plates with bacteria. Multiple time increments is tested to identify efficient cell death and verified with standard assays. After UV exposure, multiple bacterial colonies are collected for a serial dilution using phosphate-buffered saline (PBS) solution to quantify cellular death. This is compared with non-UV irradiated bacterial colonies. BSL-1 bacteria such as *S. aureus* and *E. coli* are also tested with UV light. It is expected that UV light damages nucleic acids and disrupt cell wall formation and molecular processes.

Raman Microspectroscopy of Bacteria:

An inVia confocal Raman microscope (Renishaw plc, Gloucestershire, UK) with 785 nm excitation is used to probe the bacteria on agar (FIG. 1). The Renishaw system has 5×, 20×, 50×, and 100× fluorescence minimizing objectives. The collected light from the sample is dispersed by a 1200 lines/mm grating (about 1 $cm^{-1}$ spectral dispersion) onto a deep-depleted (1024×256 pixel) 1" CCD (charge-coupled device).

Agar plates with bacteria is placed under the objective of a Leica DM2700M microscope on a Renishaw motorized stage and focused on a bacterial colony using the excitation source. The system has a depth resolution of about 1 μm and a 250 nm spatial resolution. Measurement parameters are determined based on optimizing signal to noise ratio (SNR) and minimizing fluorescence contribution. Raman measurements are collected from multiple spots on each colony and multiple colonies from each bacterium to determine intra-colony and intra-bacteria variability. Raman spectra from both live and dead forms of bacteria are collected using this approach.

Sample Size Estimation:

A standard sample size calculation is used to estimate the number of bacteria samples needed. The sample size (n) needed is calculated using the following formula:

$$n = \frac{(\sigma_1^2 + \sigma_2^2)(z_{1-\alpha/2} + z_{1-\beta})^2}{\Delta^2} \quad (1)$$

where a is the significance level ($\alpha$=0.05), $\beta$ is the probability not to correctly reject the null hypothesis when the alternative hypothesis is true ($\beta$=0.2), z statistic assuming an $\alpha$=0.05 ($z_{(1-\alpha/2)}$=1.96), z-statistic for assuming B a power of 80% ($z_{(1-\beta)}$=0.84), A is the difference between the means, which was based on previously collected data ($\Delta$=0.17 a.u.), and a is the standard deviation ($\sigma_1$=0.09 a.u. and $\sigma_2$=0.11 a.u.). The power of this study is (1–$\beta$)=0.80. Using these values, the sample size (n) calculates to 5.4507. Therefore, estimated 6 plates are needed for each type of bacteria.

Data Analysis:

Raman spectra collected from live and dead bacteria are fluorescence subtracted using a modified polynomial fitting method developed in the Mahadevan-Jansen lab and mean normalized for comparison. Multivariate statistical methods are used to classify the three main bacteria of interest and distinguish live versus dead bacteria based on biochemical features. A possible statistical model to implement is sparse multinomial logistic regression (SMLR). This SMLR model outputs weights and features for each biochemical feature that is determined to be important in classification. These values are then used to identify peaks that are most important in discriminating each bacteria type using an SMLR feature importance calculation.

Figure 2:
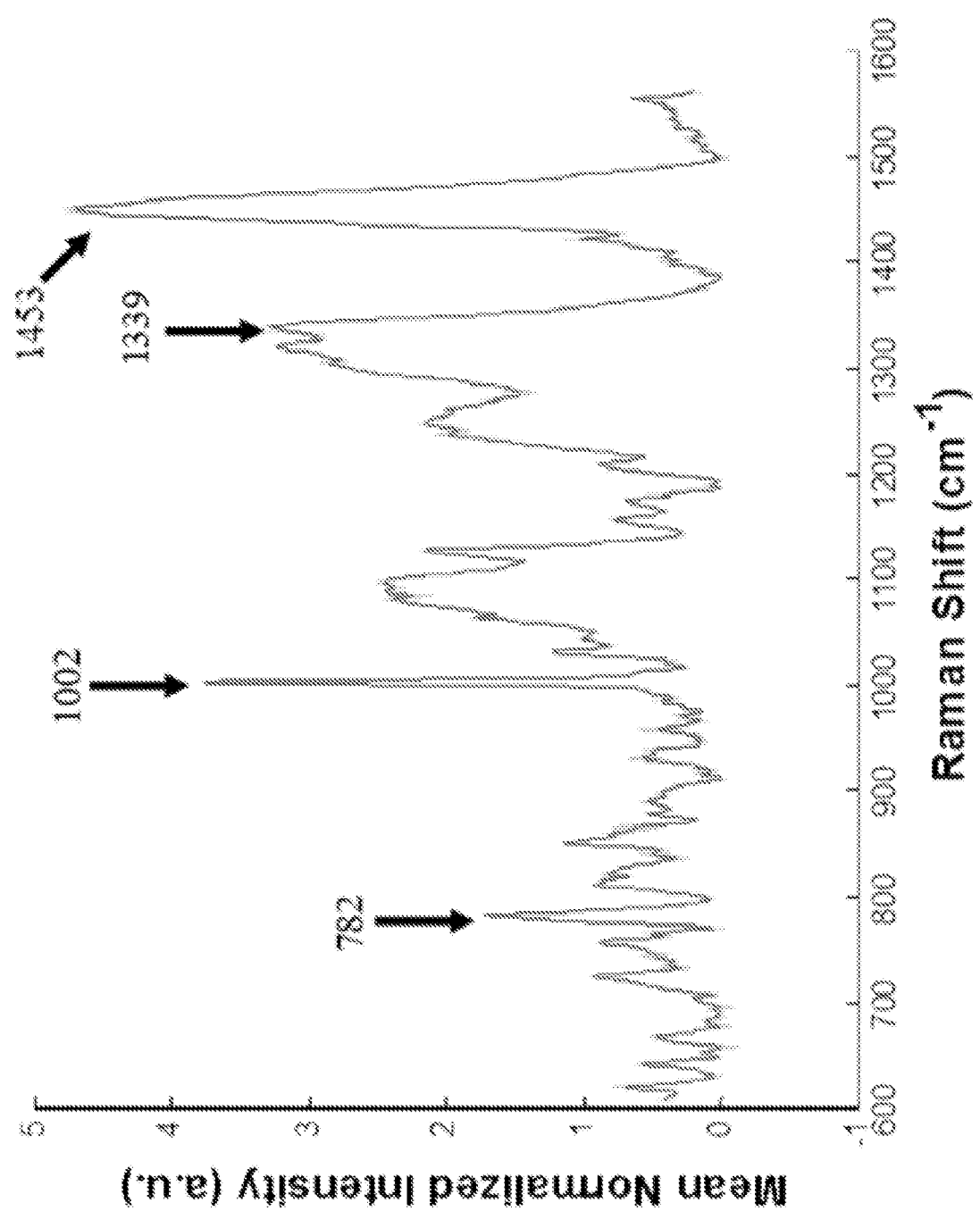
FIG. 2 shows mean±standard deviation Raman spectra of *E. coli* grown on MH agar according to one embodiment of the invention.
Figure 3:
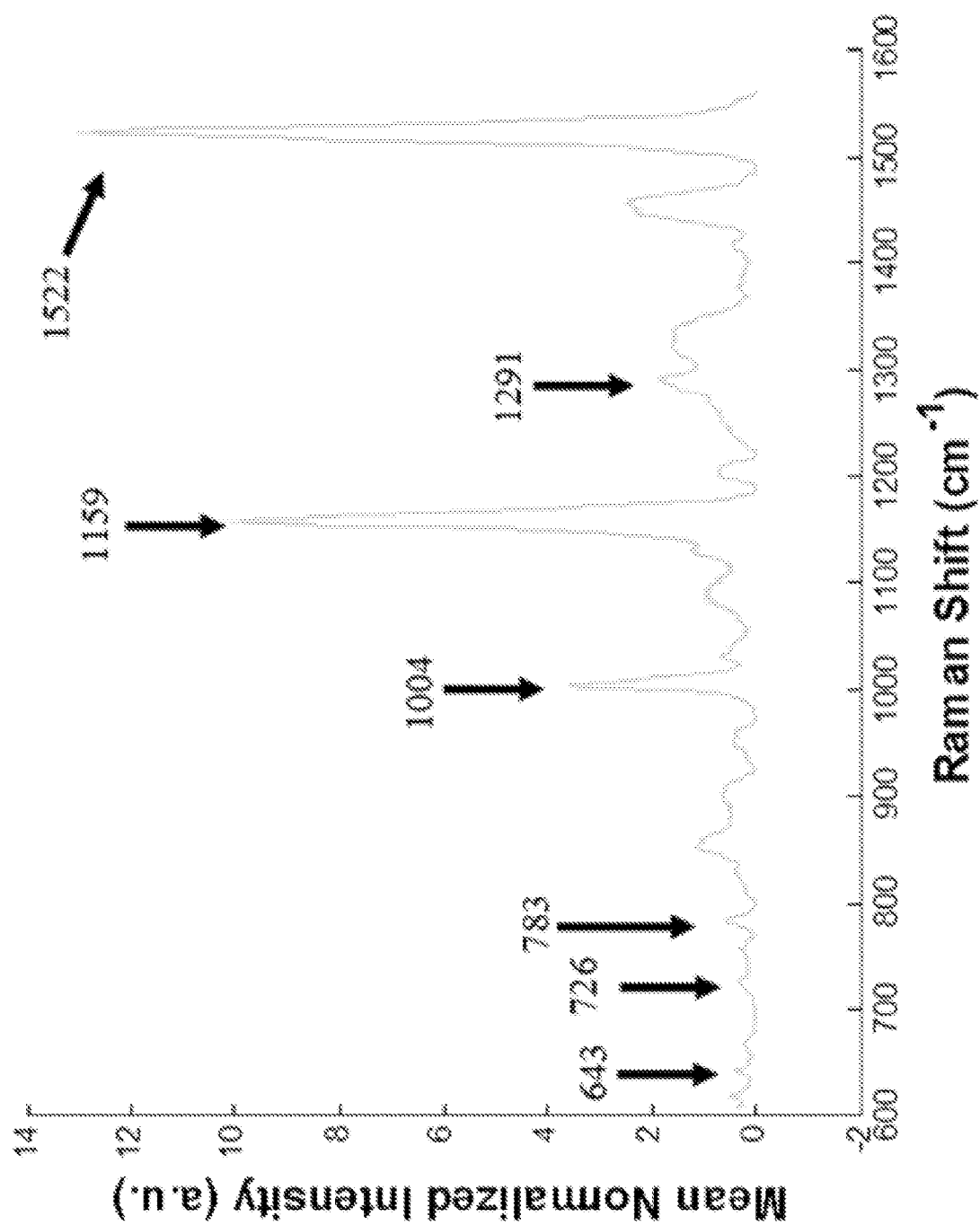
FIG. 3 shows mean±standard deviation Raman spectra of *S. aureus* grown on MH agar according to one embodiment of the invention.

Initial Studies on Bacteria of E. coli and S. aureus:

Escherichia coli (also notated as E. coli, Gram-negative) and Staphylococcus aureus (also notated as S. aureus, Gram-positive) were both cultured on Mueller-Hinton agar for a 21 hour incubation period at 37° C. No preparation was needed for Raman microspectroscopy as the experiment was setup to perform analysis directly on the bacterial colonies on the MH agar. A 785 nm excitation was used with a 100×/0.85 NA objective to focus a 1 μm spot diameter on a bacterial colony. A 15 second exposure with 5 accumulations and 20 second photobleach were set as the acquisition parameters. The power at the sample was –27 mW. Raman spectra of E. coli presented previously reported peaks at 782 cm$^{-1}$ (cytosine, uracil (ring stretching)), 1002 cm$^{-1}$ (phenylalanine), 1339 cm$^{-1}$ (adenine), 1453 cm$^{-1}$ ($CH_2$ and $CH_3$ deformations—lipids and proteins) (FIG. 2). Raman spectra were mean normalized by using the intensity at each wavenumber and dividing it by the mean intensity of the entire spectrum. Raman data of S. aureus was collected using the same acquisition parameter as that for E. coli (FIG. 3). Notable Raman peaks include 643 cm$^{-1}$ (tyrosine), 726 cm$^{-1}$ (peptidoglycan), 783 cm$^{-1}$ (cytosine, uracil (ring stretching)), 1004 cm$^{-1}$ (phenylalanine). S. aureus can be identified by three major carotenoid Raman peaks that correspond to staphyloxanthin, which provide the gold pigmentation on the bacterial colonies at 1159 cm$^{-1}$, 1291 cm$^{-1}$, and 1522 cm$^{-1}$.

Figure 4:
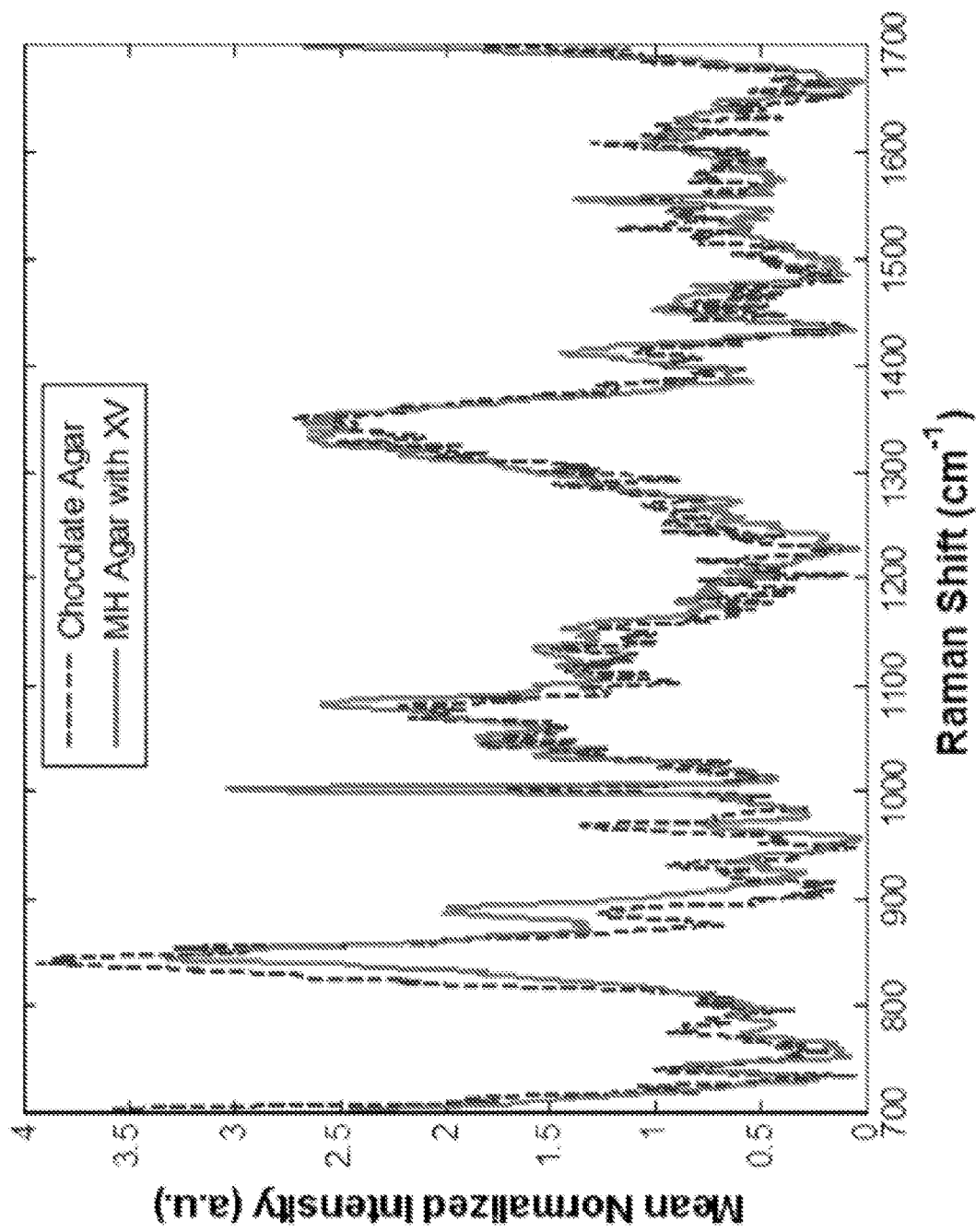
FIG. 4 shows mean Raman spectra of chocolate agar and Mueller-Hinton agar with added XV (Hemin and NAD) factors according to one embodiment of the invention.
Figure 5:
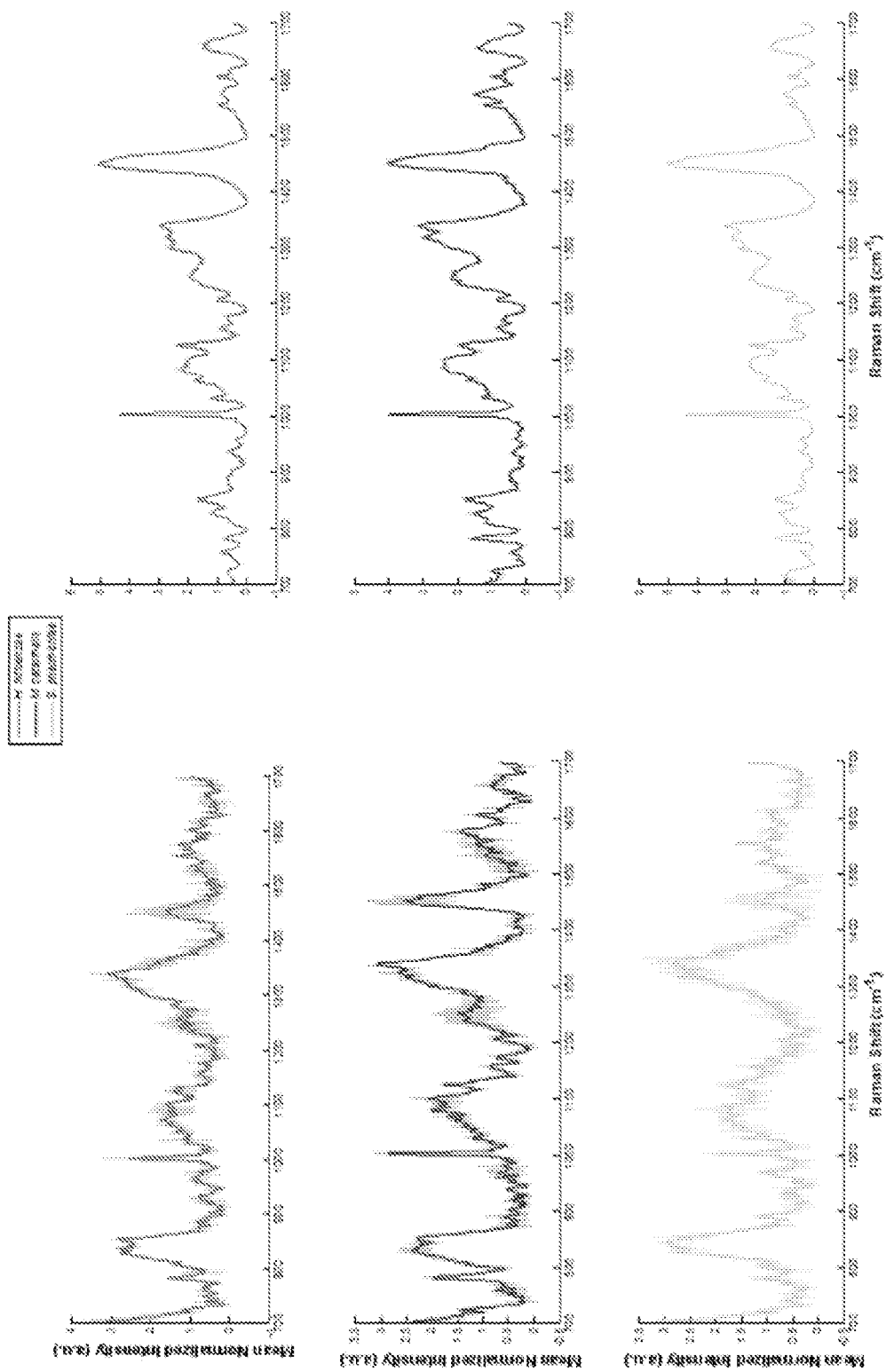
FIG. 5 shows mean±standard deviation Raman spectra of bacteria that cause AOM grown on chocolate agar (A-C) and MH agar (D-F) according to one embodiment of the invention. A 10× reduction in noise in MH agar compared to chocolate agar was calculated by using the standard deviation of the mean normalized intensity between 1500 $cm^{-1}$ and 1504 $cm^{-1}$.

Selection of Agar Type:

The first objective before evaluating Raman signatures of bacteria was to identify which type of culture agar would have minimal Raman contribution in the wavenumber region of interest (700-1800 cm$^{-1}$) while having the least amount of background noise. Therefore, it is compared to chocolate agar, the most common agar type to grow H. influenzae, and Mueller-Hinton (MH) agar while adding factors X (Hemin) and V (NAD), which are required for growth of H. influenzae (FIG. 4). The other two main bacteria that cause AOM are able to grow on both types of agar. Agar peaks from both agar types were identified as 740 cm$^{-1}$ (CC skeletal deformation-galactose ring), 844 cm$^{-1}$ (CC deformation/OCO wagging/CH vibrations with C—OH), 886 cm$^{-1}$ (CCH deformation), 969 cm$^{-1}$ (CCH deformation), 1082 cm$^{-1}$ (COH deformation/CCO stretching), and 1413 cm$^{-1}$ (CH deformation). H. influenzae, M. catarrhalis, and S. pneumoniae were grown individually on chocolate agar and MH agar (with XV factors) (FIG. 5).

An inVia confocal Raman microscope with a 100×/0.85 objective was used to focus 785 nm excitation. A 1 μm spot diameter was created by focusing the laser on the bacterial colony for each measurement. Acquisition settings included a 15 second exposure with 7 accumulations and a 30 second photobleach (to reduce fluorescence) for each measurement. For each bacteria type, 3 colonies were investigated with 3 spots per colony and 3 acquisitions per spot were evaluated. Bacterial colonies had a thickness about 400 μm, therefore an about 1 μm$^3$ volume from the laser would be able to interrogate the bacteria in the colony while minimizing agar signal contribution. A 10× reduction in noise in MH agar compared to chocolate agar was calculated by using the standard deviation of the mean normalized intensity between 1500 cm$^{-1}$ and 1504 cm$^{-1}$, which is an ideal range to investigate noise fluctuation since it does not contain Raman signal. This decrease in noise seen in MH agar allows for Raman bacterial peaks to become more visible.

Raman Spectral Profile of Bacteria Causing AOM.

Figure 6:
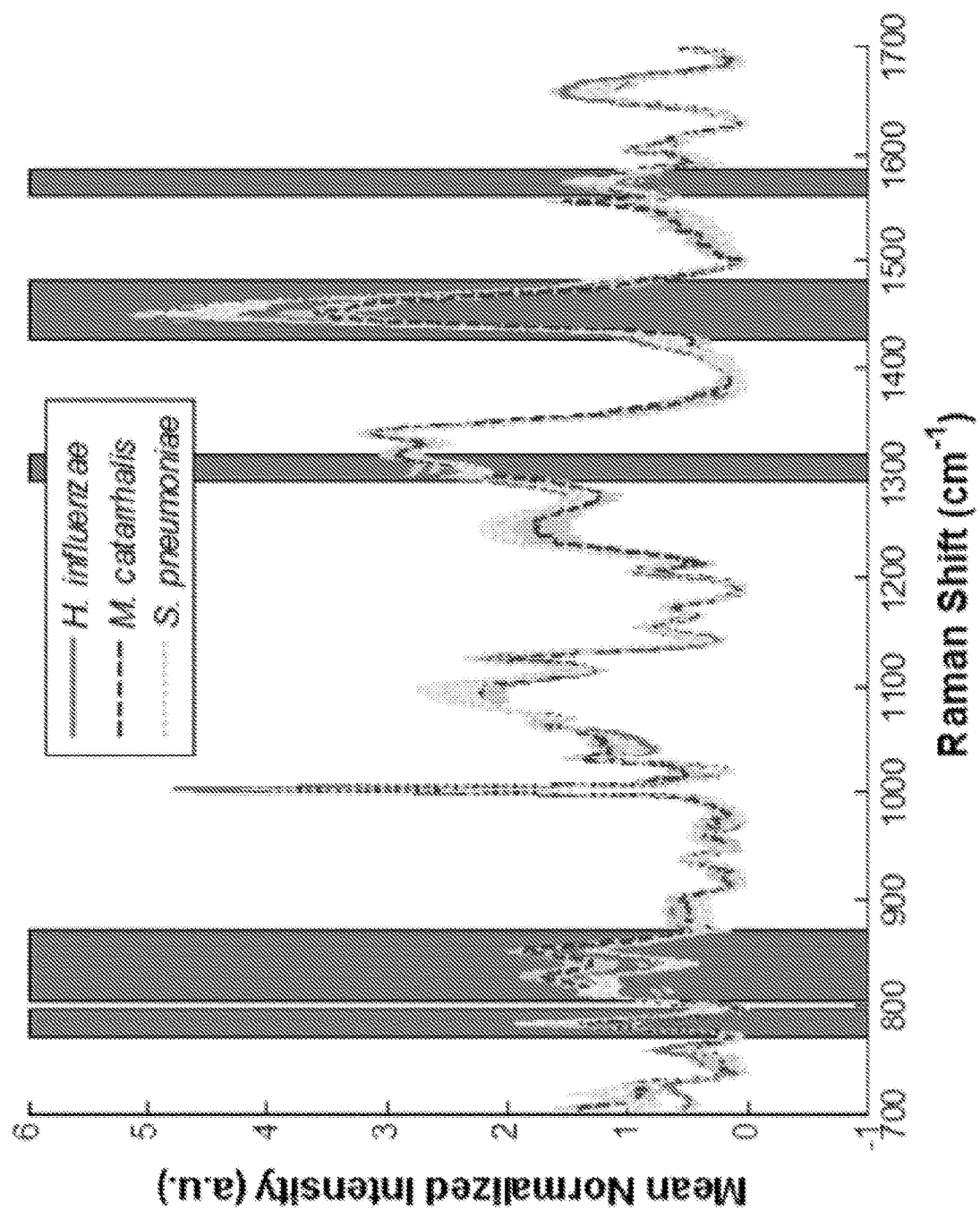
FIG. 6 shows mean±standard deviation Raman spectra of bacteria that cause AOM grown on MH agar according to one embodiment of the invention. Gray bands represent areas of interest for possible classification of each bacterium.

MH agar was selected as the agar of choice to use for growing bacteria that cause AOM based on its minimal interference in the fingerprint region (700-1800 cm$^{-1}$) and reduction in noise compared to chocolate agar. Furthermore, MH agar is a non-selective, non-differential microbiological growth medium that contains basic nutrients and no additives, minimizing Raman signal from the growth agar itself. Next, it is evaluated that Raman spectra from the three main bacteria that cause AOM to identify possible biochemical features that may be important in classifying these bacteria (FIG. 6). Possible biochemical features of interest include cytosine and uracil (ring stretching) at 783 cm$^{-1}$, tyrosine at 828 cm$^{-1}$, tryptophan and exopolysaccharides at 1555 cm$^{-1}$, and adenine, guanine (ring stretching), C—O vibration modes of peptidoglycan at 1574 cm$^{-1}$. These Raman peaks are highlighted in gray in FIG. 6. These features were visibly identified and are tested using a statistical model to identify Raman markers that are important for discrimination.

Figure 7:
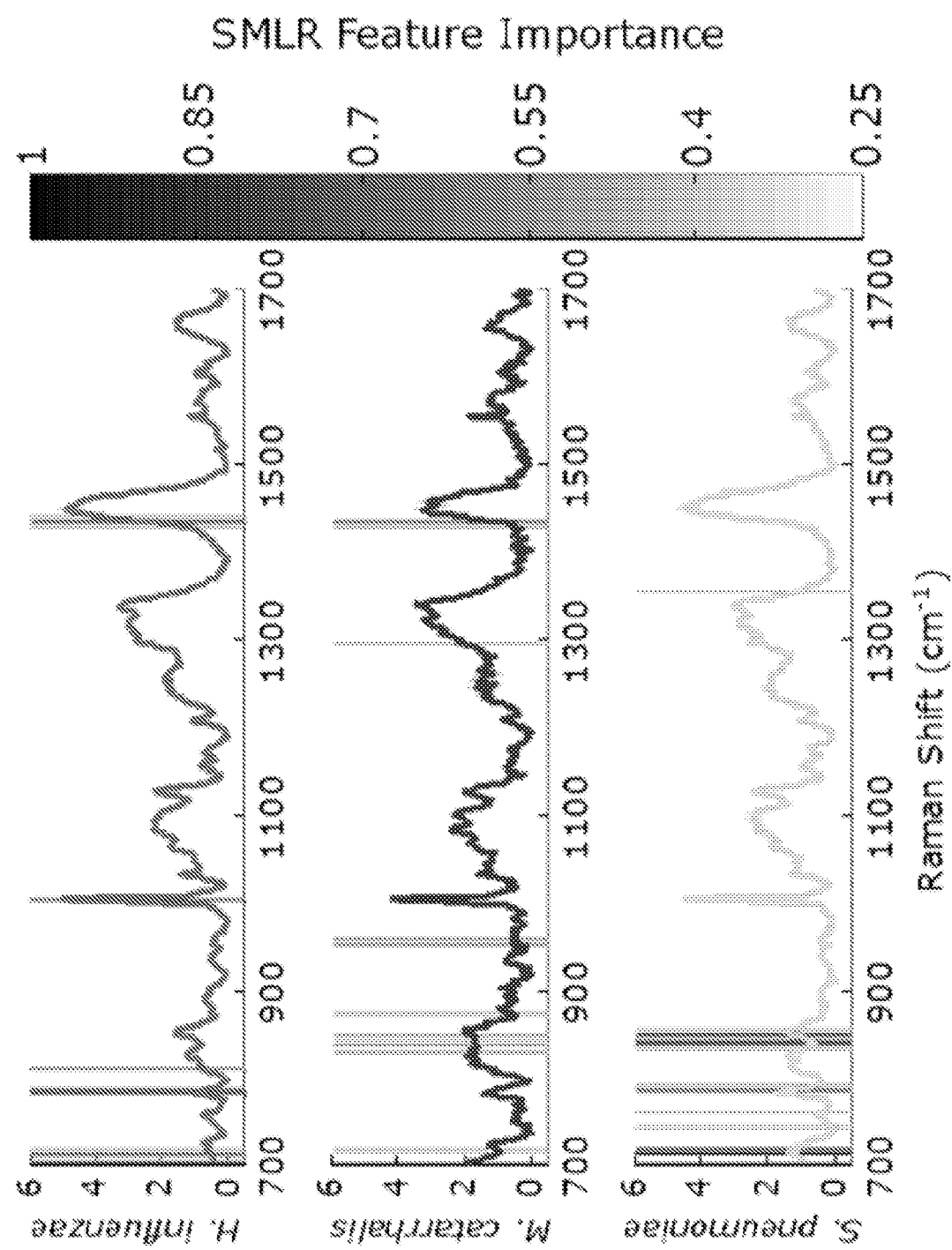
FIG. 7 shows mean±standard deviation Raman spectra of *H. influenzae, M. catarrhalis*, and *S. pneumoniae* grown on MH agar according to one embodiment of the invention. Gray bands represent spectral features used for SMLR classification of each bacteria type by using a sparsity value (X=0.1) for the SMLR input. The band gradient was based on SMLR feature importance.

SMLR Analysis and Posterior Probability:

A sparse multinomial logistic regression (SMLR) algorithm was used to identify biochemical features that are important in classifying H. influenzae, M. catarrhalis, and S. pneumoniae based on the in vitro experiments. This statistical method uses a logistic regression to produce specific weights and frequencies for biochemical features that are important in classification of each bacteria based on a training data set. It then uses these quantities to classify a multiclass system. Since there may have been features that were used rarely, but had large weights in addition to features that were used frequently, but had small weights, one needs to determine which features are indeed truly important in classifying the bacteria. Therefore, a new criteria is defined to determine SMLR feature importance based on scaling each feature frequency and weight determined between [0, 1] and calculating their product also on a scale of [0, 1]. By adjusting how many features would be used for classification in the SMLR model ($\lambda$, sparsity), the risk of over fitting is minimized. SMLR feature importance for *H. influenzae, M. catarrhalis,* and *S. pneumoniae* grown in MH agar are calculated using 400 features (FIG. 7).

Figure 8:
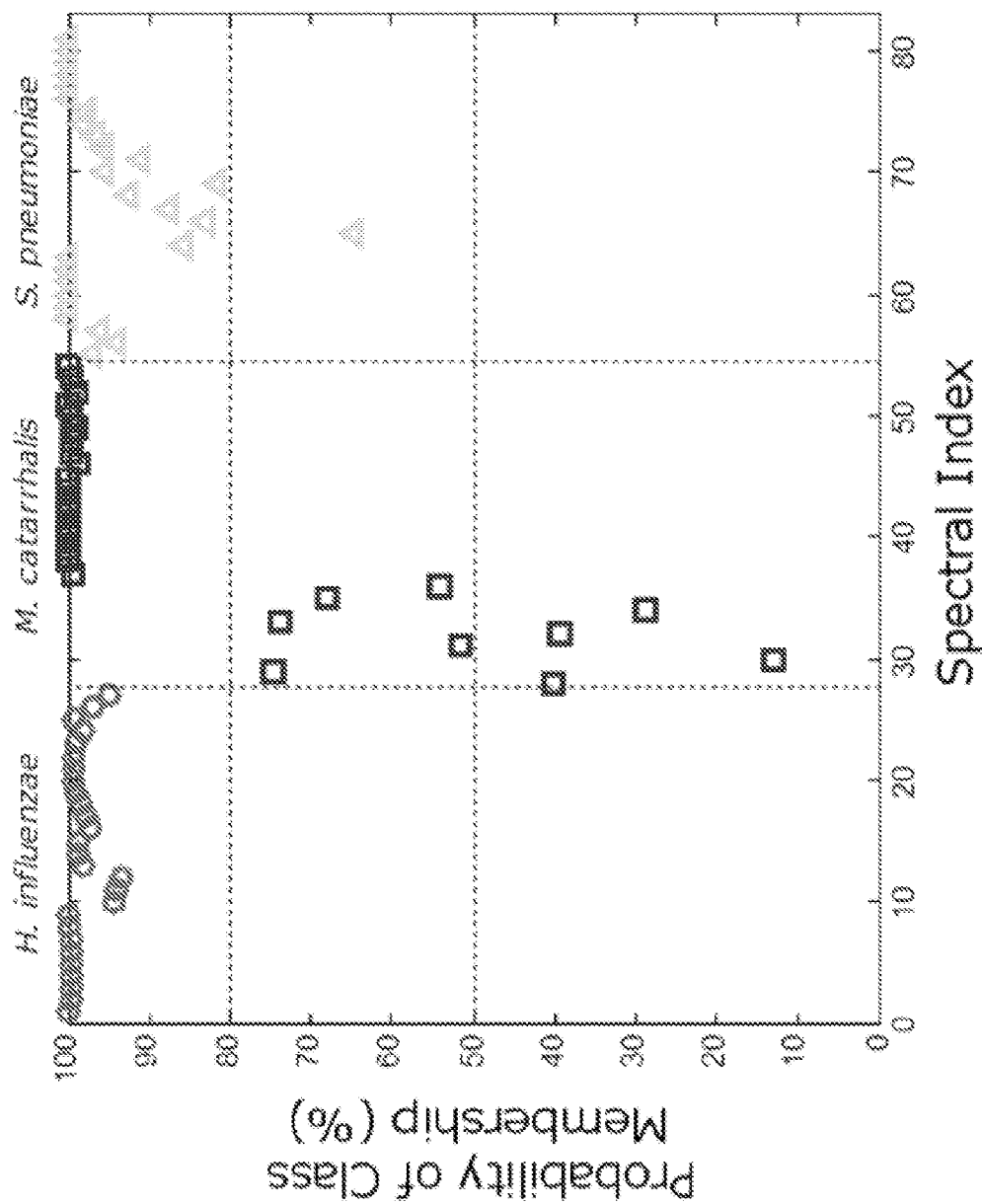
FIG. 8 shows a posterior probability plot based on the SMLR algorithm for each bacteria using 400 features (X=0.1) according to one embodiment of the invention.

In one embodiment, the total number of features evaluated was 917. The gray scale on FIG. 7 represents the level of importance of the specific wavenumber (biochemical feature) that was used for discriminating each bacteria type. The posterior probability of this classification used 400 features to determine classification for each bacteria type (FIG. 8). The classification analysis was based on using a k-fold cross-validation approach which separates the original data into k equally sized partitions called subsamples. Then, one of the k subsamples is retained and used to test the model while the remaining k−1 subsamples are utilized as the training data set. A 9-fold cross-validation is used, which in this data set translates to classifying a colony into a bacteria type and would more accurately estimate a predictive model.

The classification results, listed in Table 1, and the sensitivity and specificity for using 400 features to classify the different bacteria types were calculated using a 50% threshold for classification of each bacteria type, listed in Table 2.

TABLE 1

Classification for *H. influenzae, M. catarrhalis,* and *S. pneumoniae* based on the SMLR algorithm for each bacteria using 400 features ($\lambda$ = 0.1).

| $\lambda$ = 0.1, 50% Threshold | *H. influenzae* | *M. catarrhalis* | *S. pneumoniae* |
|---|---|---|---|
| *H. influenzae* | 27 | 0 | 0 |
| *M. catarrhalis* | 0 | 23 | 4 |
| *S. pneumoniae* | 0 | 0 | 27 |

TABLE 2

Sensitivity and specificity for each bacteria type using 400 features from SMLR ($\lambda$ = 0.1).

| $\lambda$ = 0.1, 50% Threshold | Sensitivity | Specificity |
|---|---|---|
| *H. influenzae* | 100% | 100% |
| *M. catarrhalis* | 85% | 100% |
| *S. pneumoniae* | 100% | 85% |

Figure 9:
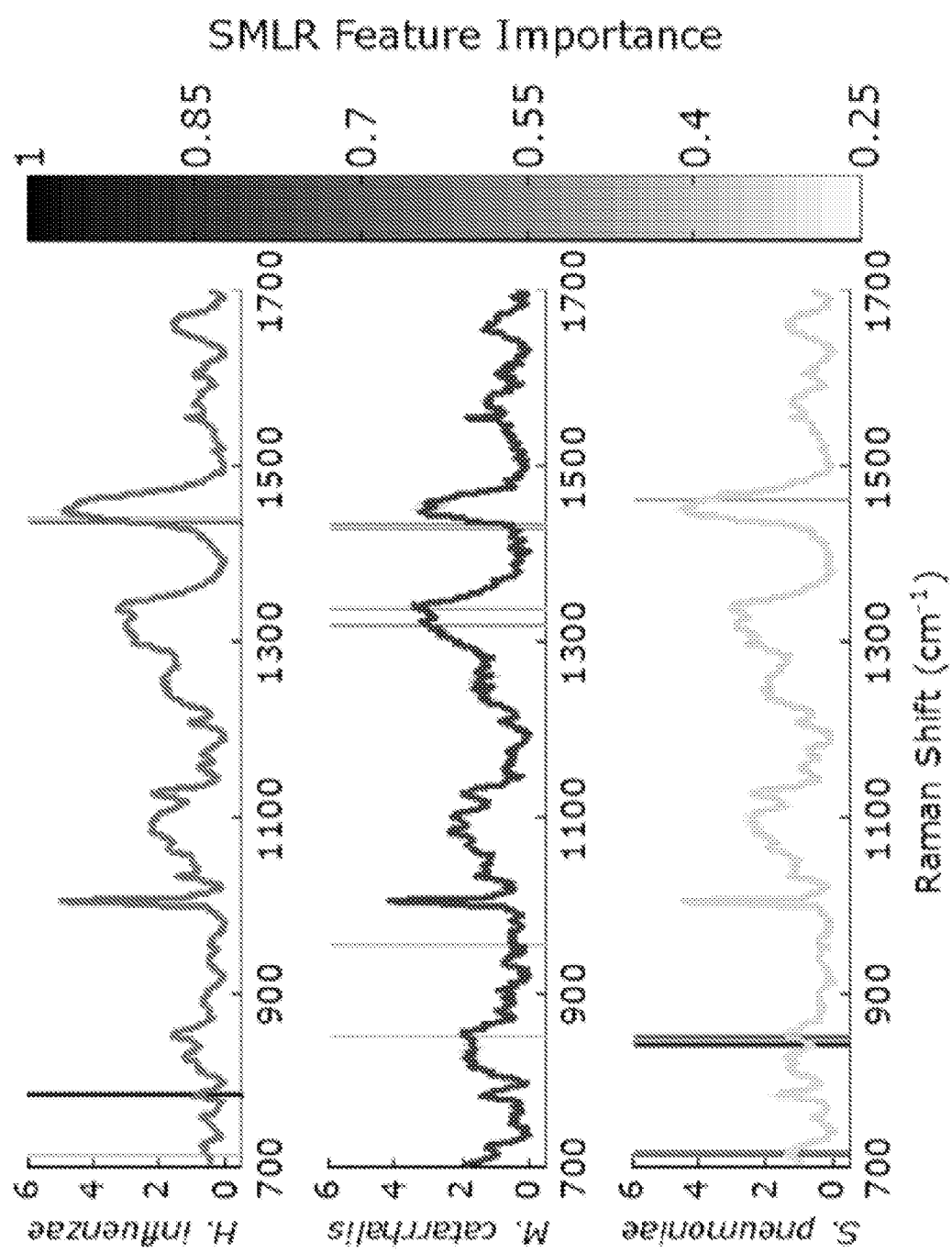
FIG. 9 shows mean±standard deviation Raman spectra of *H. influenzae, M. catarrhalis*, and *S. pneumoniae* grown on MH agar according to one embodiment of the invention. Gray bands represent spectral features used for SMLR classification of each bacteria type by using a sparsity value (X=1.0) for the SMLR input. The band gradient was based on SMLR feature importance.

For further analysis to see the effects on correctly classifying the different types of bacteria based on reducing the number of features used for classification, 77 features (X=1.0) are used to identify the most important spectral features to discriminate the bacteria type as seen by the gradient of the gray bands (FIG. 9).

Figure 10:
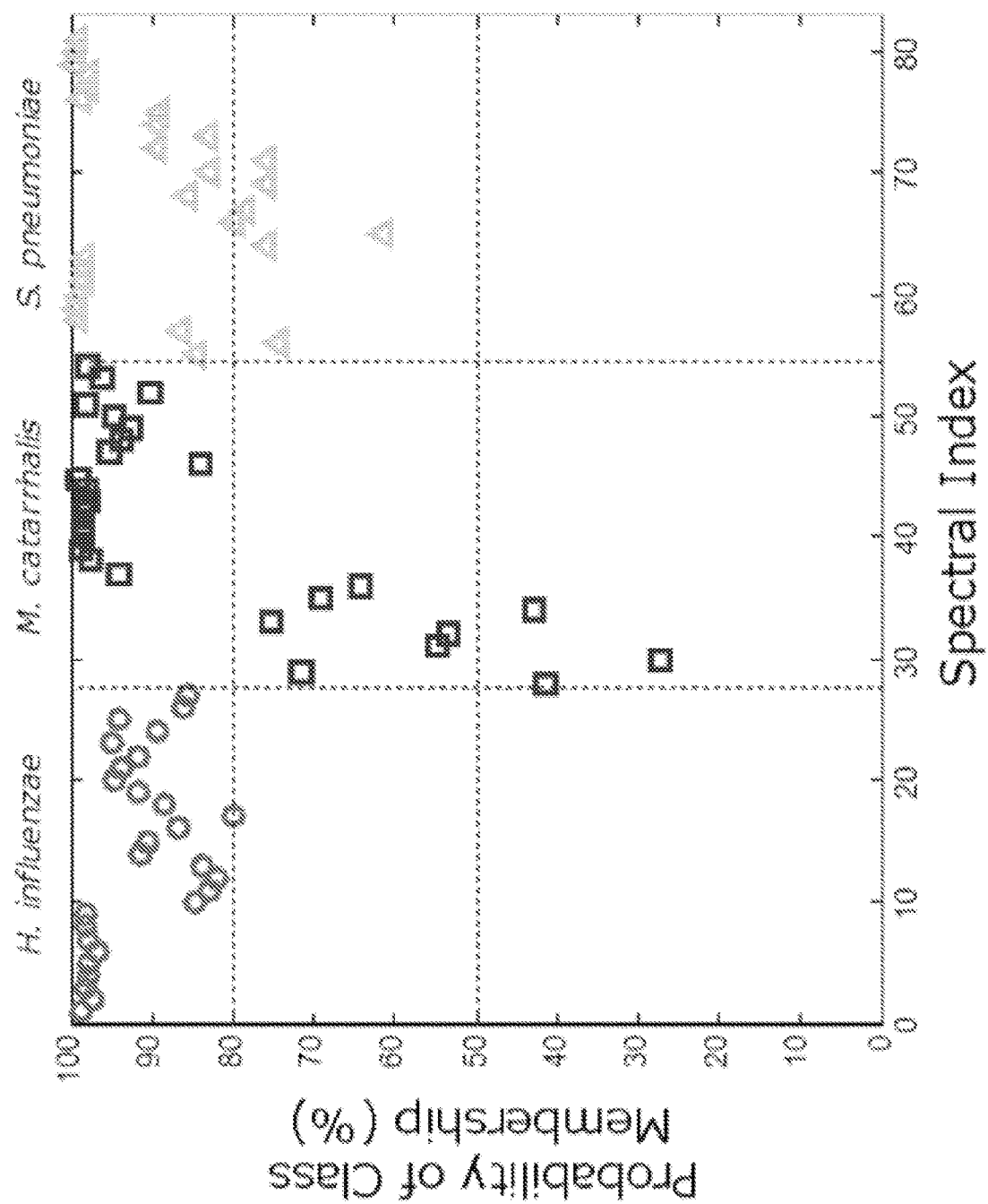
FIG. 10 shows a posterior probability plot based on the SMLR algorithm for each bacteria using 77 features (X=1.0) according to one embodiment of the invention.

The posterior probability is also calculated to determine the percent correctly classified for each bacteria type (FIG. 10). A 9-fold cross-validation is used, which in this data set translates to classifying a colony into bacteria. The classification results, listed in Table 3, and the sensitivity and specificity were calculated using a 50% threshold for classification of each bacteria type, listed in Table 4. Using 77 features achieved a higher classification of 89% compared to 85% from using 400 features.

TABLE 3

Classification for *H. influenzae, M. catarrhalis,* and *S. pneumoniae* based on the SMLR algorithm for each bacteria using 77 features ($\lambda$ = 1.0).

| $\lambda$ = 1.0, 50% Threshold | *H. influenzae* | *M. catarrhalis* | *S. pneumoniae* |
|---|---|---|---|
| *H. influenzae* | 27 | 0 | 0 |
| *M. catarrhalis* | 0 | 24 | 3 |
| *S. pneumoniae* | 0 | 0 | 27 |

TABLE 4

Sensitivity and specificity for each bacteria type using 77 features from SMLR ($\lambda$ = 1.0).

| $\lambda$ = 1.0, 50% Threshold | Sensitivity | Specificity |
|---|---|---|
| *H. influenzae* | 100% | 100% |
| *M. catarrhalis* | 89% | 100% |
| *S. pneumoniae* | 100% | 89% |

In conclusion, the following peaks were most important in classification of bacteria that cause AOM: *H. influenzae* about 783 cm$^{-1}$ (Cytosine, uracil ring stretching), *M. catarrhalis* about 1431 cm$^{-1}$ (symmetric CH$_2$ bending and wagging), and *S. pneumoniae* about 840 cm$^{-1}$ (pyranose in peptidoglycan). The positive and negative slope of the 1449 cm$^{-1}$ (CH$_2$/CH$_3$ deformations in lipids/proteins) peak was consistent in classifying each type of bacteria.

To the best knowledge of the inventors, this is the first report of Raman spectra of the three main types of bacteria that cause AOM. It is conclude that Raman microspectroscopy can be used to distinguish the three main otopathogens in vitro that cause AOM. This further motivated the goal of using Raman spectroscopy as a non-invasive clinical tool to identify bacteria involved in AOM.

Detection of Live vs. Dead Bacteria

Figure 11:
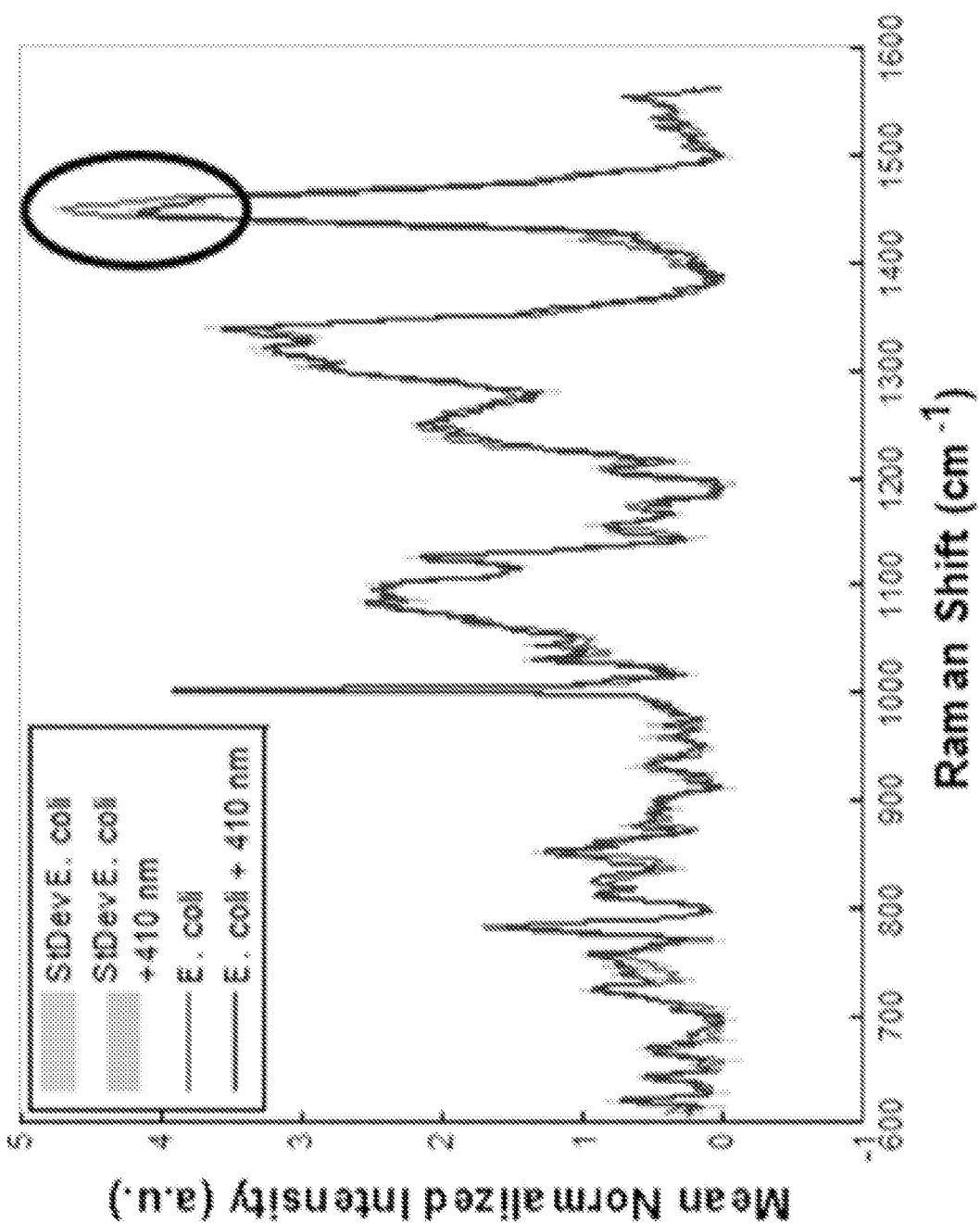
FIG. 11 shows mean±standard deviation Raman spectra of non-light treated *E. coli* and 410 nm-treated *E. coli* grown on MH agar according to one embodiment of the invention.
Figure 12:
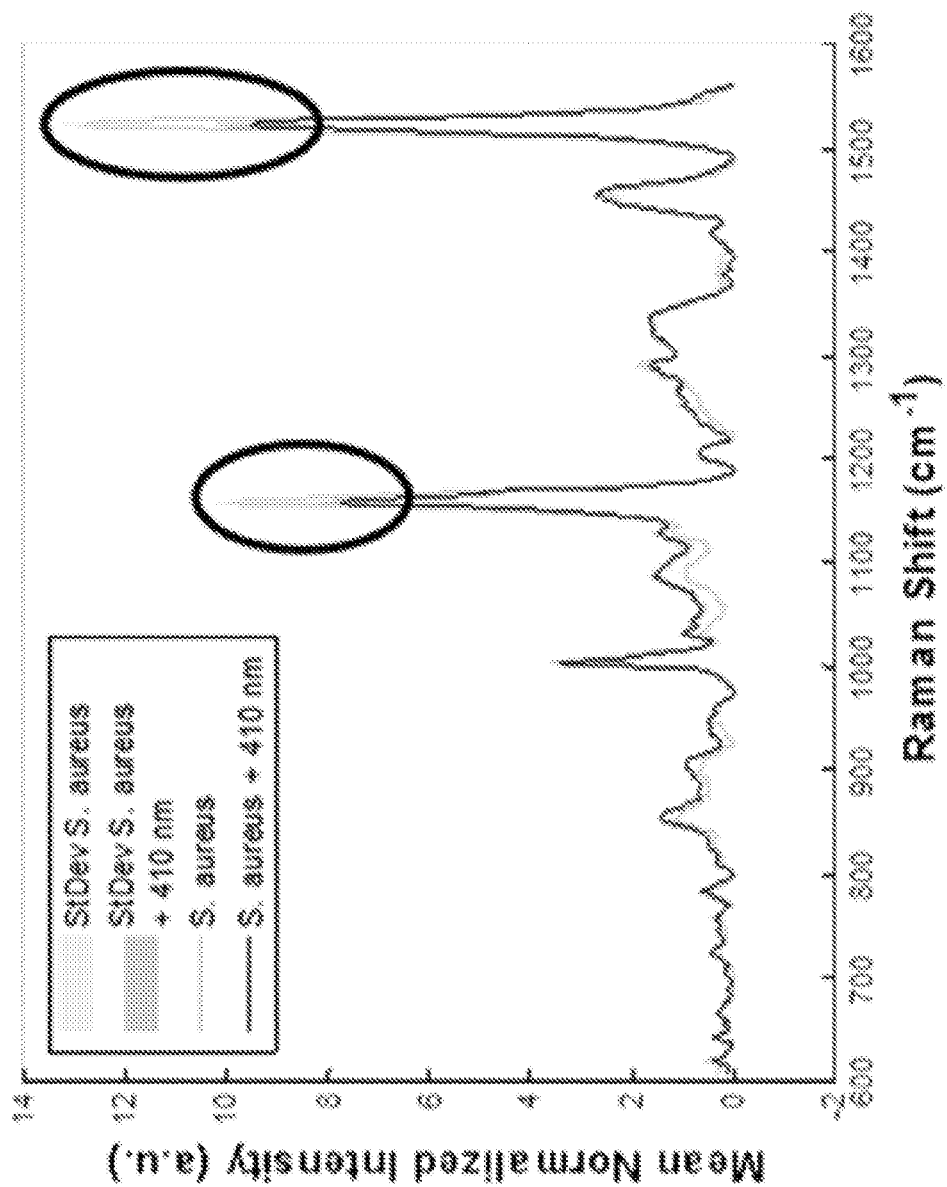
FIG. 12 shows mean±standard deviation Raman spectra of non-light treated *S. aureus* and 410 nm-treated *S. aureus* grown on MH agar according to one embodiment of the invention.

MH agar was used to grow *Escherichia coli* (Gram-negative) and *Staphylococcus aureus* (Gram-positive) in separate petri dishes. A 21 hour incubation period was used for these bacteria. Two plates for each bacteria were prepared, one as a control (no light treatment) and the other plate would be treated with 410 nm irradiation for 15 minutes to kill the bacteria. A 410 nm light with an array of LEDs was placed directly above the agar plate with bacteria after removing the cover plate. Raman micro spectroscopy was performed with a 785 nm excitation source using a 100×/0.85 objective with a 15 second exposure, 20 second photobleach, and 5 accumulations. The power was about 27 mW at the sample with a 1 μm laser spot diameter. Preliminary results from *E. coli* treated with 410 nm show minimal visual changes (FIG. 11). A Raman peak of interest may be about 1450 cm$^{-1}$ which presents a decrease in intensity. *S. aureus* also presented a decrease in intensity of two main carotenoid peaks at 1159 cm$^{-1}$ and 1522 cm$^{-1}$ (FIG. 12).

Identified Problems and Alternate Strategies:

One of the challenges is efficiently killing bacteria for the live vs. dead bacteria model without the need of adding any chemicals that may be Raman active. Light irradiation at 410 nm has been shown to kill methicillin-resistant forms of *S. aureus* bacteria, but may require an added chemical reagent that is photoactive and promotes cell death. Alternative methods include trying UV light that is known to disrupt the cell wall and affect cell metabolism. Multiple irradiation periods is tested to evaluate which is optimal for cell death. A serial dilution is plated to quantify cell death. A more clinically relevant bacteria killing method may be to inoculate a fluid culture of bacteria with an antibiotic known to kill the bacteria and collect Raman spectra of the fluid before and after treatment.

According to the exemplary embodiment, Raman microspectroscopy can be used to discriminate bacteria in vitro and identify reliable biochemical features that play a role in the discrimination of bacteria. In addition, a reproducible live vs. dead bacteria model in vitro is created, which can be used to test if Raman microspectroscopy can distinguish between live vs. dead bacteria, specifically for bacteria that cause AOM. Furthermore, the approach can be used to distinguish bacteria and viability in a mixed bacteria model.

Example 2

Identification of Bacteria in Human Middle Ear Effusion (Mee) Ex Vivo Using Raman Microspectroscopy In the exemplary example, MEE is collected from patients undergoing insertion of a tympanostomy tube, a procedure used to treat recurrent cases of AOM, at Monroe Carell Jr. Children's Hospital at Vanderbilt University. Patient information including age, gender, history of OM, initial diagnosis, duration of infection and treatment is collected upon approval from the Institutional Review Board (IRB) at Vanderbilt University. After collection, MEE samples are prepared to be cultured, Gram-stained, and tested with biochemical assays to determine bacteria involved and their viability. A portion of each original MEE sample is loaded on a Raman substrate to collect Raman spectra using confocal RM.

Since MEE is a multi-component fluid, one embodiment of the invention is to evaluate the major components, which include red blood cells (RBCs), white blood cells (WBCs), and serum to determine their Raman spectral features. A portion of an original MEE sample is prepared and centrifuged to separate the different components and stained to determine cellular morphology. These components are then loaded separately on a Raman substrate to collect Raman spectra using confocal RM. These spectra that pertain to the individual MEE components are then added together and subtracted from Raman spectra of the original MEE sample to determine biochemical features that are attributable to bacteria. These bacterial Raman markers are then correlated with the results from the biochemical assays to identify specific spectral features that are unique to each bacterium and are used to classify bacteria involved in the MEE on a case by case basis. Raman spectra from MEE bacteria colonies are compared to Raman signatures of the characterized bacteria to develop a classification algorithm using a logistic regression model.

It is important to evaluate the feasibility of using Raman spectroscopy for identifying bacteria that cause AOM in human middle ear fluid. Utilizing human middle ear effusion (MEE) from patients undergoing tympanostomy allows one to investigate the complexity of a multi-component fluid from a biochemical perspective. Although these patients may have undergone previous antibiotic treatment, it aids in understanding the major components in a mixed fluid sample and whether there are bacteria still involved in the collected fluid.

Collection of Human Middle Ear Effusion Samples:

The ear canal of the patient undergoing tympanostomy, a procedure performed to treat recurrent cases of AOM, is sterilized to minimize contamination. Effusion is captured using a sterile Juhn Tym-Tap middle ear fluid device (Medtronic Inc., Minneapolis, Minn.) with an aspirator to collect the sample in a tube that is capped after collection. Each tube sample is labeled with a patient identifier that includes the origin of the MEE (left vs. right ear). The tubes is placed in a biohazard bag and transported immediately to the lab for analysis. Information that may be important in evaluating the MEE include age, gender, history of AOM, initial diagnosis, duration of infection, and treatment.

Preparation of Human Middle Ear Effusion Samples:

After MEE is collected from the patient it is analyzed to determine the major components involved. The average volume of MEE that are collected is about 30 μL. This is transferred to a 1 mL centrifuge tube and mixed with 100 μL of deionized water by using a vortex mixer. A small volume is used to culture directly on agar plates. MEE samples are initially cultured on commonly used agar that include trypticase soy agar (TSA) with 5% sheep blood and chocolate agar at 37° C. and 5% $CO_2$. Bacterial growth is compared to growth on MH agar (with XV factors) to ensure at least the three main bacteria that cause AOM is grown at 37° C. and 5% $CO_2$.

Another small volume from the original MEE sample is used for Gram stain analysis that will aid in determining bacteria type. A Gram stain is performed from the original MEE sample and cultured bacteria derived from the MEE sample after a 72 hour incubation. A standard inverted microscope is used to evaluate the Gram stained slides and images is collected using a camera attached to the microscope.

After the 72 hour incubation of MEE samples at 37° C. and 5% CO2, agar plates are visually inspected for growth of any bacteria. A small mass of a bacterial colony that has grown from a particular MEE sample is collected and mixed in MH broth. This liquid culture is then used to re-culture bacteria on a new MH agar (with XV factors) plate at 37° C. and 5% $CO_2$ for 24 hours.

Bacterial colonies from the second agar growth cycle are used to inoculate MH broth. After mixing, 10 μL of the liquid culture is used to determine the biochemical profile of the bacteria using an analytical profile index (API) kit (bioMerieux, Lyon, France). Three biochemical assay kits are utilized to identify the species of the most common pathogens that cause AOM. These include the API NH kit (*H. influenzae* and *M. catarrhalis*), API 20 Strep Kit (*S. pneumoniae*), and API Staph Kit (*S. aureus*).

MEE samples are also be analyzed to quantify the amount of live vs. dead bacteria in each sample. This information is critical since a majority of these patients may have already received some type of antibiotic treatment. Therefore, there may be fragments of dead and live bacteria, which aids in the evaluation while comparing with the collected Raman spectra. A bacterial viability stain and confocal laser scanning microscope (CLSM) is used to differentiate live vs. dead bacteria. Since CLSM does not require for bacteria to be grown on culture, it aids in identifying bacteria that are not culturable. CLSM also provides three-dimensional structure of bacteria communities typical of biofilms.

Raman Microspectroscopy of Human Middle Ear Effusion and Bacterial Colonies:

In one embodiment, a Raman microscope with 785 nm excitation is used for analysis of MEE samples. MEE samples are plated on MH agar (with XV factors) and incubated for 72 hours at 37° C. and 5% $CO_2$. Any bacterial colonies that grow from these plates are re-streaked on MH agar (with XV factors) to minimize contamination during the long incubation periods. After a 24 hour incubation period at 37° C. and 5% $CO_2$, bacterial colonies from these plates are analyzed using the Raman microscope.

Acquisition parameters need to be determined during experimental setup. Multiple Raman spectra from multiple spots and colonies are collected for processing and analysis.

Figure 13:
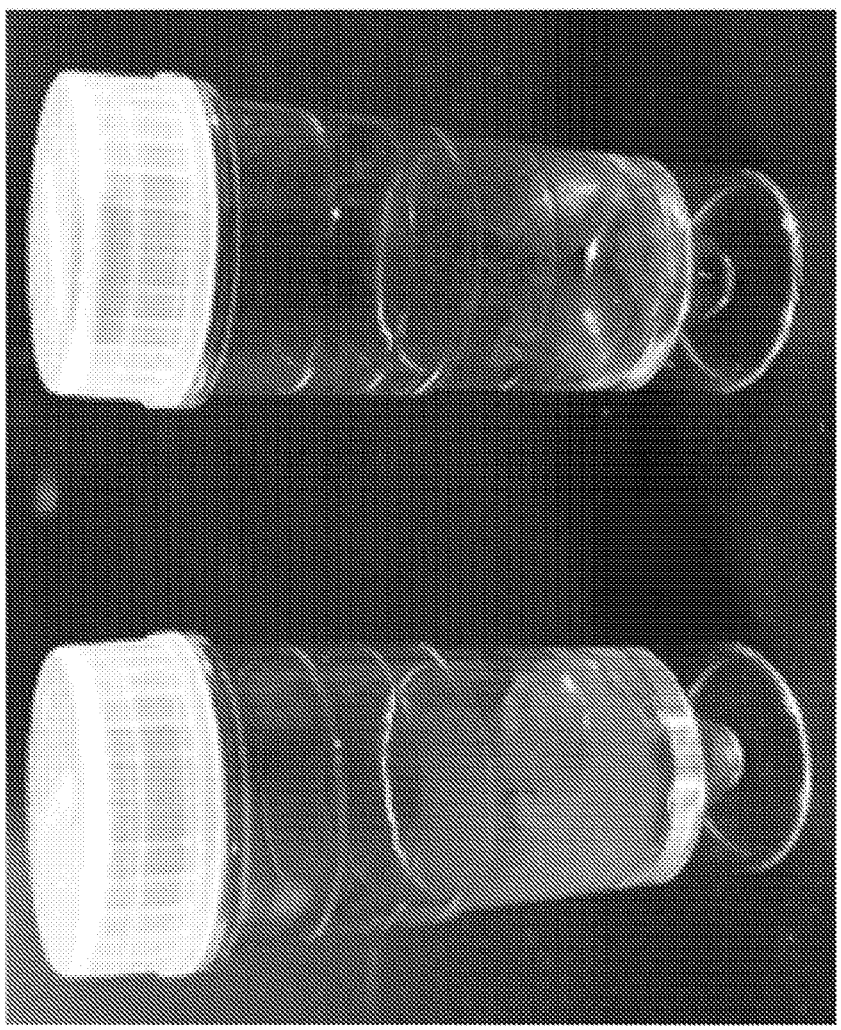
FIG. 13 shows two middle ear effusion samples from human patients.

In addition to evaluating the biochemical features from bacterial colonies of MEE samples, the potential of using Raman microspectroscopy directly on the MEE sample without any further preparation is also investigated. Examples of MEE samples collected from human patients may present with different concentrations of blood and pus (FIG. 13). Collected MEE samples are placed directly on a Raman substrate such as $CaF_2$ or stainless steel and allowed to dry overnight in a sterile environment. After drying, MEE samples on the Raman substrate are characterized using Raman microspectroscopy. Acquisition parameters are determined to avoid saturation, while maximizing SNR. Multiple Raman spectra from multiple spots on the dried MEE sample are collected for processing and analysis.

Sample Size Estimation:

A standard sample size calculation was used to estimate the number of bacteria samples needed for the ex vivo study. The sample size (n) needed was calculated using equation (1). The effect size (0.12 a.u.) and standard deviation ($\sigma_1=0.06$ a.u. and $\sigma_2=0.08$ a.u.) were based on previously collected data for live versus dead bacteria and yielded a sample size of 5.7041. Therefore, estimated 6 samples are needed for each group (AOM and OME). Since the effect size used for this sample size calculation is based on the previously collected data distinguishing live versus dead bacteria in vitro, the number of ear effusion samples needed for the study may be larger than anticipated due to additional complexity in the ear effusion samples.

Data Analysis:

After Raman spectra are collected from MEE samples, a preliminary statistical analysis approach such as a Student's t-test is calculated at each wavenumber and the significance threshold is calculated using a multiple comparison correction to identify Raman peaks that may be important in identifying the presence of bacteria.

Since MEE is comprised of multiple components, which include red blood cells (RBCs), white blood cells (WBCs), and serum, the biochemical features of these components are evaluated individually using Raman microspectroscopy. A components analysis approach is used by adding the Raman spectra of the components and this summed Raman spectrum is then subtracted from the original MEE sample Raman spectrum to determine Raman peaks that are attributable to bacteria. These bacterial markers are then correlated with results from the biochemical assays to determine which features may be linked with each bacteria type. Furthermore, Raman spectra from MEE samples (original MEE and MEE colonies) is compared using a logistic regression model to the Raman signatures collected during characterization of each bacteria type with the goal of classifying each MEE sample.

Figure 14:
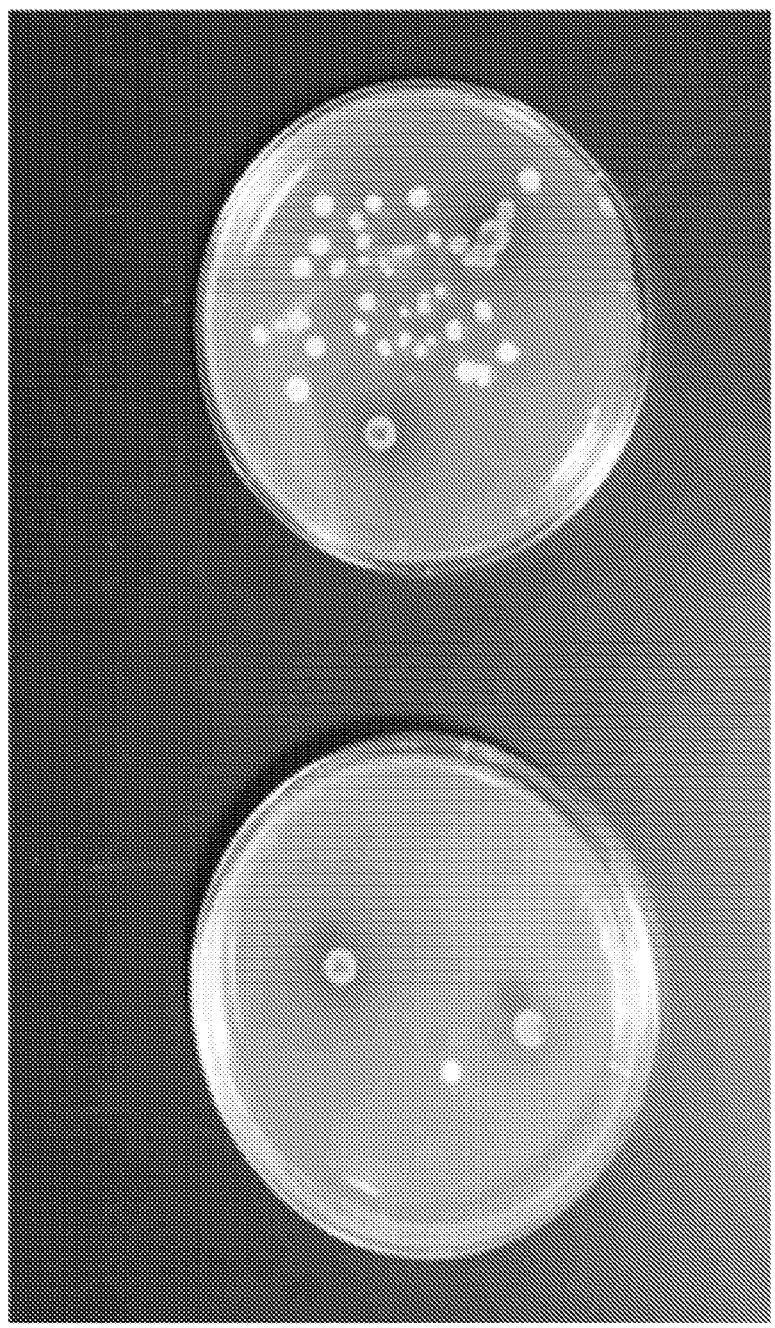
FIG. 14 shows two middle ear effusion samples from human patients cultured on MH agar with XV disks.
Figure 15:
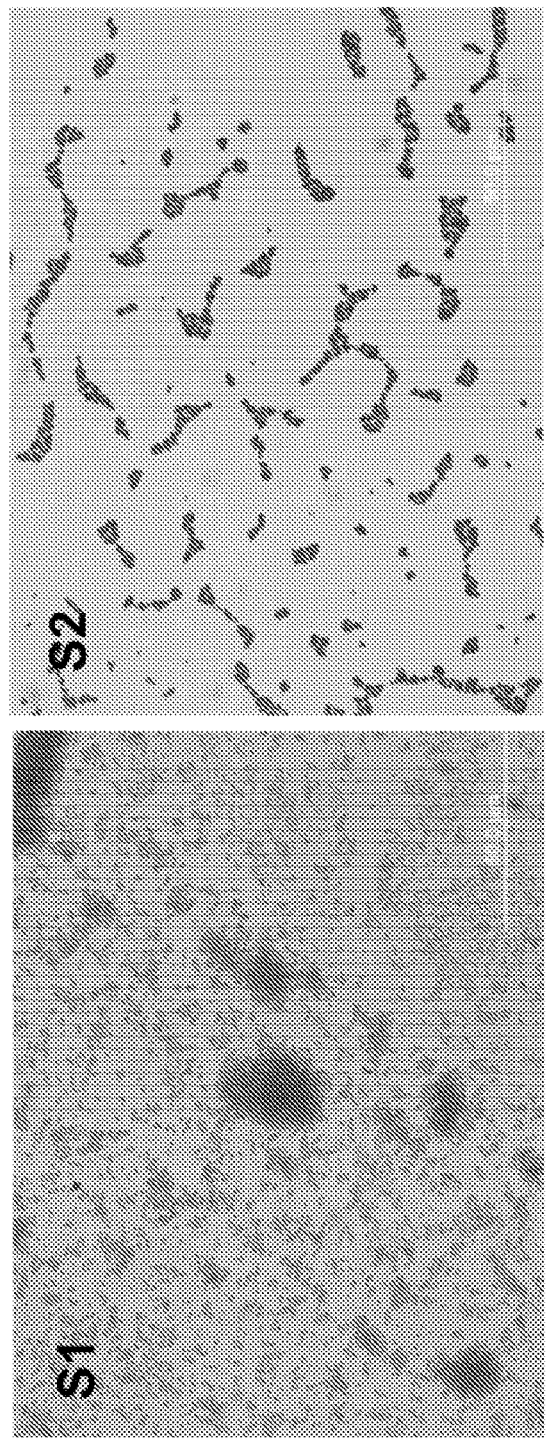
FIG. 15 shows Gram stain from two human middle ear effusion samples according to one embodiment of the invention.

MEE Culture and Gram Stain:

Two de-identified MEE samples were collected and analyzed from separate patients. The protocol for preparation of these samples was previously described. After a 72 hour and additional 24 hour incubation of MEE at 37° C. and 5% $CO_2$ bacterial colonies were analyzed using the same Raman microspectroscopy system that was previously detailed (FIG. 14). After the 24 hour incubation, each MEE sample (S1 and S2) were analyzed using a Gram stain (FIG. 15). From initial inspection, it appeared that the bacteria that grew were not *H. influenzae* since they grew outside of the range of the XV disks. Additionally, bacterial colonies were large and round comparable to *M. catarrhalis*. Furthermore, a hockey puck test, which tests if a colony can be pushed along the surface of the agar, showed the colonies could be easily slid across the MH agar, representative of *M. catarrhalis*. However, the Gram stain analysis presented Gram-negative (FIG. 14: S1) and Gram-positive (FIG. 14: S2). In addition, S2 presented more organized and compact bacteria as can be seen in the Gram stain (FIG. 15).

Figure 16:
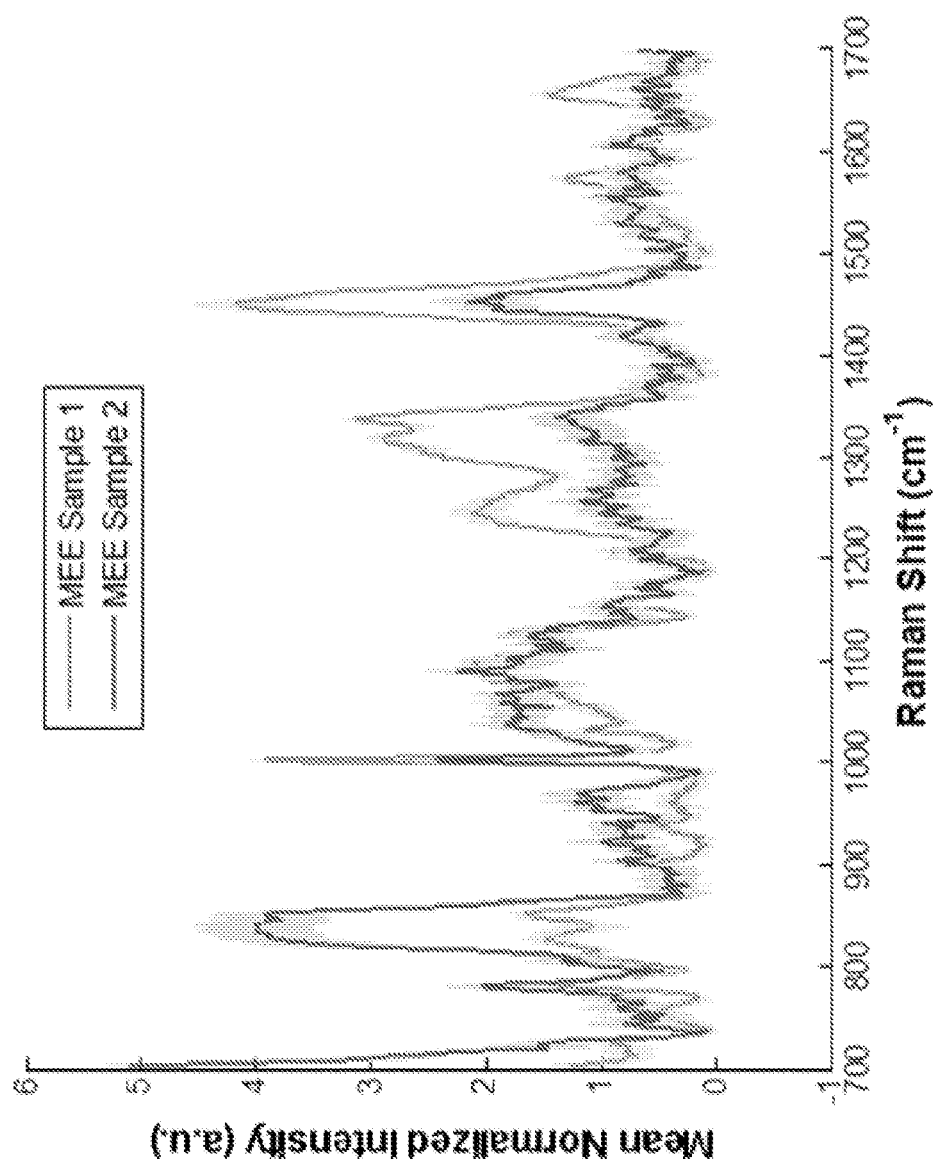
FIG. 16 shows mean±standard deviation Raman spectra of bacterial colonies from MEE samples cultured on MH agar according to one embodiment of the invention.
Figure 17:
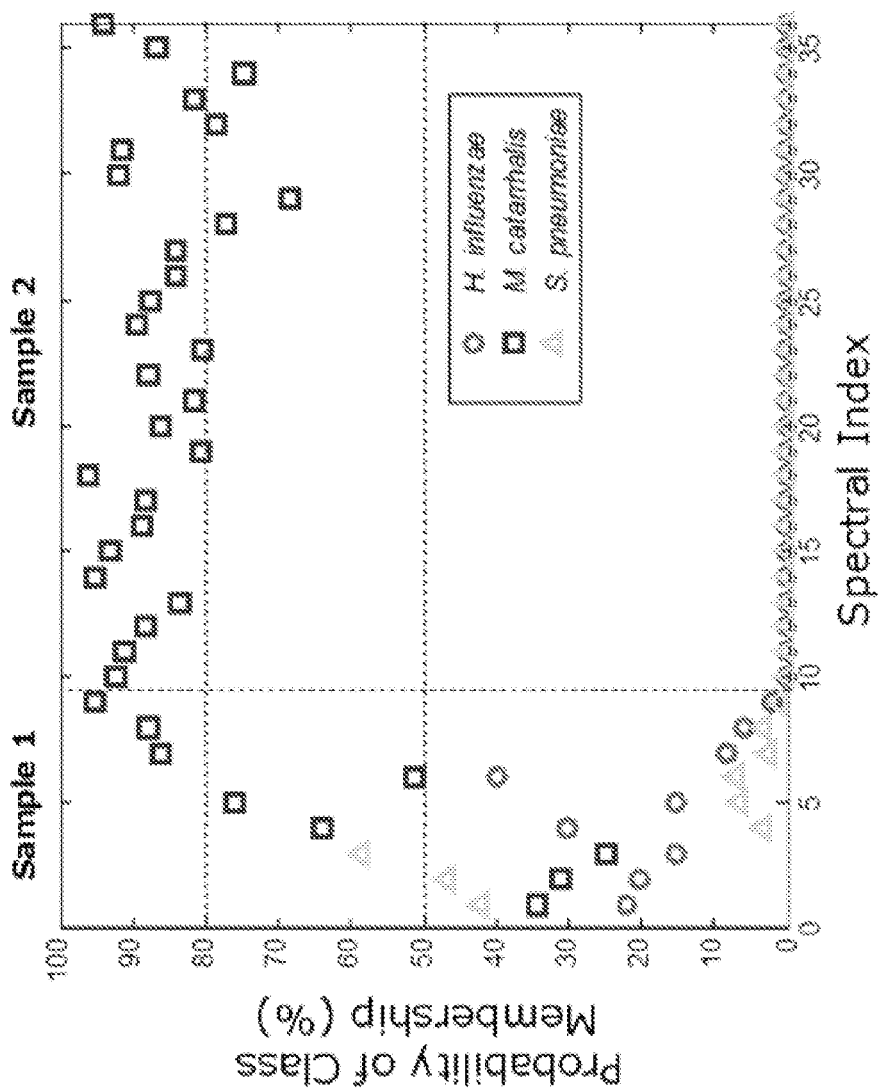
FIG. 17 shows posterior probability for classification of MEE samples to one of the three main bacteria that cause AOM according to one embodiment of the invention.

Raman Microspectroscopy Analysis of MEE Colonies:

Bacterial colonies after the 24 hour incubation period were analyzed using Raman microspectroscopy using a 100×/0.85 NA objective to focus a 1 gm laser spot diameter on a colony. The laser power at the sample was about 24 mW. Acquisition parameters included 1) a 15 second exposure with 3 accumulations and 2) a 30 second photobleach to reduce fluorescence from the colony. A total of 3 acquisitions were collected for each spot with 3 spots collected for each colony. Only one colony was investigated from MEE sample 1 (S1) since there was only one colony. Raman spectra were mean normalized for each MEE sample (FIG. 16). Distinct biochemical features could be seen initially from the Raman spectra of the two MEE samples. Mean normalized Raman spectra from the two MEE samples were analyzed using SMLR to classify which bacteria type it may be based on using the training data set provided by characterization of *H. influenzae*, *M. catarrhalis*, and *S. pneumoniae*. The probability of each MEE sample being one of these bacteria was plotted based on the findings from SMLR (FIG. 17). The probability of each MEE sample being any of these bacteria was evaluated (Table 5). The first two Raman spectra of sample 1 were not classified since their probability of class membership was less than 50%. The sensitivity and specificity were also calculated for the grouped MEE samples (Table 6). These preliminary results shows that, microbial colonies from MEE samples (n=2) can accurately be classified.

TABLE 5

Probability of each MEE sample being one of the three main bacteria that cause AOM from SMLR ($\lambda = 1.0$).

| $\lambda = 1.0$, 50% Threshold | Sample No. 1 | Sample No. 2 |
|---|---|---|
| Probability of *H. influenzae* | 0% | 0% |
| Probability of *M. catarrhalis* | 67% | 100% |
| Probability of *S. pneumoniae* | 11% | 0% |

*Two Raman spectra were not classified since <50% probability of class membership.

TABLE 6

Sensitivity and specificity for both MEE samples.

| $\lambda$ = 1.0, 50% Threshold | Sensitivity | Specificity |
|---|---|---|
| Grouped Samples | 92% | 97% |

Identified Problems and Alternate Strategies:

One of the overarching challenges with analyzing ex vivo samples from patients undergoing tympanostomy is that a majority of this fluid has experienced some type of antibiotic treatment over an extended period of time. Therefore, the original bacteria causing the infection may be killed, mutated to form some antibiotic resistance, or is still alive. This may not be representative of the original infection that presented in the patient. Although this may be a limitation, it does allow one to investigate if Raman spectroscopy is able to detect and identify bacteria in clinical samples that typically have a mixture of varying concentrations of RBCs, WBCs, and serum in addition to bacteria. Furthermore, it allows one to better understand the proportionality of live vs. dead bacteria.

Another challenge with the MEE samples is that they are a multi-component problem. Therefore, it is challenging to attribute bacterial markers in a sample that is mixed with unknown Raman features of the multiple factors. Therefore, a possible solution would be to separate the RBCs and WBCs from the MEE based on a density gradient. With this approach, the major components of a sample could be analyzed using Raman microspectroscopy to identify their biochemical features. Alternatively, Raman spectra from each component of a typical MEE sample could be analyzed and used to identify biochemical features that are unique to bacteria. Varying concentrations of each component could be measured to determine the limit of detection using Raman microspectroscopy.

According to the exemplary embodiment, the main components typically seen in MEE samples are characterized, and these biochemical features are used to build a representative model of MEE spectral features. In addition, this aids in gaining insight into determining biochemical features that are relevant for detecting the presence of bacteria and identifying bacterial type in an ex vivo model. This allows one to create a library of biochemical features that is important for detection of bacteria. In addition, other bacteria types that are less common, but known contributors to AOM, are also investigated. Furthermore, the limit of detection of the system is determined by varying the concentrations of the major components that make up a typical MEE sample.

Example 3

Fiber-Optic Probe-Based Raman Spectroscopy System to Identify Bacteria

In the exemplary embodiment, a custom fiber-optic Raman probe is designed using ray-tracing software to optimize the collection volume of fluid containing bacteria after being scattered through a TM phantom. Multiple TM phantom models are fabricated based on matching optical properties and dimensions to represent the different clinical presentations of each condition: normal, AOM, and OME. The optical properties from standard animal models, for each condition are incorporated into Monte Carlo simulations. Following simulation, a Raman probe is designed, fabricated, and evaluated. After determining the simulated feasibility, the fabricated Raman probe is tested on its ability to emit excitation light at a wavelength of 785 nm through the TM phantom and collect Raman scattered light primarily from a fluid containing known individual and mixed bacteria samples behind the TM phantom. In addition, MEE samples are collected and placed behind the TM phantom and used to collect Raman spectra. Collected MEE samples and Raman spectra are processed and analyzed as described above.

As discussed above, the framework to characterize bacteria that cause AOM in pure bacteria in vitro and detect the presence of and identify bacteria in multi-component clinical MEE samples ex vivo is provided according embodiments of the invention. To test the feasibility of using RS in a clinical setting to non-invasively investigate bacteria in a fluid environment behind a tympanic membrane, it is important to design a representative model of implementing this approach. Embodiments of the invention are to create a relevant TM model to evaluate the light distribution and heating effect from the light source, and design a fiber-optic Raman probe to optimize collection of biochemical information about the state of an infection.

Figure 18:
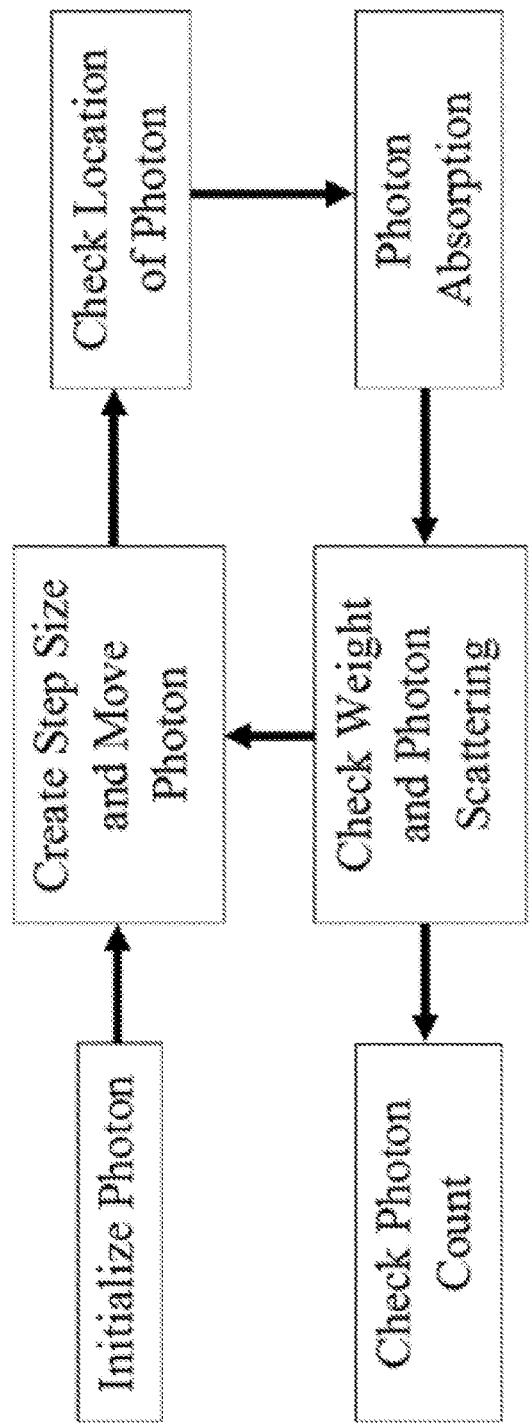
FIG. 18 shows a flowchart of Monte Carlo technique according to one embodiment of the invention.
Figure 19:
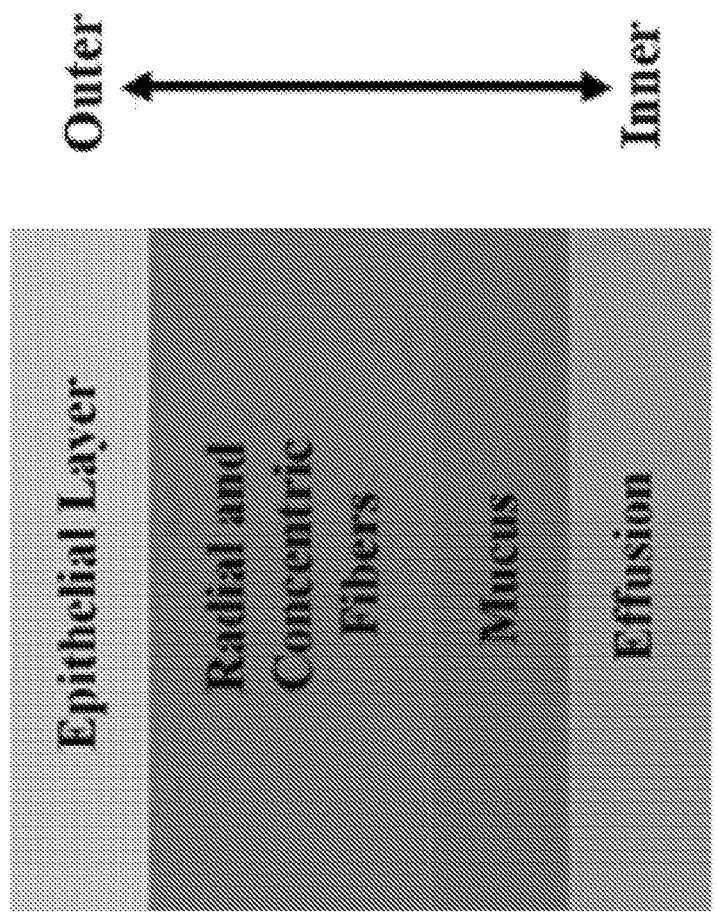
FIG. 19 shows a multilayered model of the tympanic membrane moving from the outermost to the innermost layer according to one embodiment of the invention.

Monte Carlo Modeling and Heat Distribution:

To determine the light distribution and temperature changes in the tympanic membrane (normal and infected) based on the light source design, Monte Carlo modeling and fluence maps are used. Monte Carlo methods simulate photon transport through a bulk or multilayered turbid media. Photon distribution is based on probability distributions when a photon comes into contact with a particle in the media and it is either absorbed or scattered (FIG. 18). In one embodiment, this technique is used for the multilayer model of the tympanic membrane to determine the light distribution (FIG. 19). More specifically, the number of photons that are scattered and reach the effusion layer is evaluated, since this is where the bacteria of interest reside. Since the total thickness of the tympanic membrane changes during an active infection (AOM) mostly due to edema, the thickness in the Monte Carlo model is varied with an inter-layer of intra-cellular water (composed potassium, magnesium, sodium, and chloride ions) to account for this and evaluate the light distribution for multiple thickness levels. To accurately model this one needs to obtain the absorption and scattering coefficients, thickness, and refractive index of each layer, which may be found from previous studies in the literature. Furthermore, fluence profiles are also created using the model to determine energy deposition versus depth of the tympanic membrane and fluid. Another parameter that is critical to this model is the estimate of thermal damage. The Arrhenius thermal damage integral calculation is used to determine thermal damage based on temperature changes versus depth of the model.

Tympanic Membrane Phantom and Bacteria Model:

A tympanic membrane phantom model is made to simulate the human tympanic membrane (TM). The TM is comprised of four layers with a total average thickness of about 70 µm at a normal state. However, during AOM and chronic OM, thickness of the TM can change to an average of about 170 µm or up to about 280 µm (including biofilm formation), respectively. Therefore, it is important to design phantoms with a range of thicknesses to include normal, AOM, OME, and chronic states. An initial design of the optical phantoms will incorporate a recipe for solid epoxy phantoms. One of the advantages of fabricating these types of phantoms is that they do not change over time, are solid, and can be made with any combination of optical properties.

The basic recipe includes 250 mL of resin, 19 drops of a catalyst, $TiO_2$ (scattering agent) suspended in a small amount of ethanol, and an ethanol soluble dye (absorbing agent). After suspending the $TiO_2$ in ethanol and adding the dye, they is mixed thoroughly with resin and catalyst, then cured for about 24 hours at room temperature.

The concentration of the scattering agent, $TiO_2$, which is added in the phantom is calculated by using Mie theory and matched to the scattering coefficient of the multilayered tympanic membrane model. Mie theory can be used to calculate the scattering phase functions and optical properties based on multiple parameters such as the wavelength of the excitation source, index of refraction of the medium, and sphere diameter of the scattering agent. To calculate an estimate of the total reflection and transmission through the sample we plan to implement an adding-doubling calculation, which is based on van de Hulst's adding-doubling technique. The overall thickness and concentration of $TiO_2$ is varied to include relevant models for the control (normal) and AOM mimicking phantoms.

Figure 20:
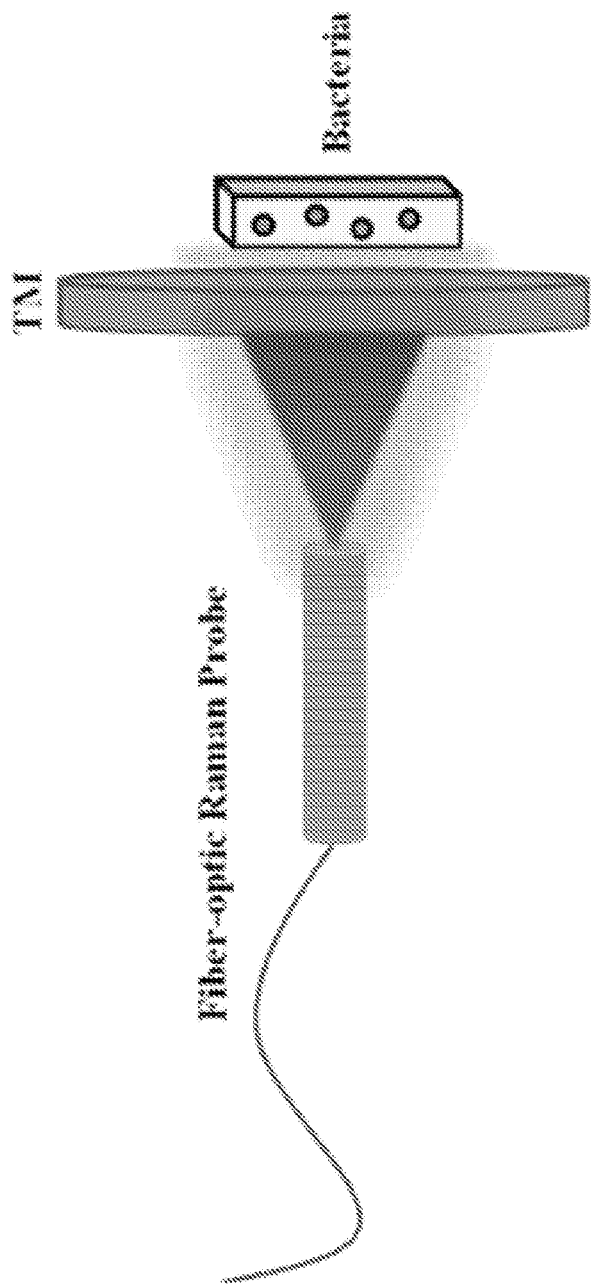
FIG. 20 shows a Tympanic membrane phantom and ear fluid model with a fiber-optic Raman probe according to one embodiment of the invention.

Prior to collecting Raman measurements from the assembled model, Raman spectra are collected from each component to determine the spectral contribution from each in the model. First, a fiber-optic Raman probe is placed perpendicular to the quartz vial filled with MH broth and bacteria, individually and mixed. These samples are spiked with known concentrations of bacteria to determine the limit of detection. Raman data are also collected from the control (quartz vial with MH broth only) and background (empty quartz vial). Next, Raman information is collected from the TM phantoms that model normal and AOM states. Then, the model is assembled by placing TM phantoms vertically in front of a quartz vial filled with bacteria in MH culture broth (FIG. 20). The fiber-optic Raman probe is placed perpendicular to the TM phantom and used to irradiate the phantom and MH broth spiked with known concentrations of individual and mixed bacteria. Control and background measurements are collected of a quartz vial filled with MH broth only and an empty quartz vial, respectively. In one embodiment, the fiber-optic Raman probe is held at a fixed distance from the TM that will replicate in vivo limitations.

Characterization of the Tympanic Membrane Phantom Model.

While light is being scattered and absorbed by the TM mimicking layer, it is important to evaluate how 785 nm excitation light affects the TM model. Heat deposition from radiant energy at a specific fluence rate [$J/cm^2$] is measured using a thermal camera to capture rapid changes over time. Characterization using these parameters is performed for the various settings in the TM phantom model. These measurements is recorded and compared to simulated values from the optical modeling. These findings also drive an iterative process to refine positioning of the Raman probe in front of the TM phantom and acquisition settings.

A Fiber-Optic Raman Probe for Characterizing the TM and Bacteria in Fluid:

Since Raman scattering is a rare phenomenon (1 in $10^6$ photons), it is critical to maximize efficiency of photon (from Raman scattering) collection. In addition, it is important to minimize light from the excitation source, optical components from the probe itself, and specular reflectance.

Figure 21:
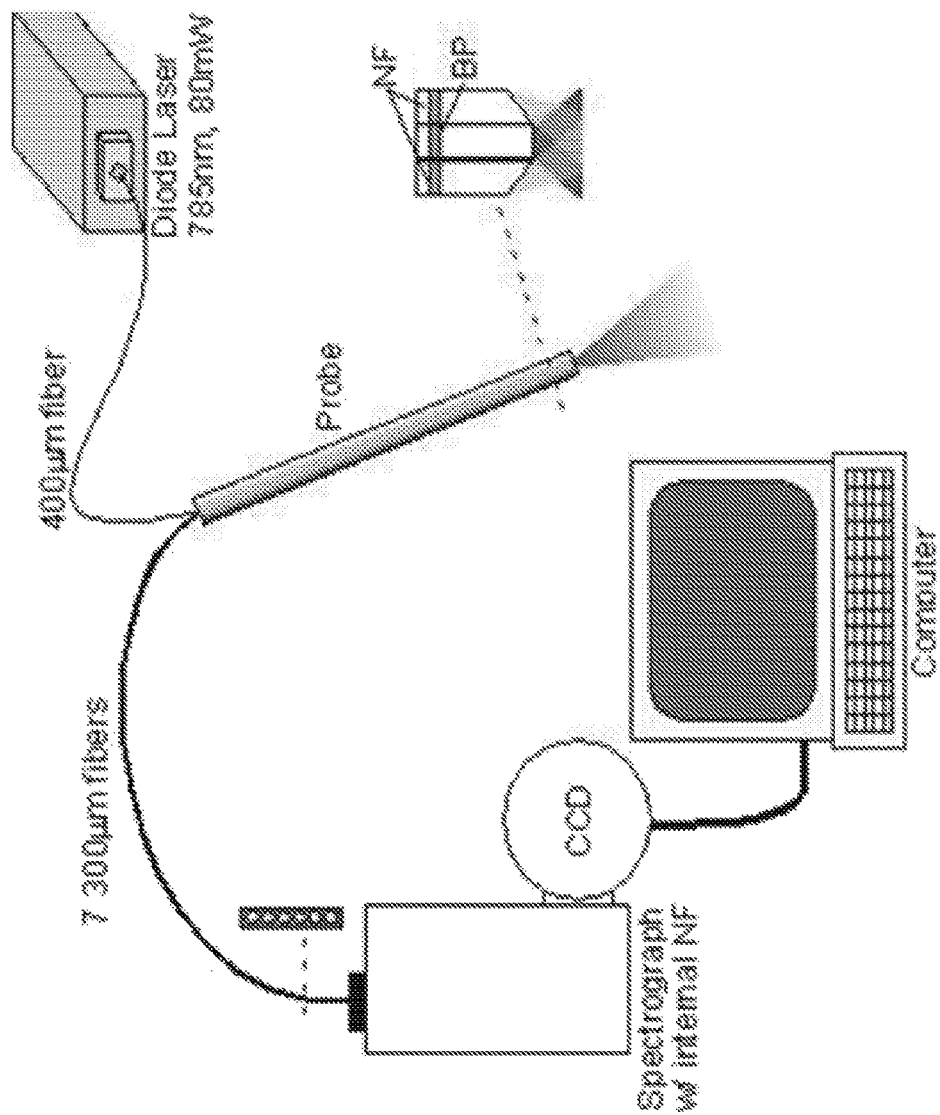
FIG. 21 shows a fiber-optic probe-based Raman spectroscopy system with a 785 nm excitation source according to one embodiment of the invention.

In certain embodiments, the first probe design is to use a volume average approach, which takes an average of the Raman scattered light in the sample over the entire volume interrogated. It includes a fiber-optic Raman probe with a forward-facing excitation source at 785 nm and is used for initial experiments for the tympanic membrane phantom model. One embodiment of the fiber-optic Raman probe system is schematically shown in FIG. 21. In this exemplary embodiment, the system includes one 400 μm excitation fiber with a 785 nm bandpass filter. The fiber-optic probe includes seven 300 μm collection fibers that all include an 800 nm long pass filter and surround the central excitation fiber.

The distal tip of the probe is about 2.1 mm in diameter and both ends of the proximal side of the probe have SMA connectors with vertically stacked collection fibers. The collected light is sent to a detector such as an imaging spectrograph coupled to a thermoelectrically cooled back-illuminated, deep-depleted CCD. The system is controlled with a computer that collects the Raman measurements. Acquisition parameters are determined through testing with the setup to optimize SNR. Spectra are calibrated prior to measurements using protocols implemented in the lab and processed for fluorescence subtraction and noise smoothing. This forward facing probe allows one to collect biochemical information using a volume average of the tympanic membrane and fluid model.

Figure 22:
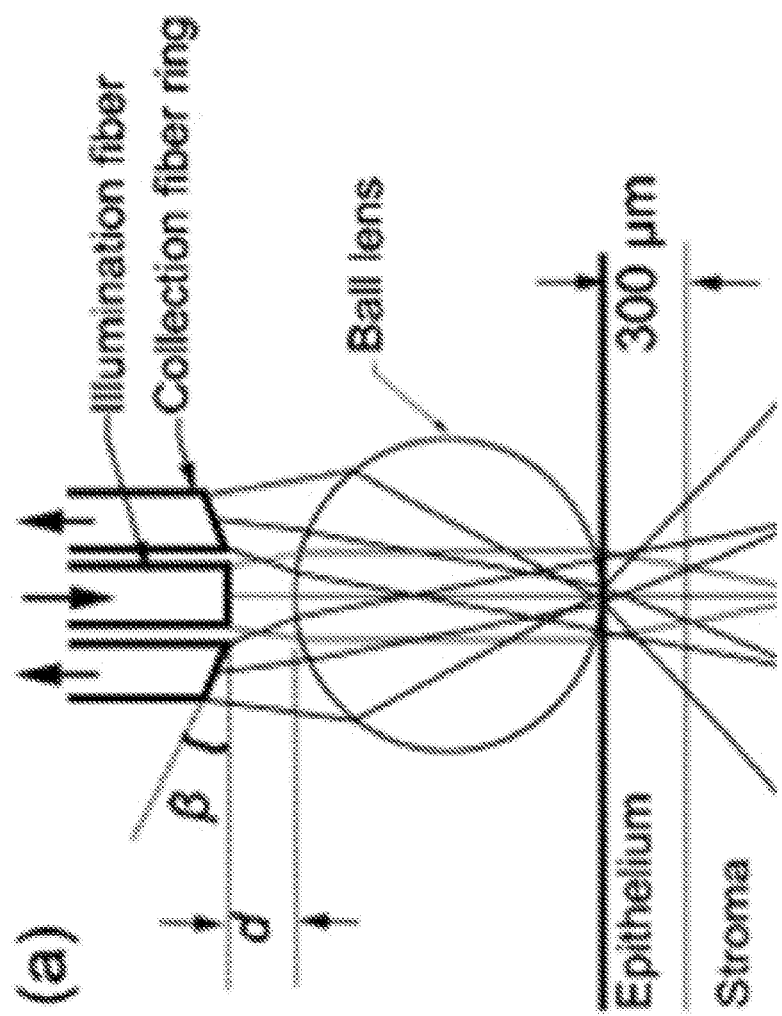
FIG. 22 shows a schematic of a beveled fiber-optic confocal Raman probe according to one embodiment of the invention.
Figure 23:
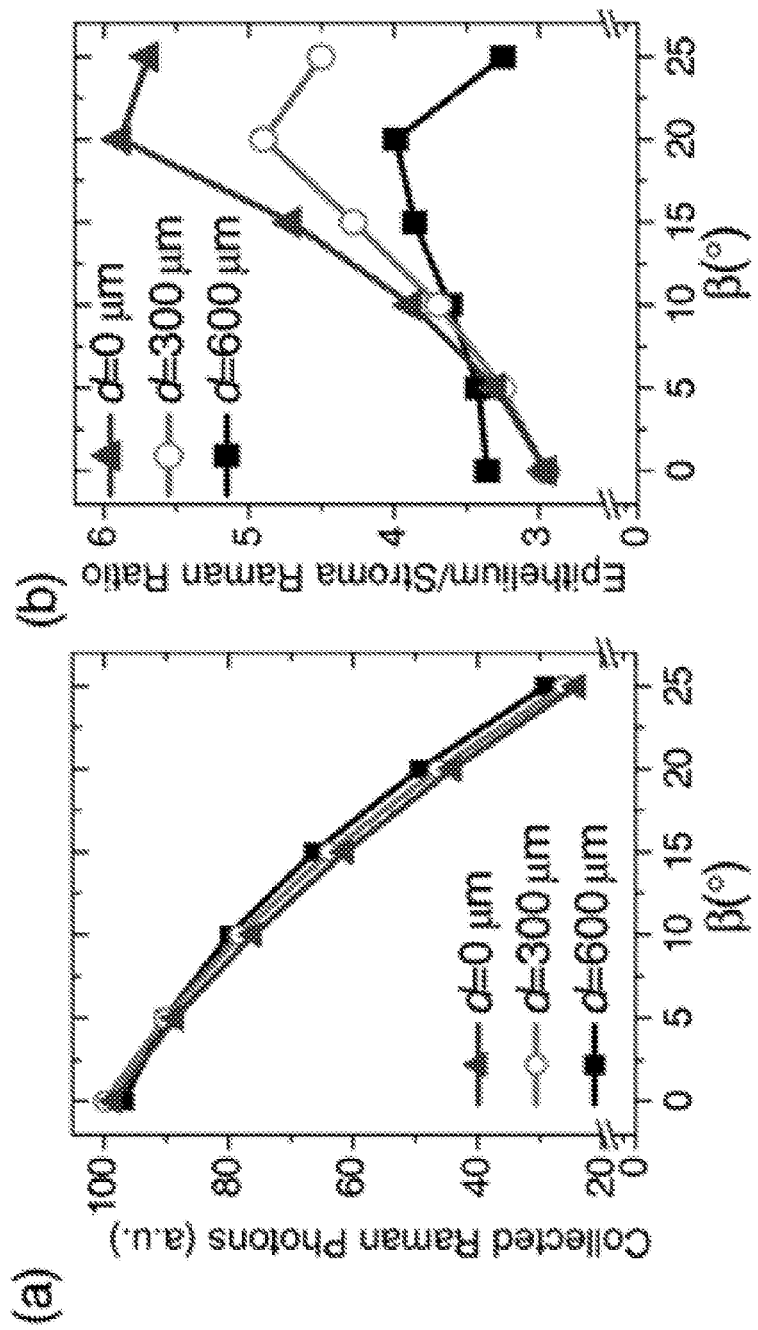
FIG. 23 shows (a) comparison of Raman signal at different distances between the fiber bundle and ball lens and ball lens bevel angle and (b) ratio of superficial layer (epithelium) to stroma layer Raman signal at different depths and balls lens bevel angle, according to one embodiment of the invention.

In certain embodiments, the second probe design is a confocal fiber-optic Raman probe that may be used to investigate specific tissue layers. This setup includes one central excitation fiber surrounded by a ring of beveled collection fibers (FIG. 22). A fiber-ball lens is placed at a specific distance from this fiber setup and acts to focus the excitation light on the sample. By increasing the angle of the bevel it was found that the number of Raman scattered photons decreased dramatically by 80% going from a 0° to a 25° angle (FIG. 23). Furthermore, by increasing the gap between the working end of the probe (fibers) (e.g., 0-600 μm) and the ball lens and increasing the bevel angle, they were able to obtain mostly Raman signal from the superficial layer up until 200 (FIG. 23). Although the main goal of this confocal design was to obtain Raman signal mainly from the most superficial layer, by increasing the gap between the working end of the fibers and the ball lens and altering the collection fibers bevel angle, more Raman signal from the deeper layers may be achieved.

Figure 24:
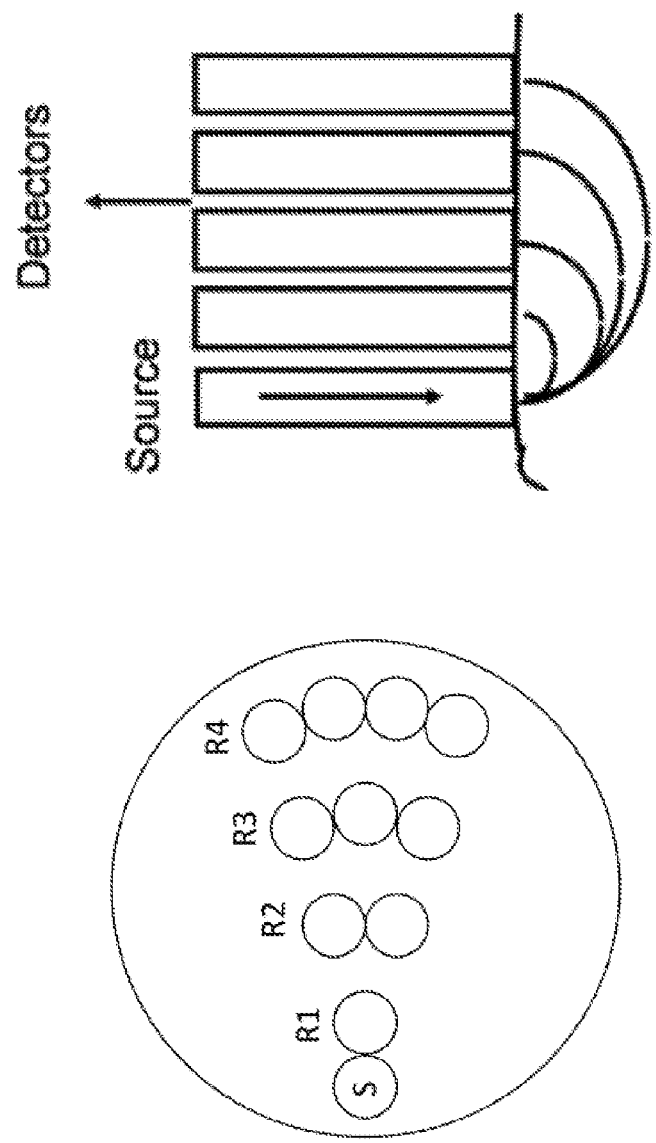
FIG. 24 shows a schematic of spatial offset Raman spectroscopy (SORS) probe where (S) is the source fiber and R1-R4 are collecting fibers according to one embodiment of the invention.

In certain embodiments, the third probe design, spatially offset Raman spectroscopy (SORS), includes a design to probe different depths of a sample. This is important for samples that may either have multiple regions of interest or require greater penetration depth of the excitation source. This setup includes one main excitation fiber, typically placed near the edge of the probe, and multiple collection fibers that are placed in a ring type fashion from one side of the excitation fiber (FIG. 24). The detection fibers that are placed radially farther away from the source fiber are able to collect photons that have travelled deeper due to additional scattering events. This design is able to count the number of photons that were Raman scattered based on the detector fiber offset from the source fiber. Furthermore, it is able to use this SORS probe to evaluate margin status from breast specimens in vitro with a 95% sensitivity and 100% specificity. This design is valuable in obtaining biochemical information from both the inflamed tympanic membrane and bacteria in the MEE, which would be more distal from the probe if performed in vivo. A combined approach may provide more insight into the biochemical changes that occur both for the tympanic membrane swelling and MEE, which may aid in diagnosing AOM and OME more accurately and efficiently. These types of probe designs tend to be larger by a few mm compared to forward facing probes as discussed in the first design option. Although the focus for this aim is to evaluate the TM model, a future application may be to incorporate this design in vivo. Therefore, a more compact version may be needed as the average normal adult ear canal has an average diameter of 7-8 mm.

In certain embodiments, the fourth probe design aims at utilizing the type of Raman probe in an in vivo setting. One major challenge of placing a Raman probe into an ear canal of a patient is knowing the placement of the probe and ensuring it does not make contact with the inflamed TM.

Figure 25:
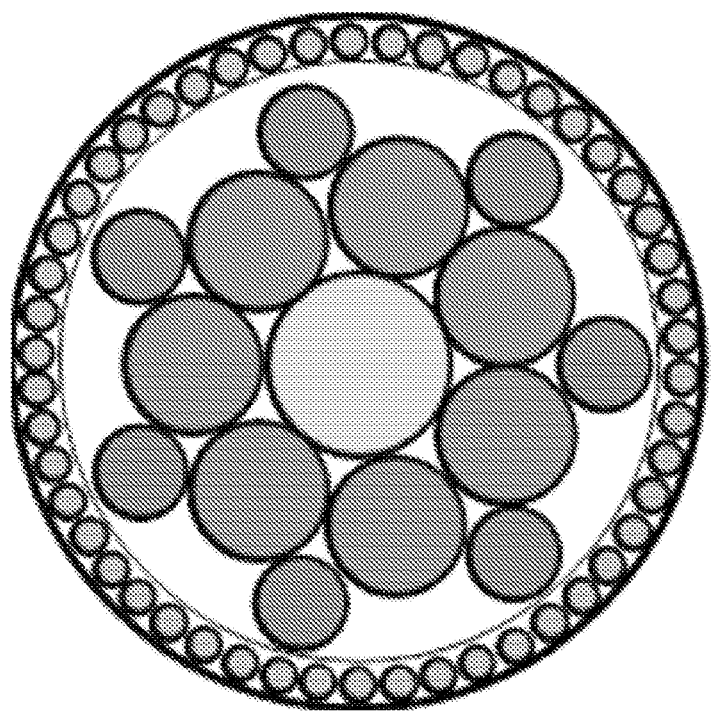
FIG. 25 shows a cross-section schematic of a fiber-optic Raman+ light guidance probe. Yellow=excitation fiber; orange=collection fibers; green=fish-eye lens; blue=LED or other illuminating source, according to one embodiment of the invention.

This probe design incorporates an LED lighting source and detectors into a forward facing layout to allow the user to see where it is being placed (FIG. 25). This Raman probe is able to collect biochemical information over a large volume of the tympanic membrane and MEE. The LED fibers allow illumination as the user places the Raman probe in the patient's ear canal. Once the probe is in the ear canal it relays placement information, similar to how a rearview camera on a vehicle provides guidance for parking, with a fixed distance from the inflamed tympanic membrane. After the probe is set in place, the LEDs are turned off and the user may continue with collecting Raman information by activating the excitation source. Overall, the probe design allows the user to guide placement of the probe to avoid contact with the TM and collect Raman data in vivo.

Sample Size Estimation:

A standard sample size calculation in accordance with equation (1) was used to estimate the number of bacteria samples needed for the in vitro study The sample size (n) needed was calculated using equation (1). The effect size (0.12 a.u.) and standard deviation ($\sigma_1$=0.06 a.u. and $\sigma_2$=0.08 a.u.) were based on previously collected data for live versus dead bacteria and yielded a sample size of 5.7041. Therefore, an estimated 6 samples is needed for each type of bacteria. This sample estimate is for one type of phantom and individual bacteria. for mixed bacteria fluid samples, the number of samples may increase. In addition, the number of samples calculated may increase since a phantom tympanic membrane is placed in front of the bacteria fluid sample.

Monte Carlo Modeling:

Data from Monte Carlo simulations is used to guide the placement of the fiber-optic Raman probe we are planning to initially test. A comparison is made between the different thicknesses of normal and infected (AOM) states and its effect on the number of Raman scattered photons and heating distribution. A simple student's t-test can be used to compare these effects.

Tympanic Membrane Phantom Testing:

Raman spectra collected from the phantom tympanic membrane will first be analyzed to determine biochemical features (Raman peaks) that are representative of the phantom modeling different inflammation states. Raman data is collected for both phantom models, normal and inflamed, and analyzed to determine if there are any significant spectral differences between each model. A ratio or area under the curve of multiple peaks may be used to compare Raman spectra from these phantoms.

Second, Raman spectra from bacteria in individual fluid samples are collected and analyzed using multivariate statistics to classify each bacteria type. For mixed bacteria fluid samples, a multi-class linear discriminant analysis may be used to identify the specific bacteria involved. Raman spectra for the control (MH broth in a quart vial) and background (quartz vial only) are also evaluated to determine if it should be subtracted from the Raman spectra of bacteria in fluid or adjusted using another method. For the combined tympanic membrane and bacteria fluid model, a potential analysis approach combines the use of a multiclass support vector machine (SVM) algorithm and linear discriminant analysis.

A SVM regression analysis will first be used to categorize spectral data of the tympanic membrane from spectral data of mixed bacteria in the fluid. Then, a linear discriminant analysis may be performed only on the spectral information of the mixed bacteria fluid to distinguish the specific bacteria involved.

Characterization of Tympanic Membrane Phantom Model and Raman Measurements:

Heat distribution in the normal and AOM states of the TM phantom as seen with a thermal camera is compared to the MC models.

Design of a Fiber-Optic Raman Probe for Characterizing the TM and Bacteria in Fluid: The Raman probe designs mentioned is design in a ray-tracing software platform to optimize collection from Raman scattered light. Monte Carlo modeling is also utilized to incorporate probe design parameters and measure photon distribution in the model. Heat distribution is also measured using the simulation for each probe design. Results from this testing will help guide the design for assembling an optimal fiber-optic Raman probe for characterization of AOM.

In certain embodiments, the optical properties of the tympanic membrane are collected, which is important for simulation with the Monte Carlo modeling. During this time, preliminary fluid measurements are conducted using the forward facing fiber-optic Raman probe of known bacteria concentrations in the quartz vial. These steps provide guidance for accurately creating the phantom TM model and characterizing the heat distribution when irradiated.

Identified Problems and Alternate Strategies:

One of the major challenges is collecting enough Raman scattered photons from the fluid behind the tympanic membrane phantom, especially with a non-contact probe design. Although the TM phantom is highly scattering, detection of enough photons from beyond 200 µm (to reach the fluid) may be more difficult. In some embodiments, the Monte Carlo modeling with different probe designs is used to estimate as best as possible which fiber-optic probe design is most efficient. If absorption and scattering coefficients of the different tympanic membrane layers cannot be found in the literature, we plan to excise a tympanic membrane from a rat or mouse and determine these values using a spectrophotometer or double integrating sphere setup.

If the TM phantom and bacteria model is not reliable, we plan to use an established AOM chinchilla model to carry out the probe based experiments. Bacteria causing AOM is injected into the chinchilla and then prepared for the fiber-optic Raman probe to be inserted into the ear canal to collect Raman spectra. Anatomy of the chinchilla is studied to prepare for probe placement and avoid contact with the tympanic membrane. Based on the preliminary findings of distinguishing bacteria in vitro we calculate the number of chinchillas needs to have at least an 80% power analysis. However, the number of chinchillas needed for the power analysis will likely be higher as it is a more complex system. Therefore, after collecting data from the estimated number of chinchillas we reevaluate the number needed based on the preliminary analysis.

According to embodiments of the invention, the probe system is able to evaluate the number of Raman scattered photons that are able to be collected from spiked bacteria in fluid in the TM phantom and bacteria model. In addition, the probe system is able to identify probe design parameters that are important in maximizing photon collection efficiency, while avoiding thermal damage to the TM. This information drives optimization of the fiber-optic Raman probe design and implementation for the model to collect Raman spectral information about the bacteria behind the TM. Ultimately, this takes the goal one step closer to being implemented in patients to aid in differentiating AOM from OME and determining the bacteria involved.

Example 4

Characterization of Bacteria Causing AOM Using Raman Microspectroscopy

Selection of agar growth media: Two of the most common agar types for bacterial culture were tested to determine their ability to grow all three bacteria while having the least spectral interference. Chocolate agar medium (Thermo Fisher Scientific, Waltham, Mass.), which is derived from lysed red blood cells and mainly used for fastidious organisms, was purchased in prepared 85 mm monoplates to culture bacteria. Chocolate agar was compared with Mueller-Hinton (MH) agar, which is a non-selective, non-differential microbiological growth medium that contains basic nutrients and no additives, was prepared by suspending 11 g of MH (BD, Franklin Lakes, N.J.) powder and 7.5 g (15% agar/L) of agar (Thermo Fisher Scientific, Waltham, Mass.) in 500 mL of distilled water while heating (180° F.) and stirring. The mixture was then autoclaved at 121° C. for 10 minutes. Bacteria were streaked separately on both MH agar and chocolate agar plates for comparison of agar and subsequent spectroscopic analysis of the bacterial strains.

Bacterial Species:

The three main bacteria that cause acute otitis media (AOM) were purchased from American Type Culture Collection (ATCC): nontypeable *Haemophilus influenzae* (ATCC No. 49766), *Moraxella catarrhalis* (ATCC No. 49143), and *Streptococcus pneumoniae* (ATCC No. 6301). Propagation methods as recommended by ATCC were used for each strain in preparation for bacteria cultures. Each bacterial species was streaked separately onto the MH agar and chocolate agar plates. *H. influenzae* is a fastidious organism that requires lysed red blood cells not found in the MH agar. Therefore, it is commonly grown on the chocolate agar. To be effectively grown on the MH agar, hemin and nicotinamide adenine dinucleotide (NAD)-rich disks (Hardy Diagnostics, Santa Maria, Calif.) were added to the MH agar plates using steel tweezers that were disinfected between the additions of disks. The chocolate and MH agar plates were cultured for 24 hours at 37° C. with 5% $CO_2$.

Human Middle Ear Effusion Samples:

De-identified clinical middle ear effusion (MEE) samples were collected from patients scheduled for myringotomy with tympanostomy tube insertion at Monroe Carell Jr. Children's Hospital at Vanderbilt. A protocol for collection of MEE from patients was used for consent and approved by the Vanderbilt University Institutional Review Board. MEE samples (n=3) were captured using a sterile JuhnTym-Tap middle ear fluid device (Medtronic Inc., Minneapolis, Minn.) with an aspirator. A swab was used to spread MEE on the MH agar plates with added hemin and NAD-rich disks and allowed to incubate for 72 hours at 37° C. with 5% $CO_2$. Viable colonies were then collected using sterile loop and streaked on a new MH agar plate with hemin and NAD-rich disks for a subsequent 24 hour culture at 37° C. with 5% $CO_2$. Evaluation of colony morphology was used as the standard for bacterial identification from MEE samples.

Raman Microspectroscopy:

Raman spectra were acquired using a confocal Raman microscope (inVia Raman Microscope, Renishaw plc, Gloucestershire, UK) with a 785 nm laser diode (Renishaw plc, Gloucestershire, UK). A 100× (N PLAN EPI, NA=0.85, Leica, Weltzlar, Germany) objective was used to focus an about 1 µm laser spot onto the bacterial colony surface at 27 mW. Raman scattered light was epi-detected through the same objective, then passed through a 35 µm slit and dispersed by a holographic grating (1200 lines/mm) onto a thermoelectrically cooled (−70° C.) deep-depleted, CCD that provided a 1 $cm^{-1}$ spectral resolution. The theoretical spatial resolution of the confocal Raman microscope system is about 0.6 µm. System alignment and light throughput to the sample was confirmed before and after experimental measurements with an internal silicon standard intensity at 520 $cm^{-1}$ and laser power at the sample.

Spectral measurements included three acquisitions per spot, three spots per colony, and three colonies per bacteria. Spectral acquisition parameters included a 30-second photobleach followed by a 15-second exposure with 7 accumulations from 700-1800 $cm^{-1}$. Cosmic ray removal from collected Raman spectra was performed using a custom MATLAB script (Mathworks, Natick, Mass.). Raman spectra were then processed to remove background fluorescence using a least squares modified polynomial fitting algorithm [23] and smoothed for noise with a second-order Savitzky-Golay filter [24]. Post-processed spectra were mean normalized to each individual Raman spectrum for comparative analysis.

Data Analysis:

To quantify the spectral analysis, a Bayesian machine learning algorithm, sparse multinomial logistic regression (SMLR), was implemented to determine the potential of classifying collected Raman spectra as *H. influenzae*, *M. catarrhalis*, or *S. pneumoniae*. The SMLR is a supervised learning algorithm that reduces high dimensional multiclass data into features needed for distinguishing between classes [25]. The SMLR calculates a weight value for each spectral feature in a given spectral range based on its ability to separate classes within a given training data set. The statistical model also outputs how often (frequency) spectral features are utilized from the training data to determine classification across all cross-validations.

Figure 27:
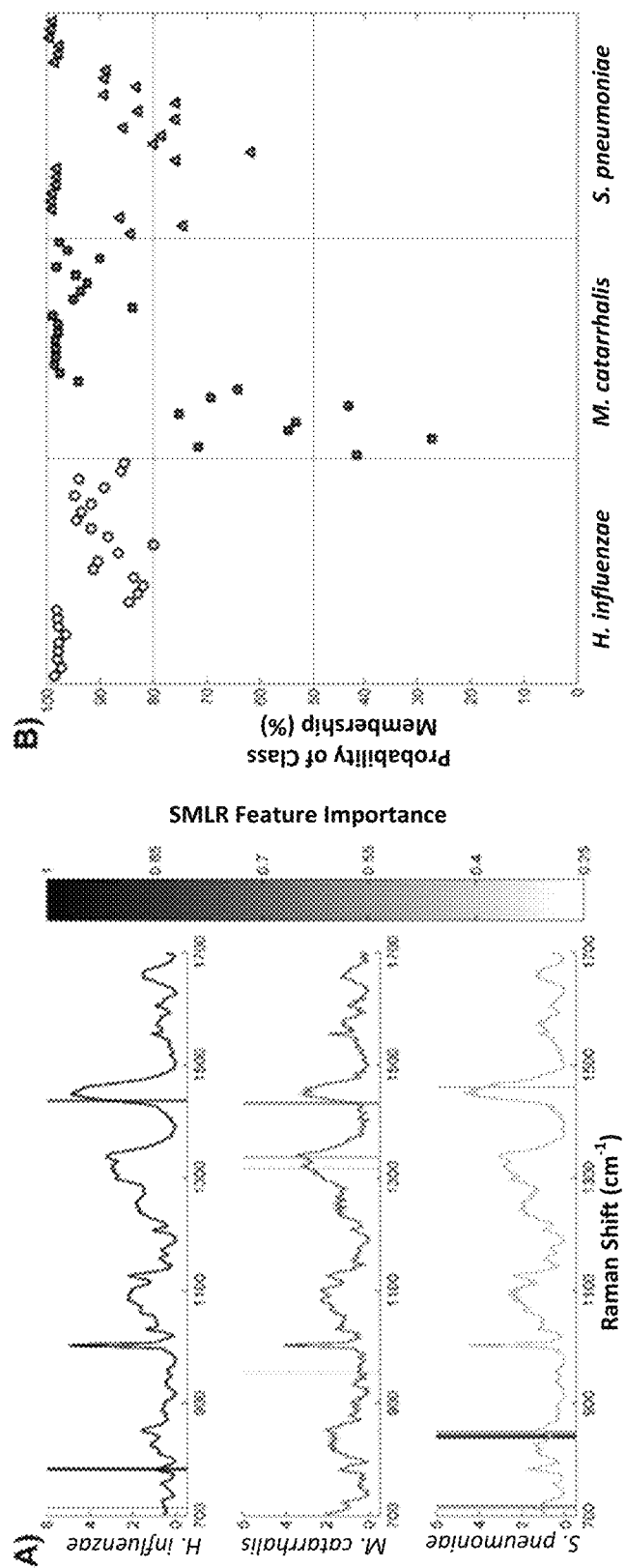
FIG. 27 shows (A) mean±standard deviation Raman spectra of *H. influenzae, M. catarrhalis*, and *S. pneumoniae* grown on MH agar according to one embodiment of the invention. Gray bands represent spectral features used for SMLR classification of each bacteria type by using a sparsity value of A=1.0 for the SMLR input. The band gradient was based on SMLR feature importance. (B) Posterior probability of class membership from SMLR classification for each bacteria based on leave-one-colony-out cross-validation.

To evaluate the importance of spectral features used for classification, a scaled version (from 0 to 1) of both the weight and how often spectral features were found from the SMLR was utilized. The product of these values is used to calculate the SMLR feature importance, which is a quantitative metric that considers both the biochemical differences across the three bacteria characterized in this study and spectral heterogeneity among the same bacteria [26]. The sparsity (Λ) for the SMLR, which controls the capacity for the number of spectral features used for classification, was adjusted to minimize data overfitting. The SMLR feature importance was calculated for *H. influenzae*, *M. catarrhalis*, and *S. pneumoniae* using 77 features (Δ=1.0) (FIG. 27). From the total spectral features available to use, about 8% were used for classification. A total of 917 spectral features from each Raman measurement were available for evaluation. Classification was based on implementing a leave-one-colony-out cross-validation approach. To accomplish this, a k-fold cross-validation was implemented, which separates the original data into k equally sized partitions called subsamples. This cross-validation technique retains one of the k subsamples and uses it to test the model while the remaining k−1 subsamples are utilized as the training data set. A 9-fold cross-validation was used for Raman spectral data analysis. This approach translates to classifying a bacterial colony belonging to specific bacteria and would more accurately evaluate a predictive model.

Figure 26:
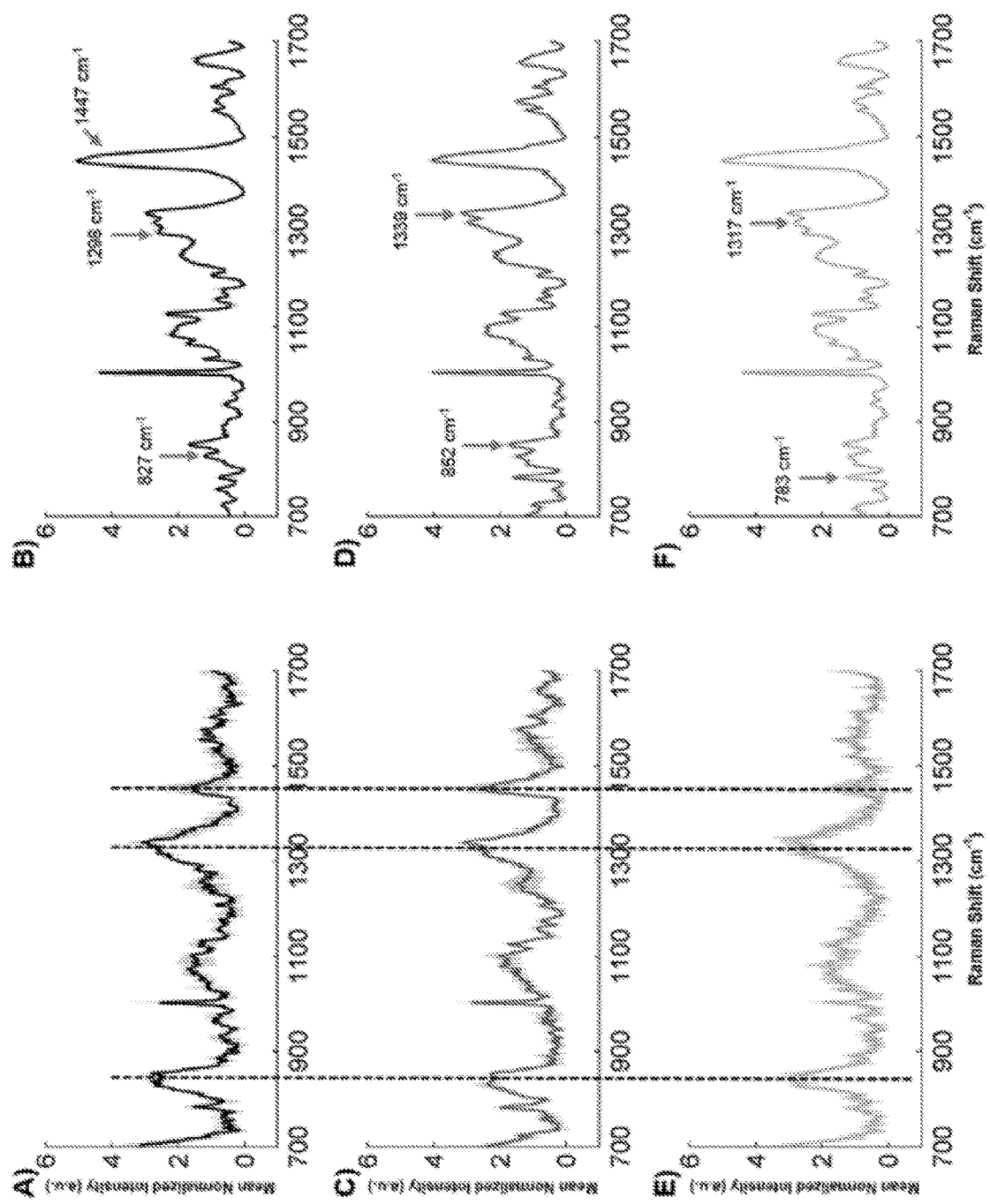
FIG. 26 shows mean±standard deviation Raman spectra of bacteria that cause AOM grown on chocolate agar (left column) and MH agar (right column) according to one embodiment of the invention. (A-B) *Haemophilus* influenza cultured on chocolate agar (A) and MH agar (B); (C-D) *Moraxella catarrhalis* cultured on chocolate agar (C) and MH agar (D); (E-F) *Streptococcus pneumoniae* cultured on chocolate agar (E) and MH agar (F). Vertical dashed lines on the left column represent spectral features from bacteria cultured on chocolate agar that are not discernable, while the arrows in the right column identify these features from the same bacteria cultured on MH agar. A 10× reduction in noise in MH agar compared to chocolate agar was calculated by using the standard deviation of the mean normalized intensity between 1500 $cm^{-1}$ and 1504 $cm^{-1}$.

Results:

FIG. 26 shows the average Raman spectra collected from the three main bacteria that cause AOM, *H. influenzae, M. catarrhalis*, and *S. pneumoniae*, after being cultured on the chocolate agar and the MH agar. A qualitative analysis of bacteria cultured in chocolate agar shows many broad spectral regions with higher standard deviations compared to bacteria cultured on MH agar. Spectral regions that were challenging to discern in chocolate agar are indicated in FIGS. 26A, 26C, and 26E with a dashed vertical line. Raman peaks in this same spectral region for bacteria cultured on MH agar were identified as indicated. A 10-fold reduction in noise was calculated for Raman spectra of bacteria grown in MH agar compared to chocolate agar by using the standard deviation of the mean normalized intensity between 1500 cm$^{-1}$ and 1504 cm$^{-1}$ Spectral analysis of bacteria grown in MH agar resulted in identifiable, reproducible peaks for the three bacteria under investigation that were originally not possible in chocolate agar as shown with arrows in FIGS. 26B, 26D, and 26F Raman features included 827 cm$^{-1}$ (Tyrosine), 1298 cm$^{-1}$ (lipid), and 1447 cm$^{-1}$ (CH2 and CH3 deformations in proteins) for *H. influenzae*, 852 cm$^{-1}$ (CCH aromatic) and 1339 cm$^{-1}$ (CH2 and CH3 fatty acids and proteins) for *M. catarrhalis*, and 783 cm$^{-1}$ (Cytosine, uracil) and 1317 cm$^{-1}$ (Guanine) for *S. pneumoniae*. The signal base line of Raman spectra and spectral peaks highlighted above from MH agar cultures were not affected by the addition of hemin and NAD disks, which were required for growth of *H. influenzae*. From these findings, MH agar was selected as the agar of choice for growing bacteria that cause AOM based on its minimal spectral interference and reduction in noise compared to chocolate agar.

Raman spectra from the three main pathogens that cause AOM were characterized to identify possible biochemical features that may be important in classifying these bacteria. Features of interest based on different peak intensities from mean normalized spectra included cytosine and uracil (ring stretching) at 783 cm$^{-1}$, tyrosine at 828 cm$^{-1}$, tryptophan and exopolysaccharide at 1555 cm$^{-1}$, and adenine, guanine (ring stretching), and C—O vibration modes of peptidoglycan at 1574 cm$^{-1}$ (FIG. 26). These spectral features presented visual differences and were representative of biochemical components of bacteria. Since traditional differences in peak intensities may not capture all of the information found in spectra and informative spectral changes between bacteria types, multivariate statistical analysis was utilized for feature selection and bacterial classification.

FIG. 27 highlights wavenumbers or spectral features that were most important in classification of each bacteria denoted with gray vertical bands on the Raman spectra. The gradient of the vertical gray band in FIG. 27A represents the SMLR feature importance, where darker bands indicate spectral features that were both strongly weighted from their regression coefficients and identified frequently for successful classification. The following peaks were most important in classification of bacteria that cause AOM as determined by SMLR: *H. influenza* at 783 cm$^{-1}$ (Cytosine, uracil ring stretching), *M. catarrhalis* at 1431 cm$^{-1}$ (symmetric CH$_2$ bending and wagging), and *S. pneumoniae* at 840 cm$^{-1}$ (pyranose in peptidoglycan). Furthermore, the positive and negative slope of the 1449 cm$^{-1}$ (CH$_2$/CH$_3$ deformations in lipids/proteins) peak was consistent in classifying each of the three main bacteria that causes AOM. The predicted probability of class membership for each bacteria type is shown in FIG. 27B.

This SMLR classification was based on 77 spectral features (λ, sparsity=1.0) after implementing SMLR analysis on a total of 81 spectra collected from the three main otopathogens that cause AOM (27 spectra from each bacteria type) shown in FIG. 27B. Table 3 presents the classification results as a confusion matrix, which describes the performance of a classification model based on the actual and predicted values. Sensitivity and specificity were also calculated based on the classification using a 50% threshold probability for class membership (Table 4). From the 81 total spectral measurements across all bacteria, less than 5% were misclassified as seen in *M. catarrhalis*. To the best knowledge of the inventors, this is the first report that characterizes the three main bacteria that cause AOM using Raman spectroscopy.

Figure 28:
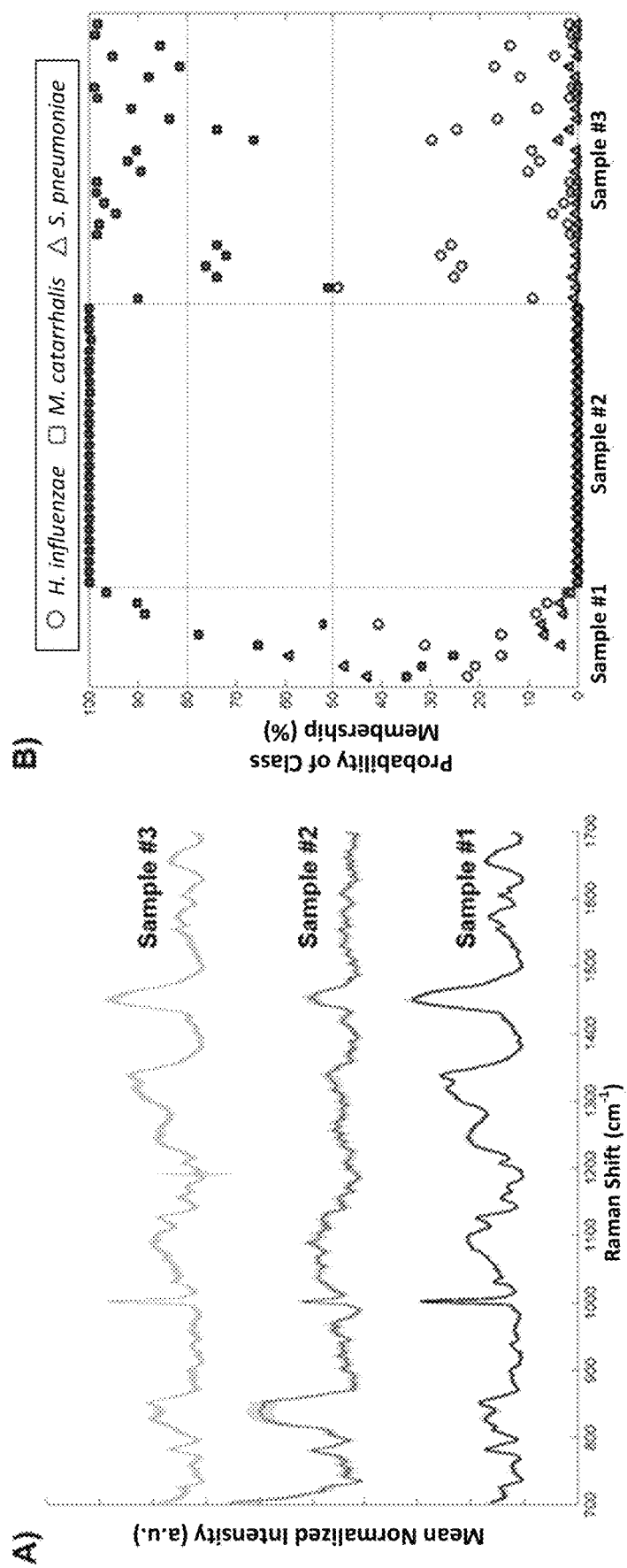
FIG. 28 shows (A) mean±standard deviation Raman spectra of bacterial colonies from clinical MEE samples cultured on MH agar and (B) posterior probability of class membership of clinical MEE samples to each of the three main pathogens that cause AOM, according to one embodiment of the invention.

Clinical MEE samples (n=3) were also analyzed based on the spectral characterization of *H. influenzae, M. catarrhalis*, and *S. pneumoniae* (FIG. 28). As shown in FIG. 28A, mean normalized Raman spectra with standard deviation of MEE samples presented distinct biochemical features used to identify bacteria involved in a MEE sample. After culturing both MEE samples, only one bacterial colony grew from MEE sample No. 1. For MEE sample No. 2, 27 spectra were collected across three bacterial colonies. The classification of a bacterial colony belonging to one or more of the three main pathogens that cause AOM was based on spectral characterization of these bacteria, which was utilized for SMLR analysis as shown in FIG. 27A. The probability of a MEE sample spectrum belonging to one or more bacteria was analyzed using a posterior probability plot (FIG. 28B) and summarized in Table 7. The first two Raman spectra of MEE sample No. 1 were not classified since their classification probability was below the threshold of 50%. All three MEE samples showed high probability of belonging to *M. catarrhalis* according to both Raman spectroscopy (Table 7) and based on features identified from colony morphology using the standard hockey puck test[27] and light microscopy. These findings show the potential of non-invasively identifying microorganisms from bacteria involved in MEE samples.

TABLE 7

Probability of each clinical MEE sample involving one or more of the three main bacteria that cause AOM.

| λ = 1.0, 50% Threshold | Sample No. 1 | Sample No. 2 | Sample No. 3 |
| --- | --- | --- | --- |
| Probability of *H. influenzae* | 0% | 0% | 0% |
| Probability of *M. catarrhalis* | 67% | 100% | 100% |
| Probability of *S. pneumoniae* | 11% | 0% | 0% |

Discussion

Current methods to diagnose OM rely primarily on visual assessment and focus on predicting the presence of fluid in the middle ear space. The challenge is distinguishing whether there are active bacteria causing an acute infection (AOM) or only effusion, which is rarely caused by a bacterial infection (OME). Antibiotic treatment should only be prescribed for patients with AOM and not OME since they target a broad range of active bacteria. The inability to determine the presence and identity of bacteria causing AOM has led to an over prescription of antibiotics, leading to antibiotic-resistant bacteria [28]. These antibiotic-resistant bacteria along with development of biofilms in the middle ear mucosa lead to the development of chronic OM infections. Action to investigate the middle ear effusion for bacterial identification is rarely practiced, serving as a last resort, and may be misleading due to obtaining negative cultures [29-31]. A method that can characterize and classify bacteria that cause AOM will provide physicians with information on bacteria involved in an ear infection, allowing them to prescribe more targeted antibiotics and reducing antibiotic resistance. This paper focuses on determining the feasibility of using RS to discriminate between the three main bacteria that cause AOM, *H. influenzae, M. catarrhalis*, and *S. pneumoniae* by characterizing their biochemical signatures. Preliminary findings show promise for implementing this technique as an in vivo diagnostic tool.

Prior to investigating bacteria using RS, it was important to first select a culture agar medium that would be able to grow all three of the main bacteria that cause AOM while minimizing agar spectral contribution within the typical fingerprint window (700-1800 $cm^{-1}$). Although chocolate agar is one of the most common agar types to use for culturing bacteria, it absorbs light much more strongly as an opaque medium compared to a translucent medium such as MH agar. This resulted in Raman spectra with higher noise and made it more challenging to discern certain spectral peaks as shown in FIG. 26. While *M. catarrhalis* and *S. pneumoniae* can grow in other agar types, *H. influenzae*, a fastidious organism, requires hemin and NAD to grow, which is released from the lysed RBCs as part of the chocolate agar media. Therefore, these factors were added to MH agar to grow *H. influenzae*. Spectral features of bacteria grown in MH agar as shown in FIG. 26 can be easily identified with lower spectral noise compared to the same bacteria grown in chocolate agar. Spectral contribution of MH agar was minimal compared to the spectral features found in the main bacteria that cause AOM. Signal from underlying culture media has been investigated with the goal of minimizing incubation time while still obtaining spectral features from bacteria of interest. Although this was not the goal of this paper, Maquelin et al. investigated the potential of identifying bacteria in agar within 6 hours post-culture [18]. Since colonies from that study were about 10-100 μm in diameter and limited in thickness, there was an overwhelming signal from the underlying culture medium interfering with strain identification. Therefore, they developed and applied a vector correction algorithm on first derivative spectra to remove signal contributions from culture medium in bacterial microcolonies. Although this method may be applied for known bacteria, clinical samples may take more than 6 hours to culture and involve polymicrobial infections, which may limit the application of this algorithm.

According to embodiments of the invention, the characterization and identification of the three main pathogens that cause AOM using Raman spectroscopy are reported. As can be seen in FIG. 27A, the SMLR feature importance (SMLR-FI) algorithm extracted specific spectral features critical for identification. A threshold of at least 25% importance was set to present more important biomarkers used for classification. The nontypeable *H. influenzae* (NTHi) strain showed 100% sensitivity and specificity. The biomarker with the highest SMLR-FI used for identification of *H. influenzae* was at 783 $cm^{-1}$ (Cytosine, uracil ring stretching). Identification of *M. catarrhalis* in MH agar was found with 89% sensitivity and 100% specificity. As can be seen from FIG. 27B, three spectral measurements fell below 50% for the probability of belonging to specific bacteria class (*H. influenzae, M. catarrhalis*, and *S. pneumoniae*). This may be due to phase variation in bacteria, which alters protein expression in different regions of a bacterial population. One example of phase variation commonly seen in *M. catarrhalis* is the UspA1 protein, which affects adherence factors that facilitate adhesion to other cells and surfaces [32]. This type of phase variation has been shown to occur in an in vitro environment when individual colonies were tagged using monoclonal antibodies for the UspA1 protein [33]. Although there may have been phase variation between *M. catarrhalis* colonies, multiple spectral features were identified for classifying the bacteria. The spectral feature identified to be the most important for classification of *M. catarrhalis* using SMLR-FI was 1431 $cm^{-1}$ (symmetric $CH_2$ bending and wagging). Classification for the third main bacteria that causes AOM, *S. pneumoniae*, presented a 100% sensitivity and 89% specificity. As can be seen from FIG. 27A, the most important spectral marker for discrimination of *S. pneumoniae* was at 840 $cm^{-1}$, which is tentatively assigned as pyranose, a sugar commonly found in the cell wall structure of bacteria [34]. This sugar may be found more predominantly in peptidoglycan from Gram-positive bacteria, such as *S. pneumoniae*, and may be important for determining bacterial susceptibility [34].

The spectral characterization of the main bacteria that cause AOM was used to identify those same bacteria involved in MEE from patients suffering from recurrent OM. This proof of concept approach was able to identify bacteria from cultured MEE samples (n=3). For MEE sample No. 1, only 9 spectra were collected since only one bacterial colony grew post-culture from this sample. Although two of the spectra collected from sample No. 1 had a probability of less than 50% for belonging to a specific type of bacteria, the remaining 7 spectra had at least a 50% chance of belonging to *M. catarrhalis*. For MEE samples No. 2 and No. 3, 100% of the 27 spectra collected were categorized as *M. catarrhalis*. Overall, nearly 80% of Raman spectra collected across all clinical MEE samples had an 80% or above probability of belonging to *M. catarrhalis*. These results were also supported by a hockey puck test [27], which uses a sterile wooden stick to push the colonies across the MH agar plate. The bacterial colonies easily slid across the agar plate, which indicated a positive outcome for *M. catarrhalis*. A major challenge for bacterial identification from clinical samples is the difficulty associated with culturing bacteria. This is more frequently presented with bacteria immersed in a biofilm environment, which limits the ability to culture particular clinical samples. Ultimately, the inability to culture bacteria in a biofilm state may limit the diagnosis of bacteria involved in chronic infections. This drawback highlights the importance of being able to detect the presence and identity of bacteria in clinical environments without the need to culture the bacteria. The potential impact of this solution may increase bacterial identification accuracy and decrease diagnostic time and cost.

The findings from characterizing the biochemical features of the three main otopathogens that cause AOM and accurately identifying them shows the potential application of RS as a diagnostic tool for patients suffering from OM. While additional bacteria species and isogenic variants that cause AOM will need to be interrogated, spectral identification and classification of the three main bacteria that cause AOM is a critical first step for developing a diverse spectral database to accurately detect and identify bacteria causing AOM. This work sets the stage for other applications of RS where bacterial identification may also be utilized as a research tool to investigate bacterial growth patterns, antibiotic susceptibility, or characterize biochemical changes in mutant forms of bacteria. Spectral results from these experiments may serve to create a better understanding of the microbial pathogenesis of other clinical bacterial infections. These studies provide insight into the biochemical changes occurring at the micro-scale and portends to the global application of this technique for the development of targeted antibiotics for susceptible and antibiotic-resistant bacteria. Numerous reports have been published recently describing the effects of over-prescription of broad-spectrum antibiotics and prescriptions of antibiotics for pathogens causing AOM that are no longer susceptible to them [28, 35-38]. This is a major problem that has led to antibiotic resistance in many bacteria and even multi-drug resistant (MDR) microorganisms. Providing a rapid technique that accurately detects and identifies pathogens causing AOM will aid in OM diagnostic efforts and inform physicians on proper treatment.

Example 5

Raman Microspectroscopy of *Staphylococcus Areus* Mutants Reveals Biochemical Features Important for Discrimination of Drug-Resistant Strains Healthcare-associated infections (HAIs), infections that patients obtain while receiving medical or surgical treatment in a healthcare facility, are a major threat to patient health. The most common HAIs in U.S. acute care hospitals include but are not limited to *pneumoniae*, surgical site infections, bloodstream infections, and gastrointestinal illness. Within surgical complications, wound infections have been found to account for 29% of these events and over 10% of all adverse events described in a study. Furthermore, HAIs have led to high rates of morbidity and mortality with annual costs of nearly $45 billion.

HAIs caused by *Staphylococcus aureus* (also notated as *S. aureus*) are of particular interest since they are a major burden to U.S. hospitals and specifically high-risk patients. Patients in hospitals with an *S. aureus* infection experienced a three times longer hospital stay, three times the amount of total charges, and five times the risk of in-hospital death compared to patients that did not have this type of infection. The developments of antibiotic-resistant strains such as methicillin-resistant *S. aureus* (MRSA) have further contributed to this growing problem by creating an additional barrier for treatment.

Methicillin resistance is mediated by the *staphylococcus* cassette chromosome (SCC mec), which encodes for penicillin binding protein PBP2a. Although the number of nosocomial infections by *S. aureus* increased by 62% per year, the number of MRSA infections in hospitals increased by 119% per year from 1999-2005. This rapid increase in antibiotic resistance motivates the need for pathogen surveillance for early detection of outbreaks in hospital and community associated infections.

In addition to antibiotic resistance, persistent infections are a major threat for patients suffering from acute and chronic illnesses. One subpopulation of bacteria that causes persistent infections are bacterial variants of *S. aureus* called small colony variants (SCVs), which display increased tolerance to particular classes of antibiotics such as aminoglycosides and therefore often arise in response to therapeutic intervention. These SCVs, which take on fastidious growth requirements, present with a phenotype different from their parent strain including colonies with decreased pigmentation that are approximately one-tenth the size of wild-type *S. aureus*.

The current approach for bacterial detection and identification in clinical samples involves a multi-step process to evaluate specific targets of the sample. Typically, samples are cultured on blood agar and characterized based on morphological features as seen through microscopy and biochemical tests. In addition, identification of bacteria at the species level and determination of antibiotic susceptibility requires additional targeted biochemical testing since specificity is critical for proper diagnosis and treatment. These techniques are time-consuming due to incubation times and subsequent manual tests requiring interpretation of biochemical reactions. In addition to atypical colony morphologies presented by SCVs, they also typically produce a reduction in biochemical reactions affecting identification tests and ultimately making it more challenging for clinical microbiologists to detect and identify SCVs. Current methods to detect and identify SCVs involves the application of extended culture periods and various biochemical assays, which may be difficult to interpret due to the altered biochemical reactions by SCVs. Furthermore, the gold standard for determining whether bacteria are susceptible/resistant to specific antimicrobials is through antimicrobial susceptibility testing (AST), which tests the isolated bacteria with various antimicrobials for growth inhibition. Specific strategies that promoted growth and minimized reversion to normal colony phenotypes have also been developed to test AST from *S. aureus* small colony variants (SCVs), commonly seen in chronic infections. Again, these approaches can be time-consuming, involve culture media with limitations, and challenging to interpret especially for mutant strains.

To obtain high specificity, researchers have mainly used polymerase chain reaction (PCR) to amplify deoxyribonucleic acid (DNA) from bacteria. However, PCR is dependent on target genes, which may not be available for specific bacterial mutants, vulnerable to contamination, and is not able to distinguish between live versus dead bacteria in a clinical sample. These factors negatively affect the sensitivity of PCR and how it can be used to accurately detect and identify bacteria at the species level and mutants. Therefore, there is a need for a rapid technique able to accurately detect and identify bacterial mutants and resistant strains to guide proper treatment.

Raman spectroscopy (RS), an inelastic light scattering technique, provides molecular specificity and has been used extensively for characterizing bacteria. Its ability to provide accurate and reproducible spectral information of the sample, perform measurements rapidly (seconds), and create a biochemical profile of a sample has paved the way for biological applications. In this article we focused on utilizing Raman microspectroscopy to distinguish different isolates of the same species and to determine if isogenic variants of *Staphylococcus aureus* could be distinguished in situ using regional spectral analysis.

*Staphylococcus aureus* is a leading cause of hospital-acquired infections, including bacteremia, pneumonia, and endocarditis. Treatment for these types of infections can be challenging because mutant bacterial strains of *S. aureus*, such as methicillin-resistant *S. aureus* (MRSA), have evolved resistance to antimicrobial drugs. Current methods to identify infectious agents in hospital environments often rely on time-consuming, multi-step culturing techniques to distinguish problematic strains (i.e., antimicrobial resistant variants) of a particular bacterial species. In this exemplary embodiment, the ability to characterize and identify microbes at the subspecies level using Raman microspectroscopy is demonstrated, which probes the vibrational modes of molecules to provide a biochemical "fingerprint". According to the embodiments of the invention, this technique can be utilized to distinguish between different isolates of species such as *Streptococcus agalactiae* (also notated as *S. agalactiae*) and *Staphylococcus aureus*. In certain embodiments, this technique is applied towards the analysis of isogenic variants of *Staphylococcus aureus* including the comparison of strains lacking or expressing particular antibiotic resistance determinants. These spectral profiles presented variations in biochemical components such as amino acids, carotenoids, and lipids. Mutants lacking carotenoid production were distinguished from wild-type (WT) *S. aureus* and other strain variants. Furthermore, spectral biomarkers of these *S. aureus* isogenic bacterial strains were identified. In total, these results demonstrate the feasibility of using Raman microspectroscopy to distinguish between various mutant forms of a single bacterial species in situ, which is important for detecting antibiotic resistant strains of bacteria. This technique may be expanded to include the identification of other multi-drug resistant (MDR) pathogens.

Bacterial Strains:

Multiple pathogens were probed to determine their biochemical profile using Raman microspectroscopy and determine if clinically relevant strains could be identified. The following bacteria were evaluated to highlight spectral differences captured using Raman microspectroscopy: a.) wild-type *Staphylococcus aureus* (JE2), b.) *Streptococcus agalactiae* also known as Group B *Streptococcus* (GBS) strains GBS 1084 and GBS 37, and nontypeable *Haemophilus influenzae* (ATCC No. 49766).

*S. aureus* mutants were also investigated using Raman microspectroscopy. One of these included AmecA, which encodes for resistance to non-β-lactam antibiotics and is responsible for methicillin-resistant *S. aureus* (MRSA). The second *S. aureus* mutant investigated was AispA, a geranyl-transferase gene, which generates non-pigmented bacterial colonies. The third *S. aureus* gene studied, fntA, is a member of the *S. aureus* core cell wall stimulon and inactivation offifmtA (AfmtA) affects the cell wall structure and diminishes the ability of *S. aureus* to form biofilms. The fourth *S. aureus* mutant, ΔSAUSA300_0918, encodes for glycero-lipid metabolism and is involved in the formation of membrane glycolipids. The Raman spectra of each of these mutants were compared to JE2, the methicillin-resistant parental strain from which they were derived. *S. aureus* small colony variants (SCVs) were also examined to determine if Raman characterization could be used to biochemically discriminate this type of antibiotic-tolerant variant from other *S. aureus* strains. The SCVs tested included a cytochrome double knockout strain Δcyd Δqox as well as a heme biosynthesis-deficient strain ΔhemB and a menaquinone biosynthesis-deficient strain ΔmenB. The Raman spectra of each of these mutants were compared to Newman, the methicillin-sensitive parental strain from which they were derived.

Each strain was streaked onto Mueller-Hinton (MH) agar, which was prepared by suspending 11 g of MH (BD, Franklin Lakes, N.J.) powder and 7.5 g (15% agar/L) of agar (Thermo Fisher Scientific, Waltham, Mass.) in 500 mL of distilled water while heating (180° F.) and stirring. The mixture was then autoclaved at 121° C. for 10 minutes. After plating, bacteria were incubated for 24 hours at 37° C.

Raman Microspectroscopy:

Acquisition of Raman spectra was performed using a confocal Raman microscope (inVia Raman Microscope, Renishaw plc, Gloucestershire, UK) with a 785 nm laser diode (Renishaw plc, Gloucestershire, UK). To interrogate the bacterial colonies, a 100× (N PLAN EPI, NA=0.85, Leica, Weltzlar, Germany) objective was used to focus a ~1 µm laser spot directly on the bacterial colony on the agar surface at 27 mW. Raman scattered light was detected through the same objective, then passed through a 35 µm slit and dispersed by a holographic grating (1200 lines/mm) onto a thermoelectrically cooled (−70° C.) deep-depleted, CCD that provided about 1 $cm^{-1}$ spectral resolution. System alignment and light throughput to the sample was confirmed before and after experimental measurements with an internal silicon standard at 520 $cm^{-1}$ and laser power at the sample.

Spectral measurements included three acquisitions per spot, three spots per colony, and three colonies per bacteria for *S. aureus* mutants. Measurement parameters for SCVs included three spots per colony and three colonies per bacterial strain. Spectral acquisition parameters included a 30 second photobleach followed by a 15 second exposure with 7 accumulations from 700-1800 $cm^{-1}$. Cosmic ray removal from collected Raman spectra was performed using a custom MATLAB script (Mathworks, Natick, Mass.). Raman spectra were then processed to remove background fluorescence using a least squares modified polynomial fitting algorithm and smoothed for noise with a second-order Savitsky-Golay filter. To optimize background fluorescence subtraction, each raw spectrum from small colony variants (SCVs) was divided into three segments. These segments included: i) 600-1141 $cm^{-1}$ ii.) 1141-1477 $cm^{-1}$ and iii.) 1470-1700 $cm^{-1}$. The 7 $cm^{-1}$ overlap of regions ii.) and iii.) was adjusted by using only the fitting from 1478-1700 $cm^{-1}$ for region iii.). Segment i.) used an $8^{th}$ degree modified polynomial fitting compared to segments ii.) and iii.), which implemented a $5^{th}$ degree modified polynomial fit for fluorescence subtraction. After spectral processing was performed for SCV data, spectral segments were reconstructed into one Raman spectrum for each measurement. Post-processed spectra were mean normalized to each individual Raman spectrum for comparative analysis.

Spectral Data Analysis:

Mean normalized Raman spectra of bacterial colonies were analyzed to determine classification. For preliminary analysis, peak ratios were calculated based on distinct Raman peaks and the phenylalanine peak across all *S. aureus* mutants and SCVs. Peak ratio comparisons were calculated using a one-way analysis of variance (ANOVA) and plots are shown using a 95% confidence interval. To limit bias from hand-selecting peaks, a full-spectrum principle components analysis (PCA) was performed on the same two sets of data. Since these data sets included more spectral features (variables) compared to observations, PCA scores and loadings were calculated using singular value decomposition (SVD). Implementation of SVD for PCA reduces the large volume of data and minimizes the loss of precision that is typically seen when using the covariance matrix approach. To use PCA via SVD, the means of the mean-normalized spectral data matrix of mean-normalized spectral data were subtracted from each dimension to center the data. Then, the SVD of the mean-centered matrix was calculated to determine the eigenvalues and eigenvectors to interpret the scores and loadings of the original input matrix.

While the full-spectrum analysis provided a global picture of the Raman data, we wanted to ensure the model was not over fitting the data since there were more spectral features than measurements. Therefore, loadings that were calculated from the PCA analysis were used to identify spectral regions of interest for downstream analysis. Our approach for determining these spectral regions of interest involved the following steps. First, the two maximum (absolute value) loadings from the first two PCs were identified. If the spectral region between any of those loadings peaks contained loading values that were at least 50% of the second maximum loading value and the region in consideration was not greater than 15% of the total features available (wavenumbers), then that spectral region could be used for evaluation. Otherwise, the spectral region of interest would be defined by the width of the peak determined by the PC loadings.

After the spectral regions were designated for both *S. aureus* mutants and SCVs, a discriminatory analysis was performed for each respective region. A variant of Fisher's linear discriminant analysis, quadratic discriminant analysis (QDA), was used to determine classification of *S. aureus* mutants or SCVs within each spectral region. First, a quadratic classifier was created based on designated classes (each of the *S. aureus* mutants and SCVs) and the PCA scores. Next, the coefficients of the respective quadratic boundaries were determined. The coefficients (K, constant; L, linear; Q, quadratic) were used in equation 1 to generate the curves to determine boundaries for discrimination amongst classes for each *S. aureus* mutants and SCVs.

$$K + [x_1 \quad x_2]L + [x_1 \quad x_2]Q\begin{bmatrix}x_1\\x_2\end{bmatrix} = 0 \quad (2)$$

Figure 29:
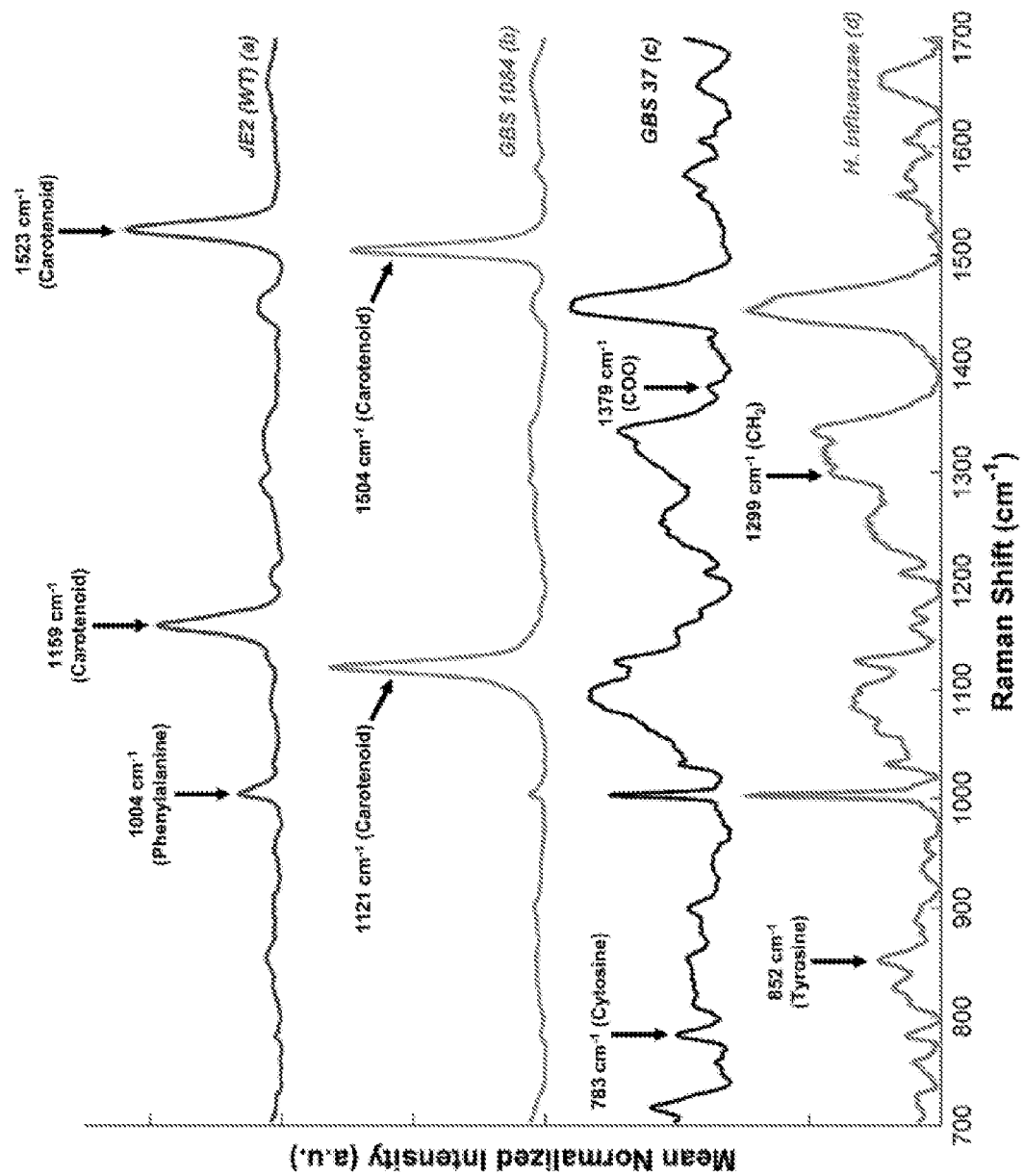
FIG. 29 shows mean±standard deviation Raman spectra of various bacteria. Spectral signatures of bacteria shown include (a) *Staphylococcus aureus* JE2 (wild-type), (b) *Streptococcus agalactiae* 1084, also known as group B streptococcus (GBS), (c) GBS 37, and (d) *Haemophilus influenzae*. Different spectral features are identified for each bacterial measurement.

RS can Differentiate Two Different Virulent Strains of GBS:

Raman microspectroscopy was used to characterize and differentiate various bacterial species (FIG. 29A). Wild-type *S. aureus* presented two main peaks at 1159 cm$^{-1}$ and 1523 cm$^{-1}$ initially predicted to be due to the carotenoid family. In previous work, we characterized *Haemophilus influenzae*, one of the three main bacteria that causes acute otitis media. Raman analysis of *H. influenzae* presented distinct Raman features highlighted by tyrosine (852 cm$^{-1}$) and CH$_2$ fatty acids deformation (1299 cm$^{-1}$) compared to the other bacterial spectra (FIG. 29D). In addition to these bacteria, two strains of *Streptococcus agalactiae*, commonly known as group B *Streptococcus* (GBS), were spectrally measured. GBS 1084 showed two unique peak at 1121 cm$^{-1}$ and 1504 cm$^{-1}$ due to a carotenoid (FIG. 29B). Various biochemical features could be identified in GBS 37 that included cytosine (783 cm$^{-1}$), phenylalanine (1004 cm$^{-1}$), and C—O—O symmetric and asymmetric stretching in peptidoglycan (1379 cm$^{-1}$) (FIG. 29C). The dramatic spectral differences between the two strains of GBS, *H. influenzae*, and JE2, indicated that other clinically relevant isolates could potentially be distinguished at the subspecies level using Raman microspectroscopy. This finding motivated the application of this technique to discriminate single gene mutations in *S. aureus* mutants.

Figure 30:
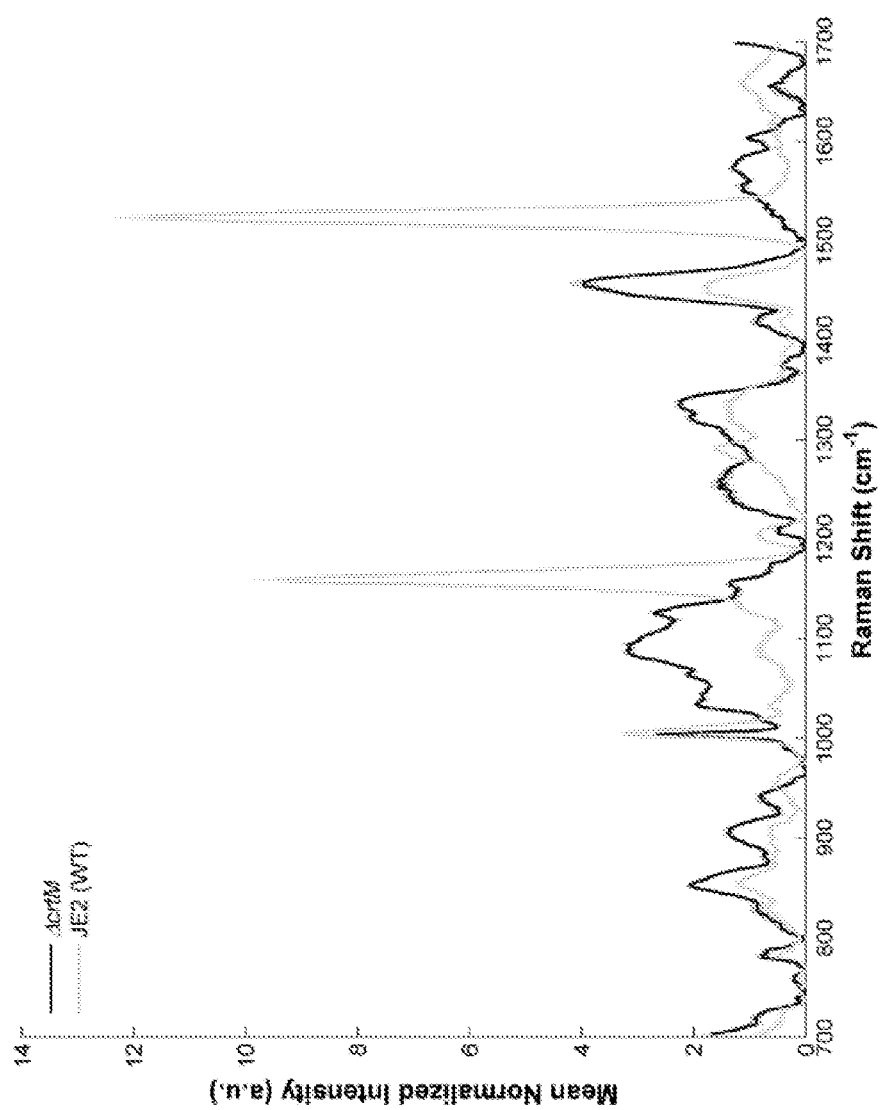
FIG. 30 shows mean±standard deviation Raman spectra of *Staphylococcus aureus* JE2 (wild-type) and ΔcrtM, a *S. aureus* mutant that lacks pigmentation. The biochemical features that give rise to pigmentation in JE2 are due to staphyloxanthin, located at 1159 and 1523 $cm^{-1}$.
Figure 31:
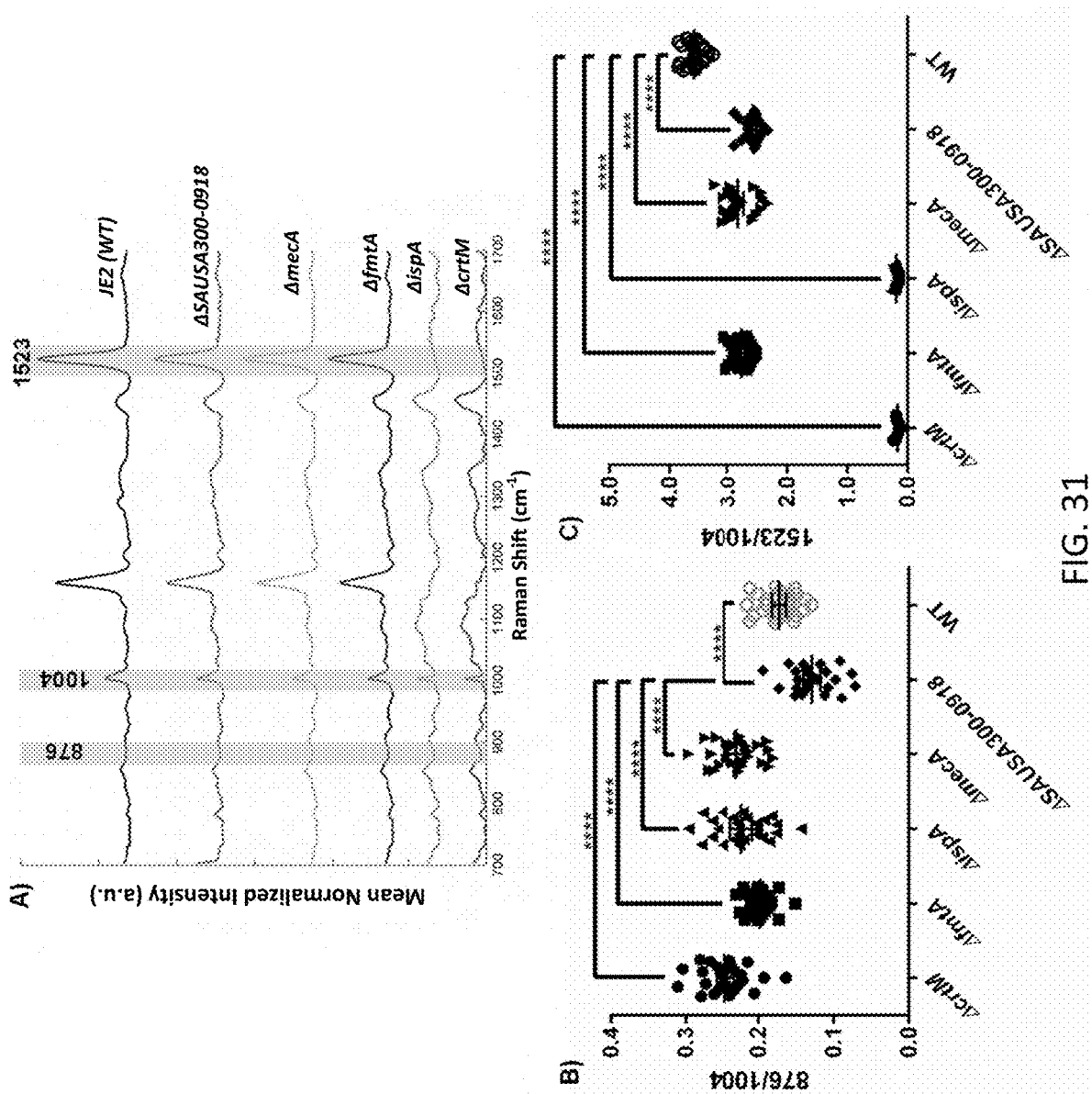
FIG. 31 shows comparison of *S. aureus* mutants based on carotenoid and lipid membrane features. (A) Mean±standard deviation Raman spectra of WT and *S. aureus* mutants. (B) Mean peak ratio of 1458 $cm^{-1}$ (lipid?) and 1004 $cm^{-1}$ (phenylalanine) with 95% confidence interval calculated using a one-way ANOVA performed to compare mutants vs. WT. ****=$p<0.0001$. (C) Mean peak ratio of 1523 $cm^{-1}$ (carotenoid)

Single Gene Mutated Strains are Distinguished from WT:

To test the feasibility of using Raman microspectroscopy to distinguish between single gene mutations, Raman spectra from a *S. aureus* ΔcrtM mutant were analyzed. This mutant was chosen as a positive control since deletion of crtM disrupts biosynthesis of the carotenoid staphyloxanthin, which is responsible for the golden pigment of *S. aureus* and predicted to contribute to the two main *S. aureus* Raman peaks at 1159 cm$^{-1}$ and 1523 cm$^{-1}$. Absence of these Raman peaks in the ΔcrtM mutant confirmed that they belonged to this specific carotenoid pigment (FIG. 30). The parental strain in which this mutant was derived, *S. aureus* JE2, presented two major Raman peaks at 1159 and 1523 cm$^{-1}$, which correspond to carotenoids and are not present in the ΔcrtM strain. These carotenoids are not only an important factor for the cell membrane's integrity, but also play a role in the virulence of *S. aureus*. Another mutant chosen for this study included AispA, an unpigmented *S. aureus* strain predicted to display a similar Raman profile to that of ΔcrtM due to the lack of staphyloxanthin production. The profile of this mutant was virtually indistinguishable from that of ΔcrtM. Finally, to assess whether a unique lipid signature could be detected in *S. aureus* using Raman microspectroscopy, ΔSAUSA300_0918, (a putative lipid metabolism mutant) was compared to the parental strain. To quantify visually different Raman peaks of the *S. aureus* mutants, peak ratios of the mean-normalized intensities highlighted in gray bands were calculated (FIG. 31A). Evaluation of the lipid mutant strain (ΔSAUSA300_0918) was performed using a peak ratio of 876/1004 (asymmetric stretching N$^+$ (CH$_3$)$_3$/phenylalanine). The Raman peak at 876 cm$^{-1}$ has been shown to be relevant in characterizing membrane lipids, specifically phosphatidylcholine. A peak ratio of these biochemical features presented a significant (p<0.0001) decrease for ΔSAUSA300_0918 when compared to *S. aureus* mutants and JE2 (FIG. 31B). Since this gene is part of the glycerolipid metabolism pathway in *S. aureus*, deletion of the gene could alter lipid production related to cell wall composition.

To determine the differences in pigmentation in the *S. aureus* mutants, the peak ratio of 1523/1004 (carotenoid/phenylalanine) was analyzed. A peak ratio of these biochemical features identified a statistically significant (p<0.0001) increase in pigmentation due to staphyloxanthin when JE2 was compared to AispA, ΔcrtM, and the other *S. aureus* mutants (FIG. 31C). Peak ratio results were comparable between AispA and ΔcrtM, which confirms their lack of pigmentation production due to the genetic mutation. These results confirmed the spectral features at 1159 cm$^{-1}$ and 1523 cm$^{-1}$ to be carotenoids relative to JE2.

In total, these data confirm the ability of Raman microspectroscopy to interrogate bacterial colonies and distinguish between two strains of *S. aureus* based on a one-gene mutation. The findings with the unpigmented strains and the mutant with altered lipid biosynthesis indicate that detection of other single gene mutations, including antibiotic resistance genes, might be possible.

Figure 32:
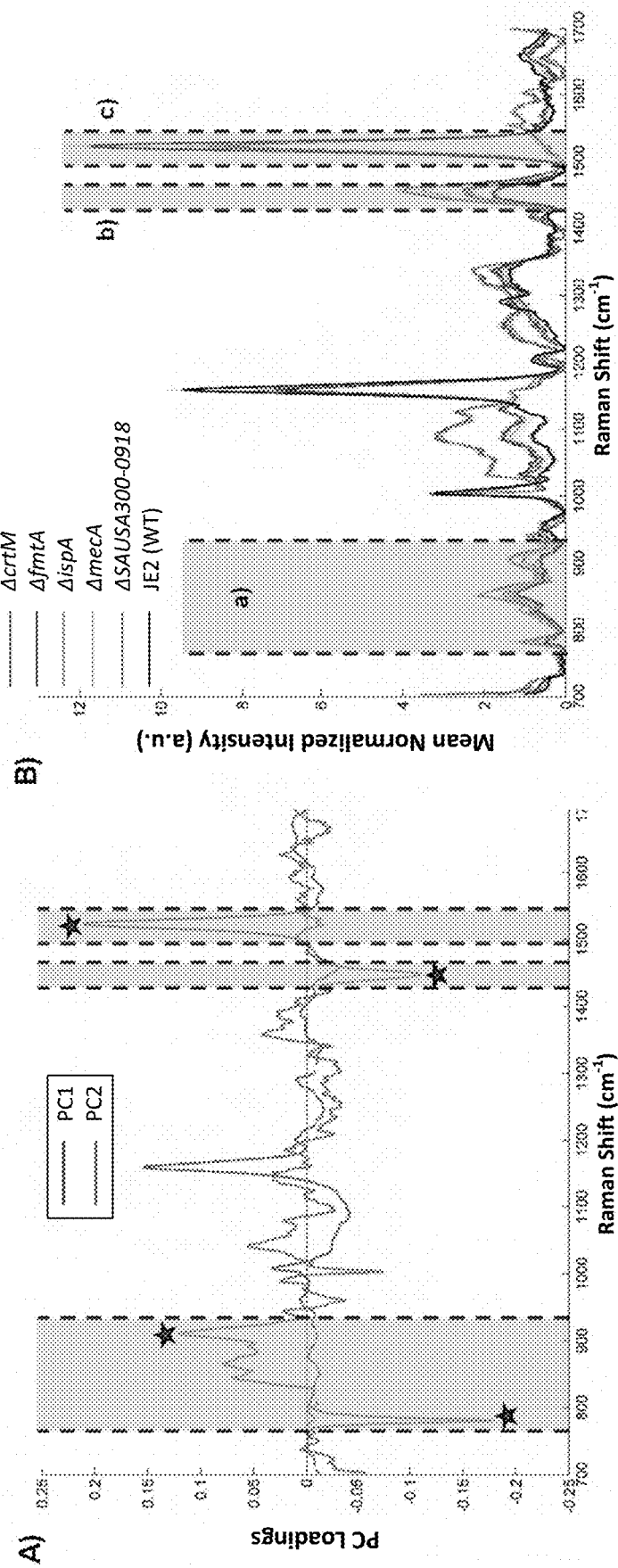
FIG. 32 shows spectral region analysis of *S. aureus* mutants based on PC loadings. (A) Gray bands identify spectral regions for further analysis of WT and *S. aureus* mutants as determined by PC loadings. Stars mark maximum PC loading values for PC1 and PC2. (B) Spectral regions (gray bands) to be used for discriminant analysis of the *S. aureus* mutants and WT.

Antibiotic Resistant *S. aureus* Strains can be Identified Using RS:

Clinically-relevant applications for this technology were assessed by comparing methicillin-sensitive mutants ΔmecA and ΔfmtA to their methicillin-resistant parental strain using Raman microspectroscopy. A full-spectrum analysis of *S. aureus* mutants using PCA showed separation between the unpigmented strains (ΔcrtM and AispA), methicillin-sensitive strains (ΔmecA and ΔfmtA), ΔSAUSA300_0918, and JE2. To avoid overfitting the 917 spectral features evaluated with respect to the 162 spectra that were collected of the six mutants, the loadings from principal component one (PC1) and PC2 were used to identify spectral regions of interest for analysis. The number of features or wavenumbers used for statistical analysis within these regions would be minimized using the PC loadings to further ensure the data were not overfit. The maximum PC1 loading was at 1523 cm$^{-1}$ and the second maximum PC1 loading was at 1159 cm$^{-1}$ (FIG. 32A). Since these two wavenumbers both described pigmented vs. unpigmented *S. aureus* mutants, the maximum PC1 was selected for analysis (1523 cm$^{-1}$). The maximum PC2 loading was located at 781 cm$^{-1}$ and the second maximum PC2 loading was at 910 cm$^{-1}$. The *S. aureus* mutants spectral regions for analysis were determined from the loadings of PC1 and PC2. The first spectral region of interest (a) was 765-934 cm$^{-1}$, which contained loading values that were at least 50% of the second maximum loading in PC2 (FIG. 32B). Since the second highest PC1 loading was not used for analysis, the next highest PC loading peak width, 1431-1464 cm$^{-1}$, was selected as the second spectral region of interest (b) (FIG. 32B). The third spectral region of interest (c) was 1495-1544 cm$^{-1}$, based on the maximum PC1 (1523 cm$^{-1}$) (FIG. 32B).

Figure 33:
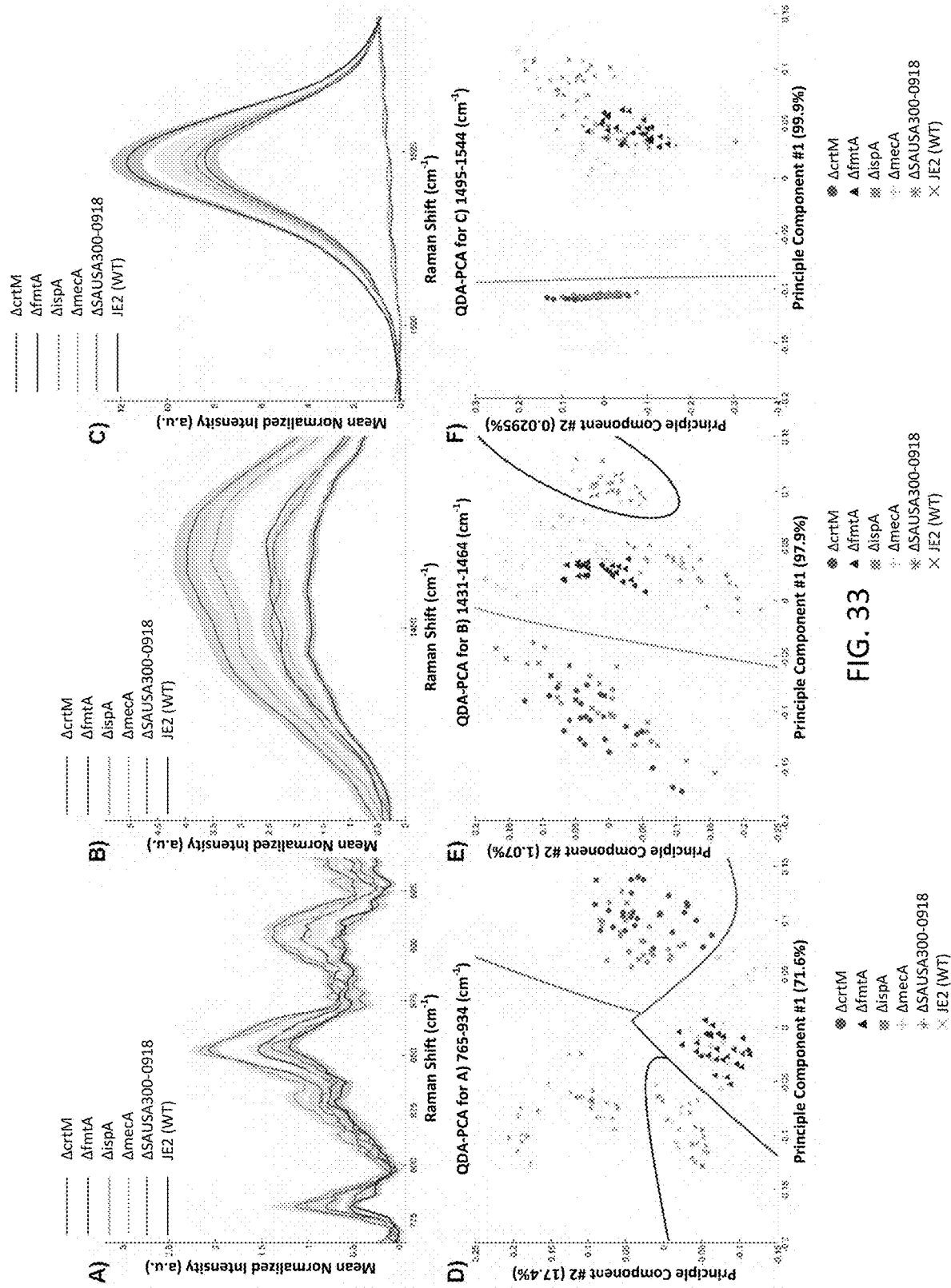
FIG. 33 shows spectral regions of interest and subsequent discriminant analysis for *S. aureus* mutants and WT. (A) Spectral region No. 1 (765-934 $cm^{-1}$). (B) Spectral region No. 2 (1431-1464 $cm^{-1}$). (C) Spectral region No. 3 (1495-1544 $cm^{-1}$). (D) Quadratic discriminant analysis (QDA) performed on the PCA scores for spectral region No. 1 of *S. aureus* mutants and WT. (E) Quadratic discriminant analysis (QDA) performed on the PCA scores for spectral region No. 2 of *S. aureus* mutants and WT. (F) Quadratic discriminant analysis (QDA) performed on the PCA scores for spectral region No. 3 of *S. aureus* mutants and WT. *** italicize mutant.

A quadratic discriminant analysis (QDA) analysis using PCA-SVD of each of the spectral regions of interest was implemented to determine discrimination amongst the *S. aureus* mutants. For the first spectral region of interest for *S. aureus* mutants (765-934 cm$^{-1}$) each of the WT strain, ΔSAUSA300_0918, non-pigmented strains, and methicillin-sensitive strains were successfully discriminated (FIG. 33D). These results were based on using PC1 and PC2, which explained 71.6% and 17.4% of the data within this spectral region, respectively. Within this first spectral region, there were various biochemical features such as cytosine (782 cm$^{-1}$), tyrosine (853 cm$^{-1}$), and C—O—C stretching and teicuronic acid (907 cm$^{-1}$) found in the cell wall of Gram-positive bacteria that played a role in characterizing each of the *S. aureus* mutants (FIG. 33A). The differences in Raman peak intensities for these biochemical features within this spectral region highlights biomarkers important for discrimination amongst these mutants.

The second spectral region of interest (1431-1464 cm$^{-1}$) showed discrimination between unpigmented strains, methicillin-sensitive mutants and ΔSAUSA300_0918, and WT. For this spectral region, PC1 and PC2 were used in the analysis, explaining 97.9% and 1.1% of the variance, respectively. The 33 cm$^{-1}$ width of this spectral region was dominated by the CH$_2$ deformations (1456 cm$^{-1}$) and was another feature that explained the biochemical differences amongst the *S. aureus* mutants. The third spectral region of interest for the *S. aureus* mutants (1495-1544 cm$^{-1}$) presented high discrimination between unpigmented strains and the rest of the strains that were analyzed. Within this spectral region of interest, PC1 and PC2 explained 99.9% and 0.0% of the variance in the data, respectively. The high percentage in explanation for PC1 is related to the dominating Raman peak known to be the carotenoid staphyloxanthin (1523 cm$^{-1}$). Since only two of the mutant strains were unpigmented, these were the only strains that could be distinguished amongst the other strains within this spectral region. Similar biochemical features resembling carotenoids have also been detected in *Mycoplasma pneumoniae* and were used for strain identification. The findings motivated us to compare spectral features of methicillin-resistant to methicillin-sensitive *S. aureus*.

Figure 34:
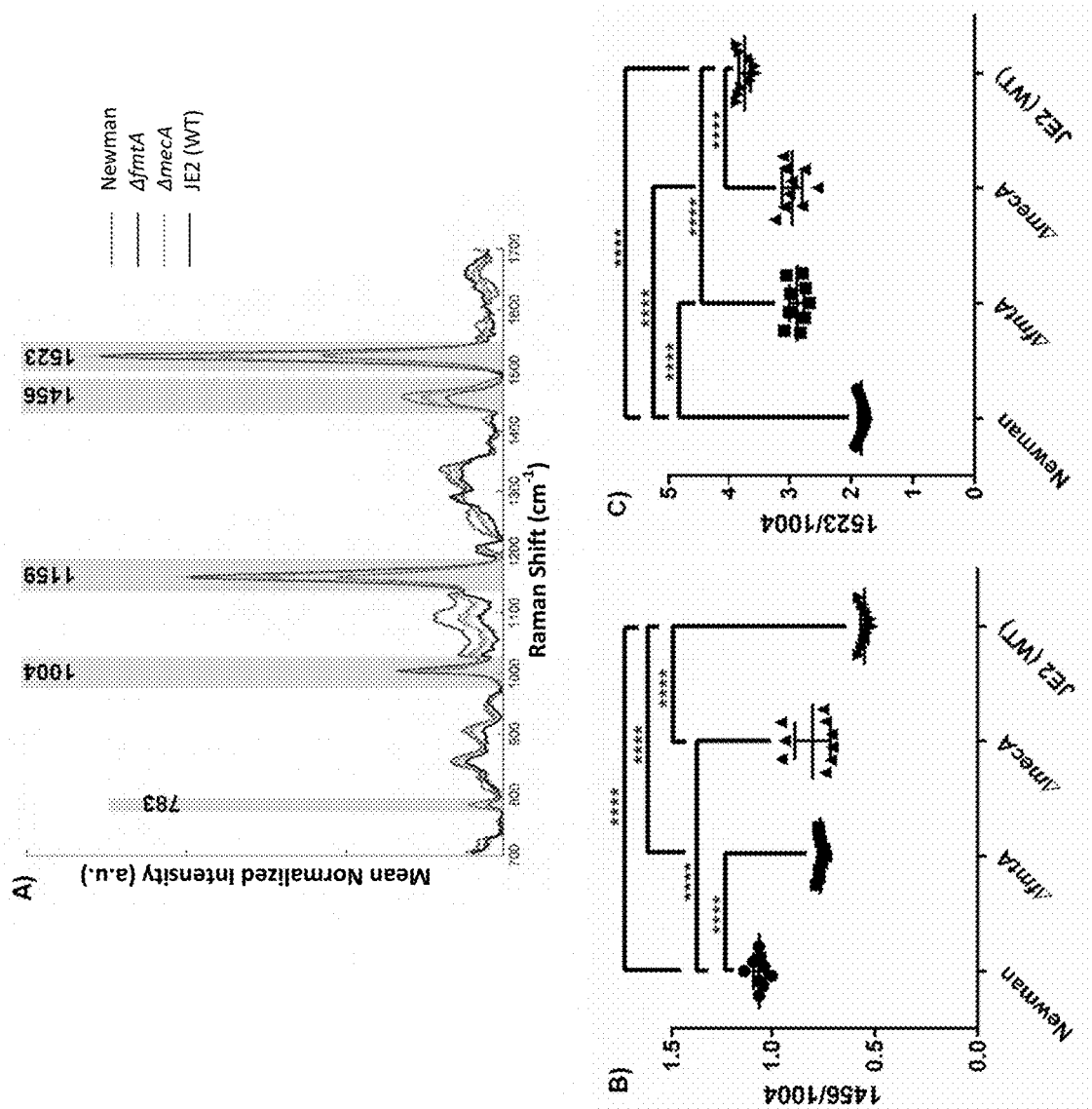
FIG. 34 shows comparison of *S. aureus* methicillin-sensitive, methicillin-resistant strains, and mutants. (A) Mean±standard deviation Raman spectra of Newman (wild-type methicillin-sensitive), ΔfmtA, ΔmecA, and JE2 (wild-type methicillin-resistant). (B) Mean peak ratio of 1456 $cm^{-1}$ ($CH_2$ deformations) and 1004 $cm^{-1}$ (phenylalanine) with 95% confidence interval calculated using a one-way ANOVA performed to compare mutants vs. JE2 and Newman. **=$p<0.0001$. (C) Mean peak ratio of 1523 $cm^{-1}$ (carotenoid) and 1004 $cm^{-1}$ (phenylalanine) with 95% confidence interval calculated using a one-way ANOVA performed to compare mutants vs. JE2 and Newman. **=$p<0.0001$.

For this initial comparison, JE2, a methicillin-resistant isolate of *S. aureus* was compared to Newman, a methicillin-sensitive *S. aureus* strain. From the Raman spectra of these strains, two major peaks can be easily identified at 1159 cm$^{-1}$ and 1523 cm$^{-1}$, both related to carotenoid features (FIG. 34A). Another peak that presented changes in intensity included 1456 cm$^{-1}$ (CH$_2$ deformations). Peak ratios of 1456 cm$^{-1}$ to 1004 cm$^{-1}$ were significantly (p<0.0001) lower for JE2 when compared to Newman (FIG. 34B). In addition, a peak ratio of 1523 cm$^{-1}$ to 1004 cm$^{-1}$ showed that JE2 was significantly (p<0.0001) greater when compared to Newman (FIG. 34C). This was similarly seen with the carotenoid peak at 1159 cm$^{-1}$. A decrease in pigmentation production is a characteristic phenotypical feature seen in small colony variants (SCVs). In addition, the Amide III-v(C—N) at 1290 cm$^{-1}$ is significantly greater in intensity compared to Newman. Furthermore, spectral intensity differences were seen in the previously described carotenoids (1159 cm$^{-1}$ and 1523 cm$^{-1}$) and CH$_2$ deformations (1456 cm$^{-1}$) when *S. aureus* mutants ΔfmtA and ΔmecA were compared to JE2 and Newman. These differences in the Raman spectra provided insight into biochemical factors that could be used to differentiate methicillin-sensitive from methicillin-resistant *S. aureus* strains.

Small Colony Variants (SCVs) could be Distinguished from Newman WT Strain:

Since our data strongly indicates that Raman microspectroscopy can distinguish biochemical signatures indicative of methicillin resistance or sensitivity in *S. aureus*, we sought to determine whether other types of antibiotic tolerance could be similarly identified. Therefore, we extended our analysis to that of the clinically relevant SCV phenotype. SCVs are intrinsically-resistant to aminoglycoside antibiotics. We compared the SCV phenotype conveyed by three different types of mutations to their parental strain, the methicillin-sensitive strain Newman. The SCV mutations chosen for this analysis were a double cytochrome deletion Δcyd Δqox, as well as the more clinically-relevant mutants lacking heme (ΔhemB) or menaquinone (ΔmenB) biosynthesis.

Figure 35:
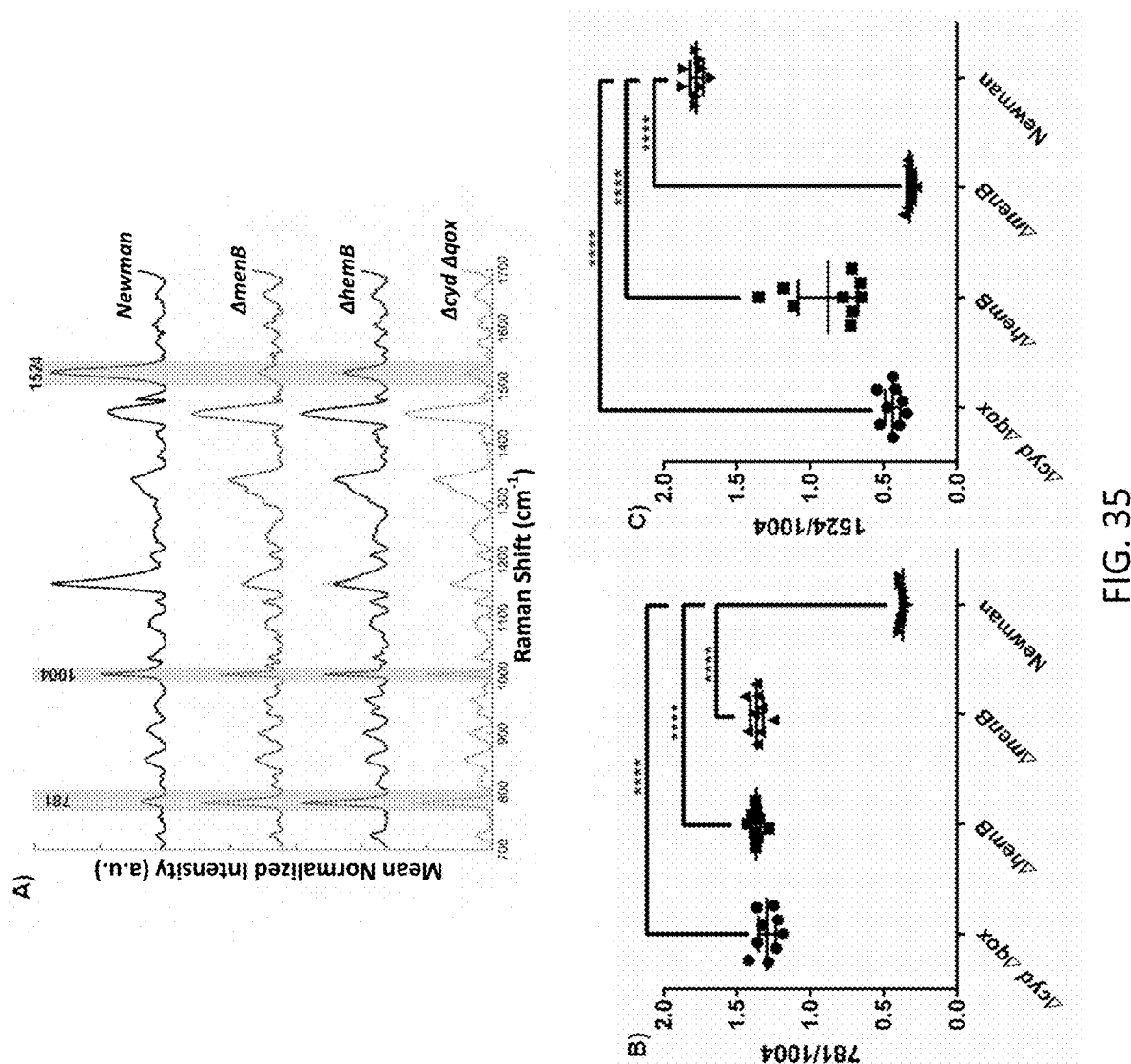
FIG. 35 shows comparison of small colony variants (SCVs) based on uracil and carotenoid features. (A) Mean±standard deviation Raman spectra of Newman and SCVs. (B) Mean peak ratio of 781 cm$^{-1}$ (uracil) and 1004 cm$^{-1}$ (phenylalanine) with 95% confidence interval calculated using a one-way ANOVA performed to compare mutants vs. Newman. **=p<0.0001. (C) Mean peak ratio of 1524 cm$^{-1}$ (carotenoid) and 1004 cm$^{-1}$ (phenylalanine) with 95% confidence interval calculated using a one-way ANOVA performed to compare mutants vs. Newman. **=p<0.0001.

Raman peaks of SCVs that were visually different are highlighted in gray bands and quantified using peak ratios (FIG. 35A). The first peak ratio of 781/1004 (uracil/phenylalanine) was significantly lower (p<0.0001) for Newman when compared to the other SCVs (FIG. 35B). Another peak ratio of interest was 1524/1004 (carotenoid/phenylalanine), which showed Newman as significantly higher Raman intensity (p<0.0001) compared to the other three SCVs (FIG. 35C). The lower Raman intensity at 1524 cm$^{-1}$ for the SCVs was expected since they produce a decreased amount of pigmentation compared to Newman.

Evaluation of the entire data set for SCVs using a full-spectrum analysis of SCVs using PCA showed variation based on PC1 (93.3%) and PC2 (2.21%) between Newman, Δcyd Δqox, ΔhemB, and ΔmenB. Following the same approach as the *S. aureus* mutants, the loadings from PC1 and PC2 of the SCVs were used to identify spectral regions for subsequent analysis. The maximum PC1 loading was located at 1524 cm$^{-1}$ and the second PC1 maximum loading was at 1159 cm$^{-1}$. These were the same Raman peaks that were identified from the *S. aureus* mutant data. Since both of these features were characteristic of carotenoids, only the maximum PC1 loading (1524 cm$^{-1}$) was used for spectral region analysis. It has been previously noted that SCVs are defective in their pigment production, so it is unsurprising that the carotenoid peaks provided a means of distinguishing this type of antibiotic tolerant mutant from WT strains. The second PC1 loading that was used for analysis included the third maximum feature at 781 cm$^{-1}$ The maximum PC2 loading for the SCV data was at 781 cm$^{-1}$ and the second maximum PC2 loading was at 1522 cm$^{-1}$. Since the both of these Raman peaks were previously selected from PC1, the third maximum PC2 loading located at 1019 cm$^{-1}$ was used for spectral region analysis. The spectral regions of the SCVs used for discriminatory analysis were based on these PC1 and PC2 loadings. The spectral regions identified for analysis of SCV data was 772-800 cm$^{-1}$ (region 1), 1012-1029 cm$^{-1}$ (region 2), and 1500-1558 cm$^{-1}$ (region 3).

Figure 36:
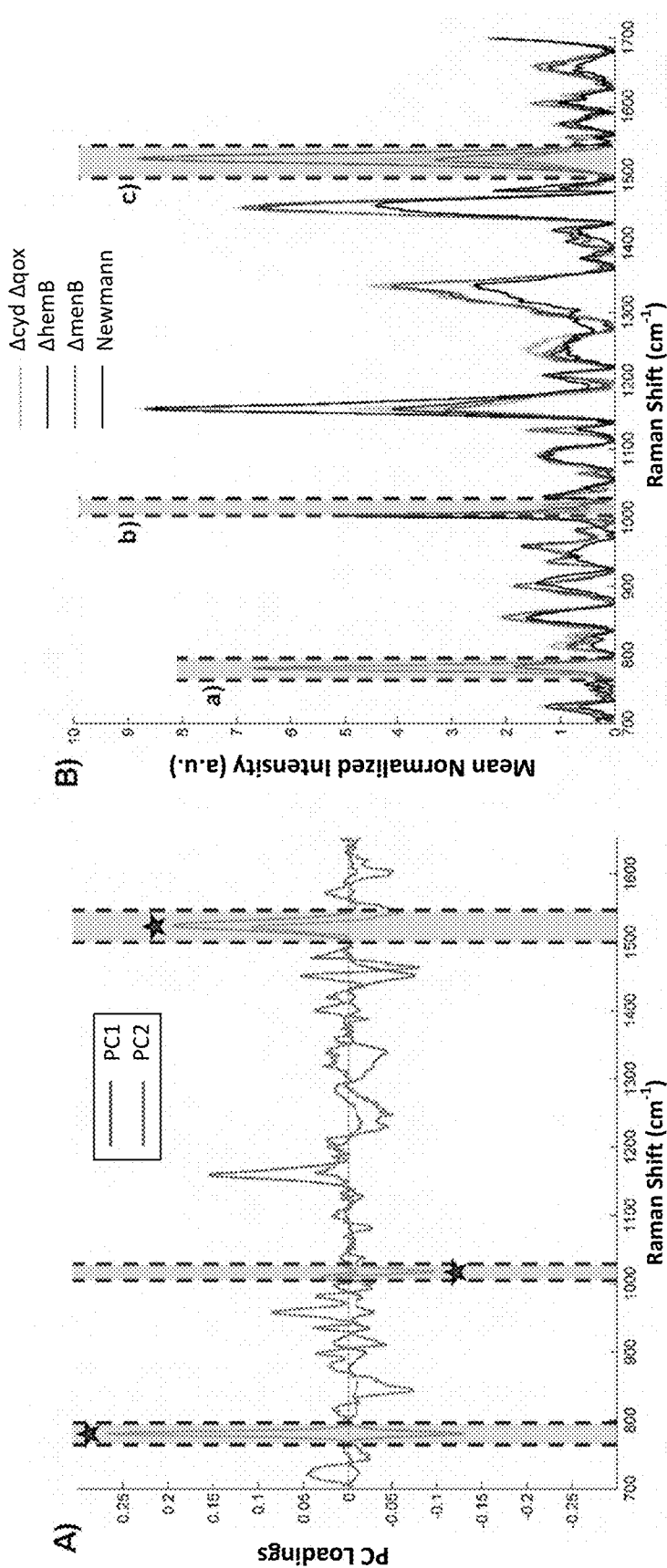
FIG. 36 shows spectral region analysis of small colony variants (SCVs) based on PC loadings. (A) Gray bands identify spectral regions for further analysis of Newman and SCVs as determined by PC loadings. Stars mark maximum PC loading values for PC1 and PC2. (B) Spectral regions (gray bands) to be used for discriminant analysis of the SCVs and Newman. *** italicize strain names and change to Newman.
Figure 37:
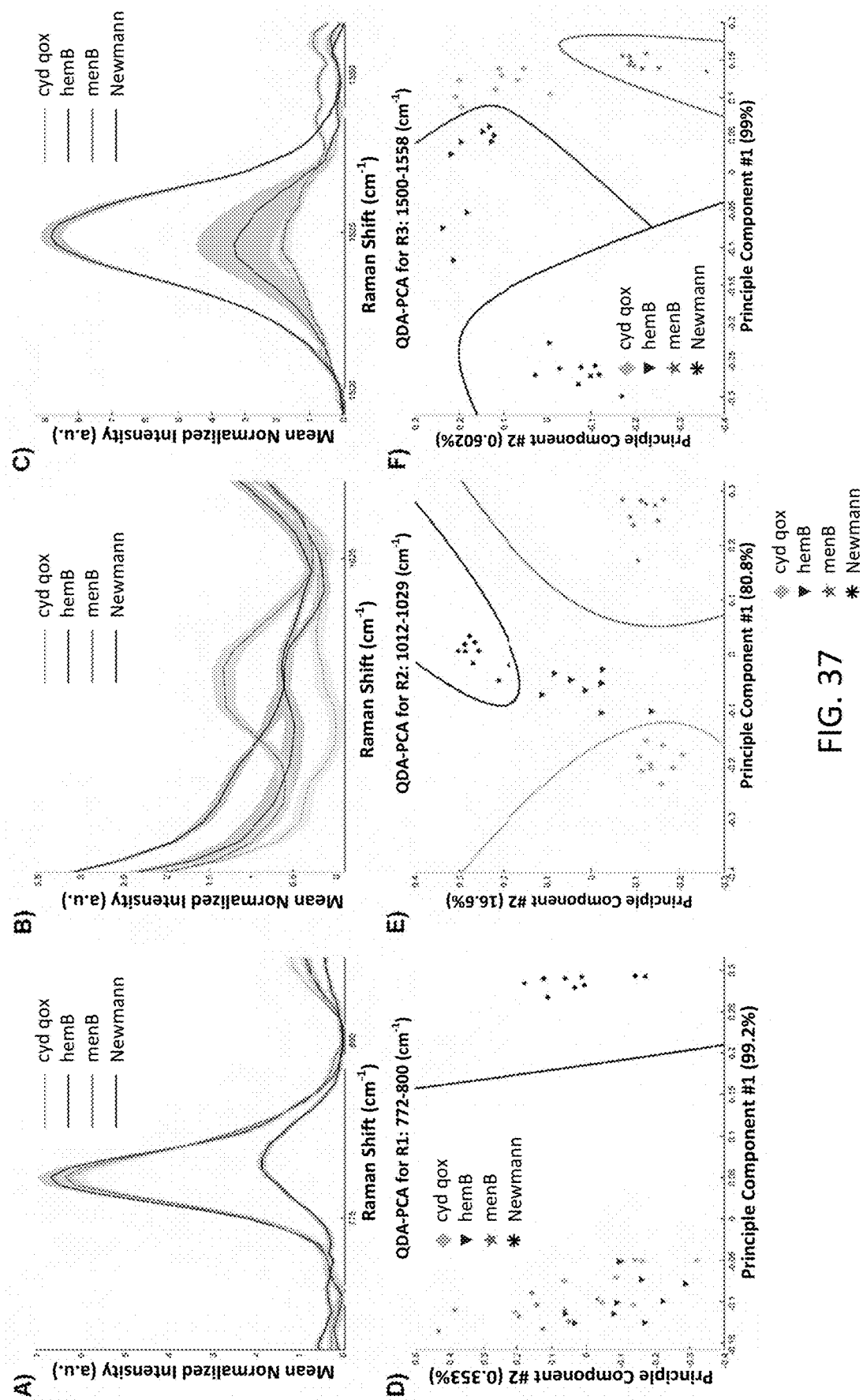
FIG. 37 shows spectral regions of interest and subsequent discriminant analysis for SCVs and Newman. (A) Spectral region No. 1 (772-800 cm$^{-1}$). (B) Spectral region No. 2 (10121029 cm$^{-1}$). (C) Spectral region No. 3 (1500-1558 cm$^{-1}$). (D) Quadratic discriminant analysis (QDA) performed on the PCA scores for spectral region No. 1 of SCVs and Newman. (E) Quadratic discriminant analysis (QDA) performed on the PCA scores for spectral region No. 2 of SCVs and Newman. (F) Quadratic discriminant analysis (QDA) performed on the PCA scores for spectral region No. 3 of SCVs and Newman. ***add delta in strain name for each and italicize and change to Newman.

A QDA analysis using PCA-SVD of each of the spectral regions of interest was implemented to determine discrimination amongst SCVs. For the first spectral region of interest of the SCV data (772-800 cm$^{-1}$), the Newman strain was successfully distinguished from the rest of the SCVs with a PC1 of 99.2% and PC2 of 0.35% (FIG. 36D). This was mainly (99.2%) dependent on the Raman peak that dominated this spectral region located at ~781 cm$^{-1}$ (uracil ring stretching), which was significantly lower in Newman compared to the other SCVs. The second spectral region (1012-1029 cm$^{-1}$) of interest showed discrimination between Newman, Δcyd Δqox, ΔhemB, and ΔmenB with PC1 (80.8%) and PC2 (16.6%) (FIG. 36E). The main band highlighted within this spectral region was ~1015-1017 cm$^{-1}$, which includes tryptophan (amino acid) and C—O stretch as part of the DNA backbone. The significance from this second spectral region was that each of the SCVs could be distinguished from each other and from Newman. The third spectral region (1500-1558 cm$^{-1}$) what was analyzed for the SCVs presented discrimination between Newman, Δcyd Δqox, ΔhemB, and ΔmenB with PC1 (99.0%) and PC2 (0.6%) (FIG. 36F). Similarly to the second spectral region, each of the SCVs and WT Newman were successfully distinguished using QDA based on the scores of the first two components generated by PCA. The main biochemical features within this spectral region include 1524 cm$^{-1}$ (carotenoid) and 1555 cm$^{-1}$ (tryptophan). These findings indicate that not only can Raman microspectroscopy be used to identify the presence of SCVs, but that this technology can be applied to categorize the type of SCV without the need for time-consuming culture-based methods.

According to the embodiments of the invention, the discrimination of antibiotic resistant *S. aureus* strains compared to methicillin-sensitive strains and other *S. aureus* mutants using Raman microspectroscopy is shown. In addition, virulent GBS strains were distinguished based on the presence of a carotenoid feature. Based on the spectral regions of the Raman spectra used for analysis, which were determined using the loadings from PCA, different discrimination patterns were determined. One spectral region that was identified was able to successfully discriminate amongst methicillin-resistant *S. aureus* (MRSA) and methicillin-sensitive *S. aureus* in addition to other *S. aureus* mutants using quadratic discriminant analysis (QDA). These findings motivated us to investigate other antibiotic tolerant strains commonly seen in hospital-acquired infections, called small colony variants (SCVs). Determination of three spectral regions for discriminatory analysis was again based on the PCA loadings for the SCVs. Across the collected Raman spectra, two of these spectral regions were able to provide statistically signification biochemical features important for discrimination amongst the SCVs. These findings further support the ability of Raman microspectroscopy to identify and categorize antibiotic tolerance in bacterial strains by implementing a statistical approach that minimizes overfitting of the data while identifying biomarkers for discrimination. In addition, our approach provides critical discriminatory information based on biochemical differences, while minimizing the time for culture as seen in SCVs that could be extended to other nosocomial pathogens. This technique and statistical analysis approach has the potential to play a major role in identifying multi-drug resistant pathogens to guide care providers with accurate information for proper and timely treatment.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LISTING OF REFERENCES

[1]. Rovers, M. M. The burden of otitis media. *Vaccine* 26, 2-8 (2008).

[2]. Monasta, L. et al. Burden of disease caused by otitis media: Systematic review and global estimates. *PLoS One* 7, (2012).

[3]. Berman, S. REVIEW Otitis Media in Developing Countries. 96, (1995).

[4]. Harmes, K. M. et al. Otitis media: diagnosis and treatment. *Am. Famr. Physician* 88, 435-40 (2013).

[5]. Lieberthal, A. S. et al. The Diagnosis and Management of Acute Otitis Media. *Pediatrics* 131, e964-e999 (2013).

[6]. Kathleen A. Daly and G. Scott Giebink. Clinical epidemiology of otitis media. *Pediatr. Infect. Dis. J.* 19, S31-S36 (2000).

[7]. Paul G. Shekelle, Glenn Takata, Sydne J. Newberry, Tumaini Coker, Mary Ann Limbos, Linda S. Chan, Martha J. Suttorp, Jason Carter, Aneesa Motala, Di Valentine, Breanne Johnsen, R. S. Management of acute otitis media. *Evid. Rep. Technol. Assess. (Full. Rep)*. 1-426 (2010).

[8]. American Academy of Family Physicians, American Academy of Otolaryngology-Head and Neck Surgery, and A. A. of P. S. on O. M. W. E. American academy of pediatrics. *Pediatrics* 113, 1412-1429 (2004).

[9]. Pelton, S. I. Otoscopy for the diagnosis of otitis media. *Pediatr. Infect. Dis. J.* 17, 540-543 (1998).

[10]. Sundberg, M., Peebo, M., Öberg, P. A., Lundquist, P. G. & Stromberg, T. Diffuse reflectance spectroscopy of the human tympanic membrane in otitis media. *Physiol. Meas.* 25, 1473-1483 (2004).

[11]. Sorrell, M. J., Tribble, J., Reinisch, L., Werkhaven, J. A. & Ossoff, R. H. Bacteria identification of otitis media with fluorescence spectroscopy. *Lasers Surg. Med.* 14, 155-163 (1994).

[12]. Brian C. Spector, Lou Reinisch, Dana Smith, J. A. W. Noninvasive fluorescent identification of bacteria causing acute otitis media in a chinchilla model. *The Laryngoscope*2 110, 1119-1123 (2000).

[13]. Monroy, G. L. et al. Noninvasive depth-resolved optical measurements of the tympanic membrane and middle ear for differentiating otitis media. *Laryngoscope* 125, E276-E282 (2015).

[14]. Anzenbacher, J. T. and P. *Raman and IR spectroscopy in biology and biochemistry*. (1994).

[15]. Ellis, D. I., Cowcher, D. P., Ashton, L., O'Hagan, S. & Goodacre, R. Illuminating disease and enlightening biomedicine: Raman spectroscopy as a diagnostic tool. *Analyst* 138, 3871-84 (2013).

[16]. C. Krafft, S. Dochow, I. Latka, B. Dietzek, J. P. Diagnosis and screening of cancer tissues by fiber-optic probe Raman spectroscopy. *Biomed. Spectrosc. Imaging* 1, 39-55 (2012).

[17]. Tu, Q. & Chang, C. Diagnostic applications of Raman spectroscopy. *Nanomedicine Nanotechnology, Biol. Med.* 8, 545-558 (2012).

[18]. Maquelin, K., Vreeswijk, T. Van, Endtz, H. & Smith, B. Raman spectroscopic method for identification of clinically relevant. *Anal. Chem* 72, 12-19 (2000).

[19]. Sandt, C., Smith-Palmer, T., Pink, J., Brennan, L. & Pink, D. Confocal Raman microspectroscopy as a tool for studying the chemical heterogeneities of biofilms in situ. *J. Appl. Microbiol.* 103, 1808-1820 (2007).

[20]. Maquelin, K. et al. Raman spectroscopic typing reveals the presence of carotenoids in *Mycoplasma pneumoniae*. *Microbiology* 155, 2068-2077 (2009).

[21]. de Siqueira e Oliveira, F. S., Giana, H. E. & Silveira, L. Discrimination of selected species of pathogenic bacteria using near-infrared Raman spectroscopy and principal components analysis. *J. Biomed. Opt.* 17, 107004 (2012).

[22]. Jarvis, R. M., Brooker, A. & Goodacre, R. Surface-enhanced Raman scattering for the rapid discrimination of bacteria. *Faraday Discuss.* 132, 281-292 (2006).

[23]. Lieber C. A., M.-J. A. Automated Method for Subtraction of Flourescence from Biological Raman Spectra. *As* 57, 1363-1367 (2003).

[24]. Savitzky, A. & Golay, M. J. E. Smoothing and Differentiation of Data by Simplified Least Squares Procedures. *Anal. Chem.* 36, 1627-1639 (1964).

[25]. Krishnapuram, B., Carin, L., Figueiredo, M. A. T. & Hartemink, A. J. Sparse multinomial logistic regression: Fast algorithms and generalization bounds. *IEEE Trans. Pattern Anal. Mach. Intell.* 27, 957-968 (2005).

[26]. Pence, I. J., Patil, C. A., Lieber, C. A. & Mahadevan-Jansen, A. Discrimination of liver malignancies with 1064 nm dispersive Raman spectroscopy. *Biomed. Opt. Express* 6, 2724-37 (2015).

[27]. Patrick R. Murray, Ellen J. Baron, James H. Jorgensen, Marie L. Landry, M. A. P. *Manual of Clinical Microbiology.* (ASM Press, 2007).

[28]. Ventola, C. L. The antibiotic resistance crisis: part 1: causes and threats. *P T A peer-reviewed J. Formul. Manag.* 40, 277-83 (2015).

[29]. Post, J. C. et al. Molecular analysis of bacterial pathogens in otitis media with effusion. *Jama* 273, 1598-1604 (1995).

[30]. Matar, G. M., Sidani, N., Fayad, M. & Hadi, U. Two-step PCR-based assay for identification of bacterial etiology of otitis media with effusion in infected Lebanese children. *J. Clin. Microbiol.* 36, 1185-1188 (1998).

[31]. Rayner, M. G. et al. Evidence of bacterial metabolic activity in culture-negative otitis media with effusion. *JAMA* 279, 296-9 (1998).

[32]. Woude, M. W. Van Der & Baumler, A. J. Phase and Antigenic Variation in Bacteria Phase and Antigenic Variation in Bacteria. *Clin. Microbiol. Rev.* 17, 581-611 (2004).

[33]. Lafontaine, E. R. et al. Expression of the *Moraxella catarrhalis* UspA1 Protein Undergoes phase Variation and Is Regulated at the Transcription Level. *J. Bacteriol.* 183, 1540-1551 (2001).

[34]. Oust, A. et al. Fourier Transform Infrared and Raman Spectroscopy for Characterization of *Listeria monocytogenes* Strains. *Society* 72, 228-232 (2006).

[35]. Leibovitz, E., Broides, A., Greenberg, D. & Newman, N. Current management of pediatric acute otitis media. *Expert Rev. Anti. Infect. Ther.* 8, 151-161 (2010).

[36]. Grossman, Z. et al. Antibiotic prescribing for upper respiratory infections: European primary paediatricians'knowledge, attitudes and practice. *Acta Paediatr. Int. J. Paediatr.* 101, 935-940 (2012).

[37]. Zielnik-Jurkiewicz, B. & Bielicka, A. Antibiotic resistance of *Streptococcus pneumoniae* in children with acute otitis media treatment failure. *Int. J. Pediatr.* Otorhinolaryngol. 79, 2129-2133 (2015).

[38]. Dagan, R. Treatment of acute otitis media—Challenges in the era of antibiotic resistance. *Vaccine* 19, 2-9 (2000).

[39]. Klein, J O, The burden of otitis media. *Vaccine,* 2001, 19:S2-S8.

[40]. Ahmed, S, Incremental health care utilization and costs for acute otitis media in children. *The Laryngoscope,* 2014, 124:301-305.

[41]. Burrows, H L, et al., Otitis Media Guideline Team. *University of Michigan Health System otitis media guideline,* 2013, http://www.med.umich.edu/1info/fhp/practiceguides/om/OM.pdf.

[42]. Bluestone C D, Klein J O. Otitis Media and Eustachian Tube Dysfunction. In: Bluestone C D, Simons J P, Healy G B, eds. Pediatric Otolaryngology. 5th ed. Shelton, Conn: People's Medical Publishing House; 2014:633-759.

[43]. Pichichero, M E, Acute Otitis Media: Part I. Improving Diagnostic Accuracy. *American Family Physician,* 2000, 61(7):2051-2056.

[44]. Marchetti F, Ronfani L, Nibali S C, et al.; *Italian Study Group on Acute Otitis Media.* Delayed prescription may reduce the use of antibiotics for acute otitis media: a prospective observational study in primary care. *Arch Pediatr Adolesc Med.* 2005, 159(7):679-684.

[45]. Burkhard, M D and Sachs, R M. Anthropometric manikin for acoustic research. *Journal of the Acoustical Society of America,* 1975, 58:214-222.

[46]. Lucente, F E. (1995). Anatomy, histology, and physiology. In: *The External Ear,* Lucente, F E, Lawson, W, and Novick, N L (Eds.). Philadelphia: W.B. Sounders Company.

[47]. Muller, C. Tympanoplasty. Grand Rounds paper. Houston: Department of Otolaryngology. University of Texas. Retrieved Nov. 4, 2015 from http://www.utmb.edu/otoref/Grnds/T-plasty-030115/T-plastyslides-030115.pdf.

[48]. Alvord, L S and Farmer, B L. Anatomy and orientation of the human external ear. *Journal of the American Academy of Audiology,* 1997, 8:383-390.

[49]. Bekesy, G von. The structure of the middle ear and hearing of one's own voice by bone conduction. *Journal of the Acoustical Society of America,* 1949, 21:217-232.

[50]. Zemlin, W R. (1997). *Speech and Hearing Science: Anatomy and Physiology* ($4^{th}$ Ed.). Boston: Allyn and Bacon.

[51]. Shaw, E A G. (1974). The external ear. In: *Handbook of Sensory Physiology* (Vol. VI): Auditory System, Keidel, W D and Neff, W D (Eds.). New York: Springer-Verlag.

[52]. Seikel, J A, King, D W, and Drumright, D G. (2000). *Anatomy and Physiology for Speech, Language, and Hearing.* San Diego: Singular Publishing Group.17. Gray, H. (1918). *Anatomy of the Human Body,* $20^{th}$ edition. Philadelphia: Lea and Febiger.

[53]. Stinson, M R and Lawton B W. Specification of geometry of the human ear canal for the predication of sound-pressure level distribution. *Journal of the Acoustical Society of America,* 1989, 85:2492-2503.

[54]. Decreamer, E F, Dirckx, J J, and Funnell, W R. Shape and derived geometrical parameters of the adult, human tympanic membrane measure with a phase-shift moiré interferometer. *Hearing Research,* 1991, 51:107-121.

[55]. Sundberg, M. (2008). Optical methods for tympanic membrane characterization. Linkoping Studies in Science and Technology, Dissertation No. 1173. Linkoping (Sweden) L Liu-Tryck.

[56]. Dallos, P. (1973). *The Auditory Periphery*. New York: Academic Press.

[57]. Yost, W and Nielson, D (1977). *Fundamentals of Hearing: An Introduction*. New York: Holt, Rinehart, and Winston.

[58]. Gelfand, H. (1998). *Hearing: An Introduction to Psychological and Physiological Acoustics*. New York: Mercel Decker.

[59]. Harris, J D. (1986). *Anatomy and Physiology of the Peripheral Auditory Mechanism*. Austin, Tex.: Pro-Ed.

[60]. Donaldson J A and Miller, J M. (1980). Anatomy of the ear. In: Otolaryngology, Pararella, M and Shumrick, D (Eds.), *Basic Sciences and Related Disciplines*, 1:26-42. Philadelphia: Sounders.

[61]. Kojo, Y. Morphological studies of the human tympanic membrane. *Journal of Oto-Rhino-Laryngological Society of Japan*, 1954, 57:115-126.

[62]. Lim, D J. Human tympanic membrane: An ultrastructural observation. *Acta Otolaryngologica*, 1970, 70:176-186.

[63]. Waver, E and Lawrence, M. (1954). Physiological Acoustics. Princeton, N.J.: Princeton University Press.

[64]. Dacraemer, W F, Maes, M A, and Vanhuyse, V J. An elastic stress-strain relation for soft biological tissues based on a structural model. *Journal of Biomechanics*, 1980, 13:463-468.

[65]. 36. Watters G W, Jones J E, Freeland A P. The predictive value of tympanometry in the diagnosis of middle ear effusion. *Clinical Otolaryngology Allied Science*, 1997, 22(4):343-345.

[66]. Kimball S. Acoustic reflectometry: spectral gradient analysis for improved detection of middle ear effusion in children. *Journal of Pediatric Infectious Diseases*, 1998, 17(6):552-555.

[67]. L. Hall-Stoodley, F. Z. Hu, A. Gieseke, L. Nistico, D. Nguyen, J. Hayes, et al., Direct detection of bacterial biofilms on the middle-ear mucosa of children with chronic otitis media, *JAMA*, 2006, 296:202-211.

[68]. L. P. Schousboe, T. Ovesen, L. Eckhardt, L. M. Rasmussen, C. B. Pedersen, How does endotoxin trigger inflammation in otitis media with effusion? *Laryngoscope*, 2001, 111:297-300.

[69]. U. Gok, Y. Bulut, E. Keles, S. Yalcin, M. Z. Doymaz, Bacteriological and PCR analysis of clinical material aspirated from otitis media with effusions, *Int. J. Pediatr. Otorhinolaryngology*, 2001, 60:49-54.

[70]. D. M. Poetker, D. R. Lindstrom, C. E. Edmiston, C. J. Krepel, T. R. Link, J. E. Kerschner, Microbiology of middle ear effusions from 292 patients undergoing tympanostomy tube placement for middle ear disease, *Int. J. Pediatr. Otorhinolaryngol*. 69 (2005) 799-804.

[71]. C. D. Bluestone, J. S. Stephenson, L. M. Martin, Ten-year review of otitis media pathogens, Pediatr. Infect. Dis. J. 11 (8 Suppl.) (1992) S7-S11.

[72]. Daniel, M, Imtiaz-Umer, S, Fergie, N, Birchall, J P, Bayston, R. Bacterial involvement in otitis media with effusion. *International Journal of Pediatric Otorhinolaryngology*, 2012, 76:1416-1422.

[73]. Maquelin, K, Kirschner, C, Choo-Smith, L.-P., van den Braak, N., Endtz, H. Ph., Naumann, D., Puppels, G. J. Identification of medically relevant microorganisms by vibrational spectroscopy. *Journal of Microbiological Methods*, 2002, 51:255-271.

[74]. O'Leary M., Practical Handbook of Microbiology, (CRC Press, Inc., Boca Raton, Fla., 1989), p. 352-353.

[75]. Dai, T, Gupta, A, Huang, Y-Y, Sherwood, M E, Murray, C K, Vrahas, M S, Kielian, T, Hamblin, M R. Blue Light Eliminates Community-Acquired Methicillin-Resistant *Staphylococcus aureus* in Infected Mouse Skin Abrasions. *Photomedicine and Laser Surgery*, 2013, 31(11): p. 531-538.

[76]. 57. Moffit, T, Chen, Y-C, and Prahl, S A. Preparation and characterization of polyurethane optical phan-toms. *Journal of Biomedical Optics*, 2006, 11(4):041103.

[77]. Wang, J, Bergholt, M S, Zheng, W, Huang, Z. Development of a beveled fiber-optic confocal Raman probe for enhancing in vivo epithelial tissue Raman measurements at endoscopy. *Optics Letters*, 2013, 38(13):2321-2323.

[78]. Keller, M D, Vargis, E, Granja, N M, Wilson, R H, Mycek, M A, Kelley, M C, Mahadevan-Jansen, A. Development of a spatially offset Raman spectroscopy probe for breast tumor surgical margin evaluation. *Journal of Biomedical Optics*, 2011, 16(7): 0077006.

[79]. Ehrlich, G D, Veeh, R, Wang, X, Costerton, J W, Hayes, J D, Hu, F Z, Diagle, B J, Ehrlich, M D, Post, J C. Mucosal biofilm formation on middle-ear mucosa in the chinchilla model of otitis media. *Journal of the American Medical Association*, 2002, 287(13):1710-1715.

[80]. S. S. Magill et al., "Multistate Point-Prevalence Survey of Health Care-Associated Infections," *N. Engl. J. Med.*, vol. 370, no. 13, pp. 1198-1208, 2014.

[81]. L. L. Leape et al., "The nature of adverse events in hospitalized patients: Results of the Harvard Medical Practice Study I I," vol. 324, no. 6, pp. 377-384, 1991.

[82]. R. D. Scott I I, "The direct medical costs of healthcare-associated infections in U.S. hospitals and the benefits of prevention," 2009.

[83]. G. A. Noskin et al., "The burden of *Staphylococcus aureus* infections on hospitals in the United States," vol. 165, pp. 1756-1761, 2005.

[84]. M. Sangappa and P. Thiagarajan, "Methicillin Resistant *Staphylococcus Aureus*: Resistance Genes and Their Regulation," *Int. J. Pharm. Pharm. Sci.*, vol. 4, pp. 658-667, 2012.

[85]. J. Fishovitz, J. A. Hermoso, M. Chang, and S. Mobashery, "Penicillin-binding protein 2a of methicillin-resistant *Staphylococcus aureus*," *IUBMB Life*, vol. 66, no. 8, pp. 572-577, 2014.

[86]. E. Klein, D. L. Smith, and R. Laxminarayan, "Hospitalizations and deaths caused by methicillin-resistant *Staphylococcus aureus*, United States, 1999-2005," vol. 13, no. 12, pp. 1840-1846, 2007.

[87]. O. Melter and B. Radojevič, "Small Colony Variants of *Staphylococcus aureus*-review," *Folia Microbiol. (Praha).*, vol. 55, no. 6, pp. 548-558, 2010.

[88]. F. Kipp et al., "Evaluation of Two Chromogenic Agar Media for Recovery and Identification of *Staphylococcus aureus* Small-Colony Variants," *J. Clin. Microbiol.*, vol. 43, no. 4, pp. 1956-1959, 2005.

[89]. M. R. Precit, D. J. Wolter, A. Griffith, J. Emerson, J. L. Burns, and L. R. Hoffman, "Optimized In Vitro Antibiotic Susceptibility Testing Method for Small-Colony Variant *Staphylococcus aureus*," *Antimicrob. Agents Chemother.*, vol. 60, no. 3, pp. 1725-1735, 2016.

[90]. P. W. Groundwater et al., "Methods for the detection and identification of pathogenic bacteria: past, present, and future," *Chem. Soc. Rev.*, vol. 46, no. 16, pp. 4818-4832, 2017.

[91]. P. Kralik and M. Ricchi, "A Basic Guide to Real Time PCR in Microbial Diagnostics: Definitions, Parameters, and Everything," *Front. Microbiol.*, vol. 8, no. 108, pp. 1-9, 2017.

[92]. W. E. Huang, R. I. Griffiths, I. P. Thompson, M. J. Bailey, and A. S. Whiteley, "Raman microscopic analysis of single microbial cells," *Anal. Chem.*, vol. 76, no. 15, pp. 4452-4458, 2004.

[93]. K. Maquelin et al., "Prospective study of the performance of vibrational spectroscopies for rapid identification of bacterial and fungal pathogens recovered from blood cultures.," *J. Clin. Microbiol.*, vol. 41, no. 1, pp. 324-9, 2003.

[94]. S. Pahlow, S. Meisel, D. Cialla-May, K. Weber, P. Rösch, and J. Popp, "Isolation and identification of bacteria by means of Raman spectroscopy," *Adv. Drug Deliv. Rev.*, vol. 89, pp. 105-120, 2015.

[95]. O. Ayala et al., "Characterization of bacteria causing acute otitis media using Raman microspectroscopy," *Anal. Methods*, vol. 9, pp. 1864-1871, 2017.

[96]. G. Y. Liu et al., "*Staphylococcus aureus* golden pigment impairs neutrophil killing and promotes virulence through its antioxidant activity," *J. Exp. Med.*, vol. 202, no. 2, pp. 209-215, 2005.

[97]. K. Czamara, K. Majzner, M. Z. Pacia, K. Kochan, A. Kaczor, and M. Baranska, "Raman spectroscopy of lipids: a review," *J. Raman Spectrosc.*, vol. 46, pp. 4-20, 2014.

[98]. R. Procter, A. Kriegeskorte, B. Kahl, K. Becker, B. Loffler, and G. Peters, "*Staphylococcus aureus* Small Colony Variants (SCVs): a road map for the metabolic pathways involved in persistent infections," *Front. Cell. Infect. Microbiol.*, vol. 4, no. 99, pp. 1-8, 2014.

[99]. E. Duthie and L. Lorenz, "Staphylococcal Coagulase: Mode of Action and Antigenicity," *Microbiology*, vol. 6, pp. 95-107, 1952.

[100]. C. L. C. Wielders, A. C. Fluit, S. Brisse, J. Verhoef, and F. J. Schmitz, "mecA gene is widely disseminated in *Staphylococcus aureus* population," *J. Clin. Microbiol.*, vol. 40, no. 11, pp. 3970-3975, 2002.

[101]. B. Ballhausen, A. Kriegeskorte, N. Schleimer, G. Peters, and K. Becker, "The mecA homolog mecC confers resistance against β-lactams in *Staphylococcus aureus* irrespective of the genetic strain background," *Antimicrob. Agents Chemother.*, vol. 58, no. 7, pp. 3791-3798, 2014.

[102]. L. Lan, A. Cheng, P. M. Dunman, D. Missiakas, and C. He, "Golden Pigment Production and Virulence Gene Expression Are Affected by Metabolisms in *Staphylococcus aureus*," *J. Bacteriol.*, vol. 192, no. 12, pp. 3068-3077, 2010.

[103]. A. Qamar and D. Golemi-Kotra, "Dual Roles of FmtA in *Staphylococcus aureus* Cell Wall Biosynthesis and Autolysis," *Antimicrob. Agents Chemother.*, vol. 56, no. 7, pp. 3797-3805, 2012.

[104]. B. R. Boles, M. Thoendel, A. J. Roth, and A. R. Horswill, "Identification of Genes Involved in Polysaccharide-Independent *Staphylococcus aureus* Biofilm Formation," *PLoS One*, vol. 5, no. 4, 2010.

[105]. N. D. Hammer et al., "Two Heme-Dependent Terminal Oxidases Power *Staphylococcus aureus* Organ-Specific Colonization of the Vertebrate Host," *M Bio*, vol. 4, no. 4, pp. 1-9, 2013.

[106]. C. Von Eiff, C. Heilmann, R. A. Proctor, C. Woltz, G. Peters, and F. Gotz, "A site-directed *Staphylococcus aureus* hemB mutant is a small-colony variant which persists intracellularly," *J. Bacteriol.*, vol. 179, no. 15, pp. 4706-4712, 1997.

[107]. C. A. Wakeman et al., "Menaquinone biosynthesis potentiates haem toxicity in *Staphylococcus aureus*," *Mol. Microbiol.*, vol. 86, no. 6, pp. 1376-1392, 2013.

[108]. J. Shlens, "A Tutorial on Principal Component Analysis," 2014.

What is claimed is:

1. A method for identification and discrimination of bacteria and/or mutant and/or resistant bacterial strains in a biological fluid, comprising:
    illuminating the biological fluid with a beam of light;
    obtaining Raman spectra from light scattered from the illuminated biological fluid; and
    finding Raman signatures corresponding to each type of bacteria and/or mutant and/or resistant bacterial strains from the obtained Raman spectra, so as to identify and discriminate each type of bacteria and/or mutant and/or resistant bacterial strains in the biological fluid from the Raman signatures,
    wherein said finding the Raman signatures comprises processing the obtained Raman spectra with a multi-class support vector machine (SVM) algorithm and a linear discriminant analysis to find the Raman signatures corresponding to each type of bacteria and/or mutant and/or resistant bacterial strains.

2. The method of claim 1, wherein the biological fluid comprises a middle ear fluid (MEF).

3. The method of claim 2, wherein the bacteria that cause acute otitis media (AOM) in the biological fluid comprise *H. influenzae, M catarrhalis*, and/or *S. pneumoniae*.

4. The method of claim 1, wherein the bacteria comprise *S. agalactiae*, and/or *S. aureus*.

5. The method of claim 4, wherein the mutant bacterial strains are derived from the *S. aureus* parent strain.

6. The method of claim 1, wherein the illuminating step comprises illuminating the biological fluid with the beam of light from a near-infrared light source.

7. The method of claim 1, wherein the obtaining step comprises collecting the scattered light with an optical probe and obtaining the Raman spectra of the scattered light into with a spectrometer.

8. A system for identification and discrimination of bacteria and/or mutant bacterial strains in a biological fluid, comprising:
    an optical probe optically connected to a light source for emitting a beam of light and configured to deliver the beam of light emitted from the light source to the biological fluid and to collect light scattered from the biological fluid;
    a detector optically coupled with the optical probe, for obtaining Raman spectra from the collected scattered light; and
    a controller in communication with the detector and programmed for finding Raman signatures corresponding to each type of bacteria and/or mutant and/or resistant bacterial strains from the obtained Raman spectra and identifying and discriminating each type of bacteria and/or mutant and/or resistant bacterial strains in the biological fluid from the Raman signatures,
    wherein said finding the Raman signatures comprises processing the obtained Raman spectra with a multi-class support vector machine (SVM) algorithm and a linear discriminant analysis to find the Raman signatures corresponding to each type of bacteria and/or mutant and/or resistant bacterial strains.

9. The system of claim 8, wherein the biological fluid comprises a middle ear fluid (MEF).

10. The system of claim 9, wherein bacteria that cause acute otitis media (AOM) in the biological fluid comprise *H. influenzae, M catarrhalis*, and/or *S. pneumoniae*.

11. The system of claim 8, wherein the bacteria comprise *S. agalactiae*, and/or *S. aureus*.

12. The system of claim 11, wherein the mutant bacterial strains are derived from the *S. aureus* parent strain.

13. The system of claim 8, wherein the light source comprises a laser or light emitting diodes (LEDs).

14. The system of claim 13, wherein the beam of light has a wavelength in a near-infrared range.

15. The system of claim 8, wherein the optical probe has a working end, a source channel and a plurality of collection channels, wherein the working end is operably positioned proximate to a surface of the biological fluid, the source channel is configured to deliver the beam of light emitted by the light source from the working end to the surface of the biological fluid, and the collection channels are configured to collect from the working end light scattered from the illuminated biological fluid.

16. The system of claim 8, wherein the optical probe comprises a plurality of optical fibers spatially arranged in a fiber array.

17. The system of claim 16, wherein at least one fiber of the plurality of optical fibers is a source optical fiber for delivering the beam of light emitted from the light source to the surface of the biological fluid, and the remaining fibers of the plurality of optical fibers are collection optical fibers for collecting light scattered from the illuminated biological fluid.

18. The system of claim 17, wherein the source optical fiber is positioned in a center of the fiber array, and the collection optical fibers are positioned in one or more rings having a center at the source optical fiber such that each collection optical fiber is offset from the source optical fiber.

19. The system of claim 18, wherein the source optical fiber is surrounded by the collection optical fibers, so that a working end of the optical probe is formed by a ring of beveled collection fibers.

20. The system of claim 19, wherein the optical probe further comprises a ball lens operably placed at a distance from the working end to focus the beam of light on the biological fluid.

21. The system of claim 17, wherein the collection optical fibers are positioned in one or more rings having a center at the source optical fiber such that each collection optical fiber is offset from the source optical fiber.

22. The system of claim 21, wherein the source optical fiber is placed proximate to an edge of the optical probe.

23. The system of claim 17, wherein the optical probe further comprises LED or illuminating fibers for determining placement information of the optical probe.

24. The system of claim 8, wherein the detector comprises a spectrometer.

25. The system of claim 24, wherein the detector further comprises a charge-coupled device (CCD).

26. A system for characterizing contents of a bio-object, comprising:
an optical probe optically connected to a light source for emitting a beam of light and configured to deliver the beam of light emitted from the light source to the bio-object and to collect light scattered from the bio-object;
a detector optically coupled with the optical probe, for obtaining Raman data from the collected scattered light; and
a controller in communication with the detector and programmed for finding Raman signatures corresponding to biochemical compositions from the obtained Raman data and identifying and discriminating the contents of the bio-object from the Raman signatures,
wherein the optical probe comprises a plurality of optical fibers spatially arranged in a fiber array;
wherein at least one fiber of the plurality of optical fibers is a source optical fiber for delivering the beam of light emitted from the light source to the surface of the bio-object, and the remaining fibers of the plurality of optical fibers are collection optical fibers for collecting light scattered from the illuminated bio-object; and
wherein the optical probe further comprises at least one light-emitting diode (LED) for determining placement information of the optical probe.

27. The system of claim 26, wherein the bio-object comprises a middle ear fluid (MEF).

28. The system of claim 27, wherein the contents of the bio-object comprise bacteria that cause acute otitis media (AOM), wherein the bacteria comprise *H. influenzae, M catarrhalis*, and/or *S. pneumoniae*.

29. The system of claim 26, wherein the contents of the bio-object comprise *S. agalactiae*, and/or *S. aureus*.

30. The system of claim 29, wherein the contents of the bio-object comprise methicillin-resistant *S. aureus* (MRSA).

31. The system of claim 26, wherein the light source comprises a laser or light emitting diodes (LEDs).

32. The system of claim 31, wherein the beam of light has a wavelength in a near-infrared range.

33. The system of claim 26, wherein the source optical fiber is positioned in a center of the fiber array, and the collection optical fibers are positioned in one or more rings having a center at the source optical fiber such that each collection optical fiber is offset from the source optical fiber.

34. The system of claim 33, wherein the source optical fiber is surrounded by the collection optical fibers, so that a working end of the optical probe is formed by a ring of beveled collection fibers.

35. The system of claim 34 wherein the optical probe further comprises a ball lens operably placed at a distance from the working end to focus the beam of light on the bio-object.

36. The system of claim 34, wherein the collection optical fibers are positioned in one or more rings having a center at the source optical fiber such that each collection optical fiber is offset from the source optical fiber.

37. The system of claim 36, wherein the source optical fiber is placed proximate to an edge of the optical probe.

38. The system of claim 26, wherein the detector comprises a spectrometer.

39. The system of claim 38, wherein the detector further comprises a charge-coupled device (CCD).

* * * * *